United States Patent
Datta et al.

(10) Patent No.: US 11,944,429 B2
(45) Date of Patent: *Apr. 2, 2024

(54) AUTOMATICALLY CLASSIFYING ANIMAL BEHAVIOR

(71) Applicant: President and Fellows of Harvard College, Cambridge, MA (US)

(72) Inventors: Sandeep Robert Datta, Cambridge, MA (US); Alexander B. Wiltschko, Cambridge, MA (US); Matthew J. Johnson, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/180,677

(22) Filed: Mar. 8, 2023

(65) Prior Publication Data

US 2023/0225636 A1    Jul. 20, 2023

Related U.S. Application Data

(63) Continuation of application No. 17/241,863, filed on Apr. 27, 2021, now Pat. No. 11,622,702, which is a (Continued)

(51) Int. Cl.
*A61B 5/11* (2006.01)
*A61B 5/00* (2006.01)
(Continued)

(52) U.S. Cl.
CPC .............. *A61B 5/1128* (2013.01); *A61B 5/00* (2013.01); *A61B 5/1123* (2013.01); (Continued)

(58) Field of Classification Search
None
See application file for complete search history.

(56) References Cited

U.S. PATENT DOCUMENTS 6,678,413 B1    1/2004   Liang et al.
7,269,516 B2 *  9/2007   Brunner ................. G16H 10/20
                                                       382/128
(Continued)

FOREIGN PATENT DOCUMENTS

CN    104881651 A  *  9/2015   ......... G06K 9/00335
CN    104881651 A     9/2015
(Continued)

OTHER PUBLICATIONS

International Patent Application Publication WO2013170129A1 (Year: 2013).*

(Continued)

*Primary Examiner* — Soo Shin
(74) *Attorney, Agent, or Firm* — Wolf, Greenfield & Sacks, P.C.

(57) ABSTRACT

Systems and methods are disclosed to objectively identify sub-second behavioral modules in the three-dimensional (3D) video data that represents the motion of a subject. Defining behavioral modules based upon structure in the 3D video data itself— rather than using a priori definitions for what should constitute a measurable unit of action— identifies a previously-unexplored sub-second regularity that defines a timescale upon which behavior is organized, yields important information about the components and structure of behavior, offers insight into the nature of behavioral change in the subject, and enables objective discovery of subtle alterations in patterned action. The systems and methods of the invention can be applied to drug or gene therapy classification, drug or gene therapy screening, disease study including early detection of the onset of a disease, toxicology research, side-effect study, learning and memory process study, anxiety study, and analysis in consumer behavior.

20 Claims, 34 Drawing Sheets

Related U.S. Application Data continuation of application No. 15/767,544, filed as application No. PCT/US2016/056471 on Oct. 11, 2016, now Pat. No. 11,020,025.

(60) Provisional application No. 62/241,627, filed on Oct. 14, 2015.

(51) Int. Cl.
| | |
|---|---|
| *G06F 18/20* | (2023.01) |
| *G06F 18/2135* | (2023.01) |
| *G06T 7/20* | (2017.01) |
| *G06V 10/147* | (2022.01) |
| *G06V 10/77* | (2022.01) |
| *G06V 10/84* | (2022.01) |
| *G06V 40/20* | (2022.01) |

(52) U.S. Cl.
CPC ........ *A61B 5/7267* (2013.01); *G06F 18/2135* (2023.01); *G06F 18/295* (2023.01); *G06V 10/7715* (2022.01); *G06V 10/85* (2022.01); *G06V 40/20* (2022.01); *A61B 2503/40* (2013.01); *A61B 2503/42* (2013.01); *A61B 2576/00* (2013.01); *G06T 7/20* (2013.01); *G06V 10/147* (2022.01)

(56) References Cited

U.S. PATENT DOCUMENTS

| | | | |
|---|---|---|---|
| 8,634,635 B2 | 1/2014 | Bai et al. | |
| 8,928,672 B2 * | 1/2015 | Corazza | G06T 13/40 345/473 |
| 9,152,851 B2 * | 10/2015 | Goulding | A01K 1/031 |
| 11,020,025 B2 | 6/2021 | Datta et al. | |
| 2003/0024482 A1 * | 2/2003 | Gondhalekar | A01K 29/005 119/422 |
| 2003/0028327 A1 | 2/2003 | Brunner et al. | |
| 2003/0048926 A1 | 3/2003 | Wantabe | |
| 2004/0030741 A1 * | 2/2004 | Wolton | G06F 16/954 709/202 |
| 2004/0111220 A1 * | 6/2004 | Ochs | G06F 18/2134 702/19 |
| 2004/0141635 A1 | 7/2004 | Liang et al. | |
| 2004/0141636 A1 | 7/2004 | Liang et al. | |
| 2005/0163349 A1 | 7/2005 | Brunner et al. | |
| 2005/0240086 A1 * | 10/2005 | Akay | A61B 5/1124 600/595 |
| 2007/0225774 A1 * | 9/2007 | Eskandar | A61N 2/004 607/45 |
| 2007/0229522 A1 | 10/2007 | Wang et al. | |
| 2008/0152192 A1 | 6/2008 | Zhu et al. | |
| 2009/0220425 A1 | 9/2009 | Moxon et al. | |
| 2010/0034462 A1 | 2/2010 | Nevatia et al. | |
| 2011/0032334 A1 | 2/2011 | Raveendran et al. | |
| 2011/0158546 A1 | 6/2011 | Huang et al. | |
| 2011/0173143 A1 | 7/2011 | Benjamini et al. | |
| 2011/0184489 A1 * | 7/2011 | Nicolelis | A61N 1/36025 607/48 |
| 2012/0056800 A1 | 3/2012 | Williams et al. | |
| 2012/0078097 A1 | 3/2012 | Wang et al. | |
| 2013/0108177 A1 * | 5/2013 | Sukthankar | G06V 10/75 382/218 |
| 2015/0146939 A1 * | 5/2015 | Datta | A01K 67/00 382/110 |
| 2016/0059412 A1 * | 3/2016 | Oleynik | A47J 36/321 700/250 |
| 2018/0279921 A1 | 10/2018 | Datta et al. | |
| 2021/0369146 A1 | 12/2021 | Datta et al. | |

FOREIGN PATENT DOCUMENTS

| | | | | |
|---|---|---|---|---|
| JP | H11-296651 A | | 10/1999 | |
| JP | 2003-087771 A1 | | 3/2003 | |
| JP | 2005-196398 A | | 7/2005 | |
| JP | 2005-215927 A1 | | 8/2005 | |
| JP | 2007-328435 A | | 12/2007 | |
| JP | 2012-053716 A | | 3/2012 | |
| WO | WO 02/092101 A1 | | 11/2002 | |
| WO | WO 2010/113929 A1 | | 10/2010 | |
| WO | WO-2010113929 A1 | * | 10/2010 | ............. H04N 7/183 |
| WO | WO 2013/075054 A1 | | 5/2013 | |
| WO | WO 2013/170129 A1 | | 11/2013 | |
| WO | WO-2013170129 A1 | * | 11/2013 | ........... A01K 29/005 |
| WO | WO 2015/030689 A2 | | 3/2015 | |

OTHER PUBLICATIONS

James L. Crowley, Jean Marc Bedrune, Morten Bekker, Michael Schneider, "Integration and control of reactive visual processes," ECCV 1994: Computer Vision—ECCV '94 pp. 47-58 (Year: 1994).*
Lee et al., "Circuit Mechanisms Underlying Motor Memory Formation in the Cerebellum," Neuron 86, 529-540 (Year: 2015).*
WO 2010/113929 A1 (translation) (Year: 2010).*
Cn 104881651-A (Translation) (Year: 2015).*
Rahmati et al., "Cerebellar Potentiation and Learning a Whisker-Based Object Localization Task with a Time Response Window," The Journal of Neuroscience, Jan. 29, 2014, 34(5):1949-1962 (Year: 2014).*
Bertrand et al., "Filtered derivative with p-value method for multiple change-points detection," arXiv:1003.4147 [math.ST] (Year: 2010).*
Extended European Search Report for European Application No. EP 13788526.5, dated Jan. 13, 2017.
International Preliminary Report on Patentability for International Application No. PCT/US2013/040516, dated Nov. 20, 2014.
International Search Report and Written Opinion for International Application No. PCT/US2013/040516, dated Sep. 24, 2013.
Japanese Office Action dated Jan. 5, 2023 in connection with Japanese Application No. 2022-031186 and English translation thereof.
Response to 161/162 for European Application No. EP 13788526.5, filed Jun. 25, 2015.
Abrahams et al., Connecting Genes to Brain in the Autism spectrum disorders. Arch Neuorl. Apr. 2010; 67(4):395-9.
Benjamini et al., Quantifying the Buildup in Extent and Complexity Free Exploration in Mice. PNAS. Sep. 13, 2011;108 (Suppl 3):15580-7.
Benjamini et al., Ten Ways to Improve the Quality of Descriptions of Whole-Animal Movement. Neuroscience and Biobehavioral Reviews. Jul. 2010;34(8): 1351-65.
Bertrand et al., Filtered derivative with p-value method for multiple change-points detection. arXiv:1003.4147v1. Mar. 22, 2010. 6 pages.
Bill et al., Genetic Advances in Autism: Heterogeneity and Convergence on Shared Pathways. Current Opinion in Genetics and Development. Jun. 2009; 19(3):271-8.
Brennan et al., Pheromonal Communicate in Vertebrates. Nature. Nov. 16, 2006; 444(7117):308-15.
Broad et al., More to Pheromes Than Meets the Nose. Nature Neurosciences. Feb. 2008;11(2):28-9.
Cohen et al., Communicate Between the Synapse and the Nucleus in Neuronal Development, Plasticity, and Disease. Annual Rev Cell Dev Biol. 2008;24: 183-209.
Crawley et al., Mouse Behavioral Assays Relevant to the Symptoms of Autism. Brian Pathology. Oct. 2007; 17(4): 448-59.
Crawley, Behavioral Phenotypical Strategies for Mutant Mice. Neuron. Mar. 27, 2008; 57(6):809-18.
Crowley et al., Integration and Control of Reactive Visual Processes. In: Eklundh JO. (eds) Computer Vision—ECCV '94. Lecture Notes in Computer Science. 1994; 801:47-58.
Da Monteiro Silva, Master Theses: Automatic Behavior Recognition in Laboratory Animals Using Kinect. Faculdade de Engenharia da Universidade do Porto. Jul. 2012: 73 pages.
Fairless et al., Deconstructing Sociability, an Autism-Relevant Phenotype, in Mouse Models. The Anatomical Record. Oct. 2011;294(10):1713-25.

(56) References Cited

OTHER PUBLICATIONS

Fendt et al., TMT-Induced Autonomic and Behavioral Changes and the Neural Bases of its Processing. Neuroscience and Biobehavioral Reviews. 2005;29(8):1145-56.
Ferrero et al., The Secret Codes of Mammalian Scents. Wiley Interdiscip Rev Syst Biol Med. Jan.-Feb. 2010;2(1):23-33.
Geschwind, Advances in Autism. Annul Rev Med. 2009;60:367-80.
Geschwind, Autism: Many Genes Common Pathways. Cell. Oct. 31, 2008;135(3):391-5.
Greer et al., The Angelman Syndrome Protein Ube3A Regulates Synapse Development by Ubiquitinating Arc. Cell. Mar. 5, 2010;140(5):704-16.
Horev et al., Dosage-Dependent Phenotypes in Models of 16p11.2 Lesions Found in Autism. PNAS. Oct. 11, 2011;108(41):17076-81.
Jhuang et al., Automated Home-Cage Behavioural Phenotyping of Mice. Nature Communications. Sep. 7, 2010;1:68. doi:10.1038/ncomms1064.
Johnson et al., Composing Graphical Models with Neural Networks for Structures Representations and Fast Inference. 30th Conference on Neural Information Processing Systems (NIPS 2016). Barcelona, Spain. 2016. 9 pages.
Kimchi et al., A Functional Circuit Underlying Male Sexual Behavior in the Female Mouse Brain. Nature. Aug. 30, 2007; 448(7157):1009-14.
Kobayakawa et al., Innate Versus Learned Odour Processing in the Mouse Olfactory Bulb. Nature. Nov. 22, 2007;450(7169):503-8.
Lee et al., Circuit Mechanisms Underlying Motor Memory Formation in the Cerebellum. Neuron 86 Apr. 22, 2015; p. 529-40.
Mandiyan et al., Deficits in Sexual and Aggressive Behaviors in Cnga2 Mutant Mice. Nature Neuroscience. Dec. 2005;8(12):1660-2.
Mandiyan et al., Supplementary Materials from: Deficits in sexual and aggressive behaviors in Cnga mutant mice. Nature Neuroscience. Dec. 2005;8(12):1-7.
Mayya et al., Visual Tracking of Small Animals Based on Real-Time Level Set Method with Fast Infra-Red Thermographic Imaging. 2011 IEEE International Symposium on Robotic and Sensors Environments (ROSE). 2011:60-4.
Millot et al., Exploration Behaviour and Flight Response Toward a Stimulus in Three Sea Bass Strains (*Dicentrarchus labrax* L.). Applied Animal Behaviour Science. Jun. 2009;119(1-2):108-114.
Moy et al., Advances in Behavioral Genetics Mouse Models of Autism. Molecular Psychiatry. Jan. 2008;13(1):4-26.
Moy et al., Social Approach in Genetically Engineered Mouse Lines Relevant to Autism. Genes, Brain and Behavior. Mar. 2009;8(2):129-42.
Nestler et al., Animal Models of Neuropsychiatric Disorders. Nature Neuroscience. Oct. 2010;13(10):1161-9.
Ou-Yang, et al., An Infrared Range Camera-Based Approach for Three-Dimensional Locomotion Tracking and Pose Reconstruction in a Rodent. Journal of Neuroscience Methods. Sep. 30, 2011;201(1):116-23.
Peca et al., Shank3 Mutant Mice Displays Autistic-Like Behaviours and Striatal Dysfunction. Nature. Apr. 28, 2011;472(7344):437-42.
Penagarikano et al., Absence of CNTNAP2 leads to epilepsy neuronal migration abnormalities and core austism-related deficits. Cell. Sep. 30, 2011;147(1):235-46.
Radyushkin et al., Neuroligin-3-Deficient Mice: Model of a Monogenic Heritable Form of Autism with an Olfactory Deficit. Genes, Brain, and Behavior. Jun. 2009;8(4):416-25.
Rahmati et al., Cerebellar Potentiation and Learning a Whisker-Based Object Localization Task with a Time Response Window. The Journal of Neuroscience, Jan. 29, 2014, 34(5): 1949-62.
Restrepo et al., Emerging Views on the Distinct But Related Roles of the Main and Accessory Olfactory Systems in Responsiveness to Chemosensory Signals in Mice. Hormones and Behavior. Sep. 2004;46(3):247-56.
Ritzau-Jost et al., Ultrafast Action Potentials Mediate Kilohertz Signaling at a Central Synapse. Neuron. Oct. 1, 2014;84(1),152-163.
Ryan et al., Olfactory Cues are Sufficient to Elicit Social Approach Behaviors But Not Social Transmission of Food Preference of C57BL/6J Mice. Behavioral Brain Research. Nov. 21, 2008;193(2):235-42.
Shenoy et al., Cortical Control of Arm Movements: A Dynamical Systems Perspective. Annual Review of Neuroscience. Jul. 8, 2013;36:337-359.
Silverman et al., Behavioural Phenotyping Assaus for Mouse Models of Autism. Nature Reviews. Jul. 2010;11(7):490-502.
Spink et al., The Etho Vision Video Tracking System—a Tool for Behavioral Phenotyping of Transgenic Mice. Physiology & Behavior. Aug. 2001;73(5):731-44.
Steele et al., The Power of Automated High-Resolution Behavior Analysis Revealed By Its Application to Mouse Models of Huntington's and Prion Diseases. PNAS. Feb. 6, 2007;104(6):1983-8.
Stella et al., Uexkullian Umwelt as Science and as Ideology the Light and the Dark Side of a Concept. Theory Biosci. Jun. 2010;129(1):39-51.
Stern et al., Analyzing Animal Behavior Via Classifying Each Video Frame Using Convolutional Neural Networks. Scientific Reports. Sep. 23, 2015;5(14351):1-13.
Stowers et al., Olfactory Mechanisms of Stereotyped Behavior: on the Scent of Specialized Circuits. Current Opinion in Neurobiology. Jun. 2010;20(3):274-80.
Su et al., Olfactory Perception: Receptors, Cells, and Circuits. Cell. Oct. 2, 2009;139(1):45-59.
Sudhof et al., Neuroligins and Neuroexins Link Synaptic Function to Cognitive Disease. Nature. Oct. 16, 2008; 455(7215):903-11.
Verbeek et al., IAS Technical Report IAS-UVA-05-02: Rodent Behavior Annotation From Video. University of Amsterdam. 2005: 19 pages.
Walsh et al., Autism and Brain Development. Cell. Oct. 31, 2008; 135(3):396-400.
Wang et al., Are Your Pheromones Detected Through the Main Olfactory Epithelium. Mol Neurobiol. Jun. 2007; 35(3): 317-23.
Wang et al., Pheromone Detection in Male Mice Depends on Signaling Through the Type 3 Adenylyl Cyclase in the Main Olfactory Epithelium. The Journal of Neuroscience. Jul. 12, 2006; 26(28):7375-9.
Wiltschko et al., Mapping Sub-Second Structure in Mouse Behavior. Neuron. Dec. 16, 2015;88(6):1121-35.
Witt et al., Olfactory Behavioral Testing in the Adult Mouse. Journal of Visualized Experiments. Jan. 28, 2009;(23):949.
Xue, et al., Video-Based Animal Behavior Analysis From Multiple Cameras. 2006 IEEE International Conference on Multisensor Fusion and Integration for Intelligent systems. 2006: 335-340.
Yang et al., Simple Behavioral Assessment of Mouse Olfaction. Current Protocols in Neuroscience. Jul. 2009; 48(1):8.24.1-8.24.12.
Yildirim et al., TRPC2: Molecular Biology and Functional Importance. HEP. 2007;179:53-75.
Yu et al, Children Tantrum Behaviour Analysis Based on Kinect Sensor. 2011 Third Chinese Conference on Intelligent Visual Surveillance. 2011:49-52.
U.S. Appl. No. 17/241,863, filed Apr. 27, 2021, Datta et al.
Hong et al., Automated measurement of mouse social behaviors using depth sensing, video tracking, and machine learning. Proceedings of the National Academy of Sciences. Sep. 9, 2015; vol. 112(38), pp. E5351-E5360.

* cited by examiner

A)

B)

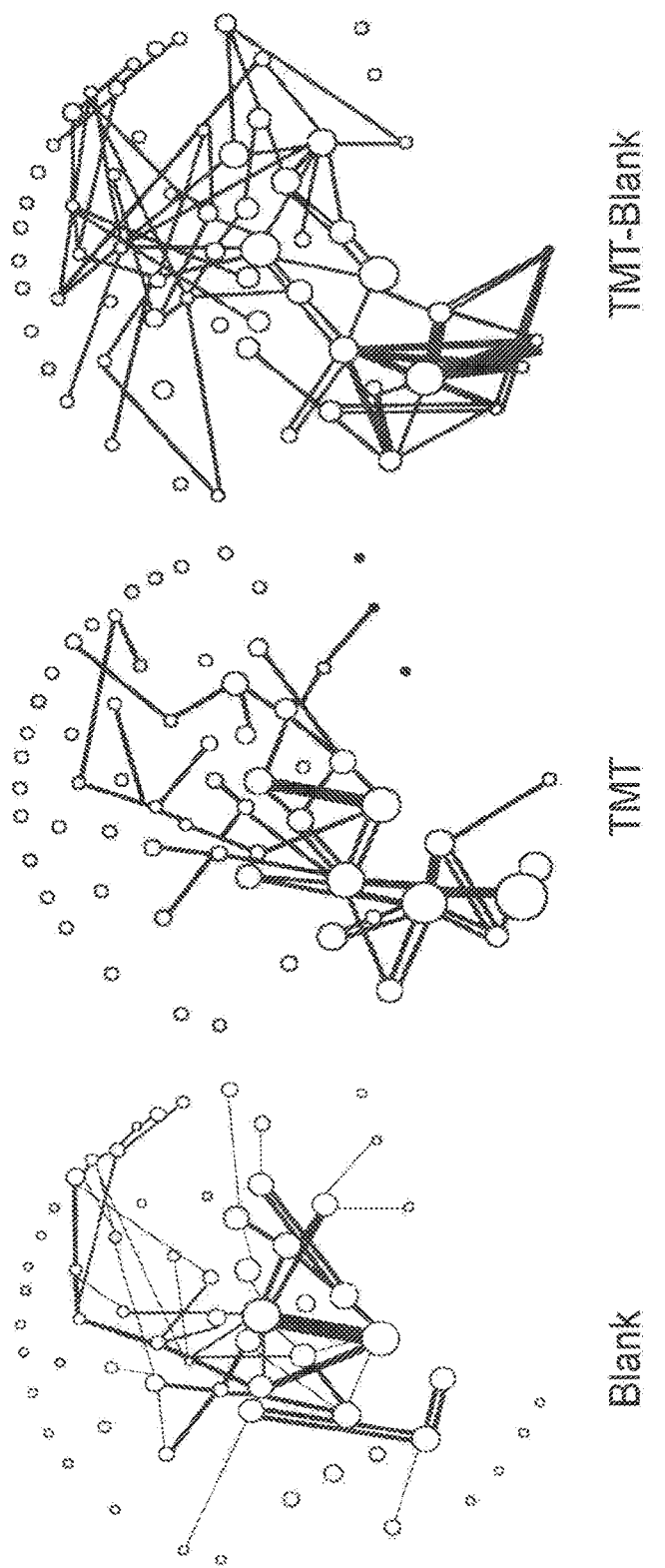

D)

E)

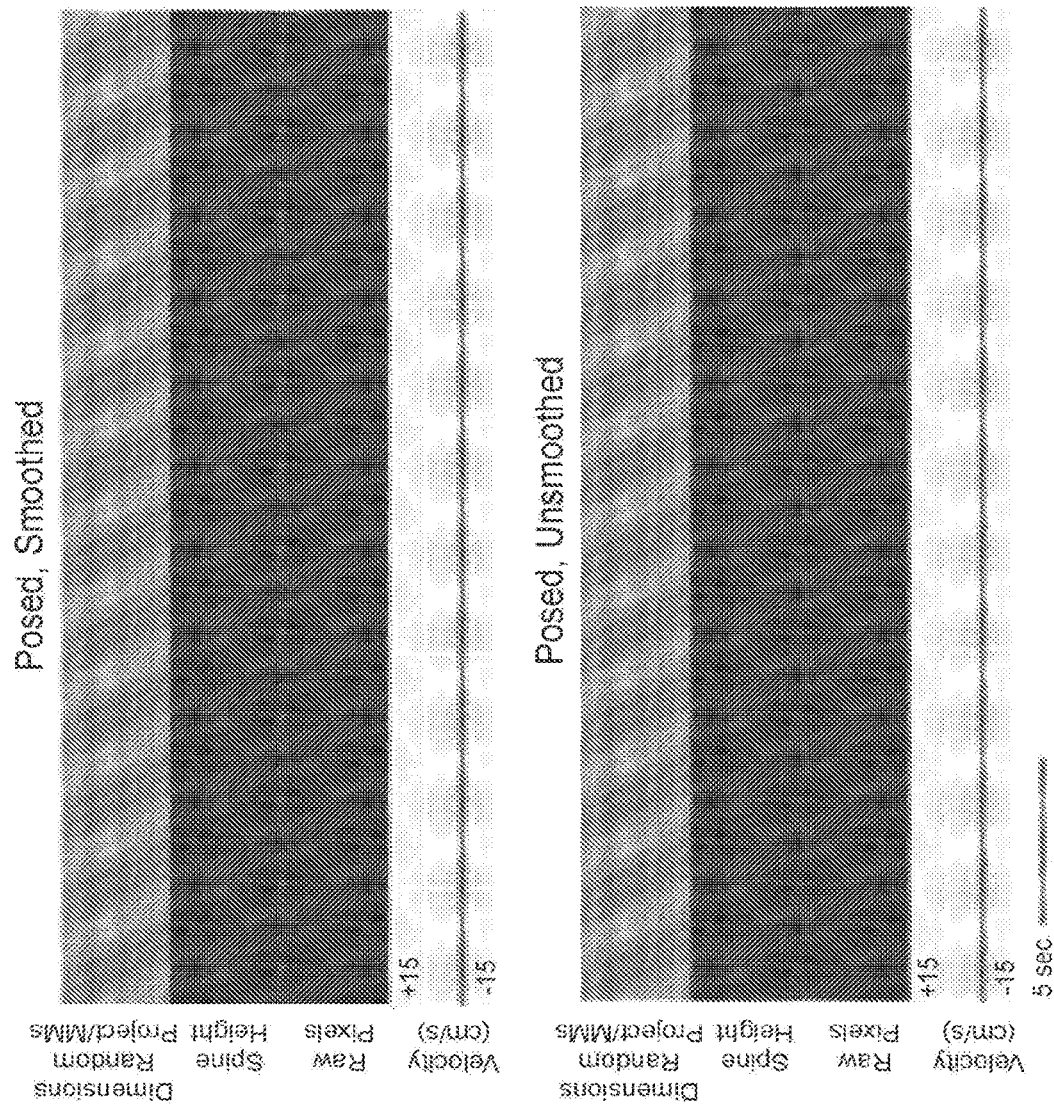
FIG. 13A"

AUTOMATICALLY CLASSIFYING ANIMAL BEHAVIOR

CROSS-REFERENCE TO RELATED APPLICATIONS

This application is a continuation under 35 U.S.C. § 120 of U.S. application Ser. No. 17/241,863 filed Apr. 27, 2021 which is a continuation under 35 U.S.C. § 120 of U.S. application Ser. No. 15/767,544 filed Apr. 11, 2018 which is a 35 U.S.C. § 371 National Phase Entry Application of International Application No. PCT/US2016/056471 filed Oct. 11, 2016, which designates the U.S. and claims benefit under 35 U.S.C. § 119(e) of U.S. Provisional Application No. 62/241,627, filed Oct. 14, 2015, the contents of each of which are incorporated herein by reference in their entireties.

STATEMENT REGARDING FEDERALLY SPONSORED RESEARCH

This invention was made with government support under OD007109 and DC011558 awarded by National Institutes of Health (NIH). The government has certain rights in this invention.

FIELD

The present invention is direct to system and methods for identifying and classifying animal behavior, human behavior or other behavioral metrics.

BACKGROUND

The following description includes information that may be useful in understanding the present invention. It is not an admission that any of the information provided herein is prior art or relevant to the presently claimed invention, or that any publication specifically or implicitly referenced is prior art.

The quantification of animal behavior is an essential first step in a range of biological studies, from drug discovery to understanding neurodegenerative disorders. It is usually performed by hand; a trained observer watches an animal behave, either live or on videotape, and records the timing of all interesting behaviors.

Behavioral data for a single experiment can include hundreds of mice, spanning hundreds of hours of video, necessitating a team of observers, which inevitably decreases the reliability and reproducibility of results. In addition, what constitutes an "interesting behavior" is essentially left to the human observer: while it is trivial for a human observer to assign an anthropomorphic designation to a particular behavior or series of behaviors (i.e., "rearing," "sniffing," "investigating," "walking," "freezing," "eating," and the like), there are almost certainly behavioral states generated by the mouse that are relevant to the mouse that defy simple human categorization.

In more advanced applications, video can be semi-automatically analyzed by a computer program. However, the brain generates behaviors that unfold smoothly over time and yet are composed of distinct patterns of motion. Individual sensory neurons that trigger action can perform behaviorally-relevant computations in as little as a millisecond, and neural populations that mediate behavior exhibit dynamics that evolve on timescales of 10 s to 100 s of milliseconds [1-8]. This fast neural activity interacts with slower neuromodulator systems to generate behaviors that are organized at multiple timescales simultaneously [9]. Ultimately understanding how neural circuits create complex behaviors—particularly spontaneous or innate behaviors expressed by freely-behaving animals—requires a clear framework for characterizing how behavior is organized at the timescales relevant to the nervous system.

SUMMARY

Although behaviors have been sculpted by evolution to enable animals to accomplish particular goals (such as finding food or a mate), it is not yet clear how these behaviors are organized over time, particularly at fast timescales. However, one powerful approach to characterizing the structure of behavior arises from ethology, which proposes that the brain builds coherent behaviors by expressing stereotyped modules of simpler action in specific sequences [10]. For example, both supervised and unsupervised classification approaches have identified potential behavioral modules expressed during exploration by C. elegans and by both larval and adult D. melanogaster [11-16]. These experiments have revealed an underlying structure to behavior in these organisms, which in turn has uncovered strategies used by invertebrate brains to adapt behavior to changes in the environment. In the case of C. elegans, navigation towards an olfactory cue is mediated at least in part by neural circuits that modulate the transition probabilities that connect behavioral modules into sequences over time; seemingly new sensory-driven behaviors (like positive chemotaxis) can therefore be generated by the worm nervous system through re-sequencing of a core set of behavioral modules [17-19]. Similar observations have been made for sensory-driven behaviors in fly larvae [11].

These insights into the underlying time-series structure of behavior arose from the ability to quantify morphological changes in worms and flies, and to use those data to identify behavioral modules [11-16]. However, it has been difficult to gain similar insight into the global organization of behavior in mammals. While innate exploratory, grooming, social approach, aggressive and reproductive behaviors in mice have all been divided by investigators into potential modules, this approach to breaking up mammalian behaviors into parts depends upon human-specified definitions for what constitutes a meaningful behavioral module (e.g. running, mating, fighting) [20-25] and are therefore largely bounded by human perception and intuition. Particularly, human perception has difficulty identifying modules spanning a short timescale.

Systematically describing the structure of behavior in animals—and understanding how the brain alters that structure to enable adaptation—requires addressing three key issues. First, it is not clear which features of behavior are important to measure when attempting to modularize mouse behavior. Although most current methods track two-dimensional parameters such as the position, velocity or shape of the top-down or lateral outline of the mouse [20,22-24,26-28], mice exhibit complex three-dimensional pose dynamics that are difficult to capture but which may afford important insights into the organization of behavior. Second, given that behavior evolves on several timescales in parallel, it is not clear how to objectively identify the relevant spatiotemporal scales at which to modularize behavior. Finally, effectively characterizing behavior requires accommodating the fact that behavior is both stereotyped (a prerequisite for modularity) and variable (an inescapable feature of noisy nervous and motor systems) [29].

This variability raises significant challenges for algorithms tasked with identifying the number and content of the behavioral modules that are expressed during a given experiment, or with assigning any given instance of an observed action to a particular behavioral module. Furthermore, identifying the spatiotemporal scales at which naturalistic behaviors are organized has been a defining challenge in ethology, and thus to date most efforts to explore the underlying structure of behavior have relied on ad hoc definitions of what constitutes a behavioral module, and have focused on specific behaviors rather than systematically considering behavior as a whole. It is not clear whether spontaneous behaviors exhibited by animals have a definable underlying structure that can be used to characterize action as it evolves over time.

Furthermore, existing computerized systems for classification of animal behavior match parameters describing the observed behavior against hand-annotated and curated parametric databases. Therefore, in both the manual and existing semi-automated cases, subjective evaluation of the animal's behavioral state is built into the system—a human observer must decide ahead of time what constitutes a particular behavior. This biases assessment of that behavior and limits the assessment to those particular behaviors the researcher can discriminate with human perception and is therefore limited, especially with respect to behaviors that occur on a short timescale. In addition, video acquisition systems deployed in these semi-supervised forms of behavioral analysis (nearly always acquiring data in two-dimensional) are only optimized for specific behaviors, thereby both limiting throughput and increasing wasted experimental effort through alignment errors.

Overview

Despite these challenges, the inventors have discovered systems and methods for automatically identifying and classifying behavior modules of animals by processing video recordings of the animals. In accordance with the principles of the invention, a monitoring method and system uses hardware and custom software that can classify animal behavior. Classification of an animal behavioral state is determined by quantitative measurement of animal posture in three-dimensions using a depth camera. In one embodiment, a three dimensional depth camera is used to obtain a stream of video images of the animal having both area and depth information. The background image (the empty experimental area) is then removed from each of the plurality of images to generate processed images having light and dark areas. The contours of the light areas in the plurality of processed images are found and parameters from both area and depth image information within the contours is extracted to form a plurality of multi-dimensional data points, each data point representing the posture of the animal at a specific time. The posture data points can then be clustered so that point clusters represent animal behaviors.

This data may then be fed into a model free algorithm, or fed into computation model to characterize the structure of naturalistic behavior. In some embodiments, the systems fit models for behavior using methods in Bayesian inference, which allows unsupervised identification of the optimal number and identity of behavioral modules from within a given dataset. Defining behavioral modules based upon structure in the three dimensional behavioral data itself—rather than using a priori definitions for what should constitute a measurable unit of action—identifies a previously-unexplored sub-second regularity that defines a timescale upon which behavior is organized, yields key information about the components and structure of behavior, offers insight into the nature of behavioral change, and enables objective discovery of subtle alterations in patterned action.

Example Application to Video of Mouse Exploring Open Field

In one example, the inventors measured how the shape of a mouse's body changes as it freely explores a circular open field. The inventors used depth sensors to capture three-dimensional ("3D") pose dynamics of the mouse, and then quantified how the mouse's pose changed over time by centering and aligning the image of the mouse along the inferred axis of its spine.

Plotting this three dimensional data over time revealed that mouse behavior is characterized by periods during which pose dynamics evolve slowly, punctuated by fast transitions that separate these periods; this pattern appears to break up the behavioral imaging data into blocks consisting of a small number of frames typically lasting from 200-900 ms. This suggests that mouse behavior may be organized at two distinct timescales, the first defined by the rate at which a mouse's pose can change within a given block, and the second defined by the transition rate between blocks.

Characterizing mouse behavior within these blocks—and determining how behavior might differ between blocks—requires first estimating the timescales at which these blocks are organized. In some embodiments, to identify approximate boundaries between blocks, the behavioral imaging data was submitted to a changepoint algorithm designed to detect abrupt changes in the structure of data over time. In one example, this method automatically identified potential boundaries between blocks, and revealed that the mean block duration was about 350 ms.

Additionally, the inventors performed autocorrelation and spectral analysis, which provided complementary information about the timescale of behavior. Temporal autocorrelation in the mouse's pose largely dissipated within 400 ms (tau=340±58 ms) and nearly all of the frequency content that differentiated behaving and dead mice concentrated between 1 and 6 Hz (measured by spectrum ratio, or Wiener filter, mean 3.75±0.56 Hz); these results suggest that most of the dynamism in the mouse's behavior occurs within 200-900 ms timescale.

Additionally, visual inspection of the block-by-block pattern of behavior exhibited by a mouse reveals that each block appears to encode a brief motif of behavior (e.g. a turn to the right or left, a dart, a pause, the first half of a rear) separated from the subsequent behavioral motif by a fast transition. Taken together, these findings reveal a previously-unappreciated sub-second organization to mouse behavior—during normal exploration mice express brief motifs of movement that appear to rapidly switch from one to another in series.

The finding that behavior is naturalistically broken up into brief motifs of motion indicates that each of these motifs is a behavioral module: a stereotyped and reused unit of behavior that the brain places into sequences to build more complex patterns of action. Next, systems and method are disclosed for identifying multiple examples of the same stereotyped sub-second motif of behavior.

Processing Algorithms and Methods for Identifying Modules in Video Data

To identify similar modules, mouse behavioral data may first be subject to principal components analysis (PCA) or other dimensionality reduction algorithm and the first two principal components may be plotted. Each block in the pose dynamics data corresponds to a continuous trajectory through PCA space; for example, an individual block associated with the mouse's spine being elevated corresponded to a specific sweep through PCA space. Scanning the behavioral data for matching motifs using a template matching method identified several additional examples of this sweep in different animals, suggesting that each of these PCA trajectories may represent individual instances in which a stereotyped behavioral module was reused.

Given this evidence for sub-second modularity, the inventors devised a series of computational models—each of which describes a different underlying structure for mouse behavior—trained these models on 3D behavioral imaging data, and determined which models predicted or identified the underlying structure of mouse behavior. Particularly, the inventors utilized computational inference methods (including Bayesian non-parametric approaches and Gibbs sampling) that are optimized to automatically identify structure within large datasets.

Each model differed in whether it considered behavior to be continuous or modular, in the possible contents of the modules, and in the transition structure that governed how modules were placed into sequence over time. To compare model performance, the models were tested to predict the contents and structure of real mouse behavioral data to which the models had not been exposed. Among the alternatives, the best quantitative predictions were made by a model that posits that mouse behavior is composed of modules (each capturing a brief motif of 3D body motion) that switch from one to another at the sub-second timescales identified by our model-free analysis of the pose dynamics data.

AR-HMM Model

One model represented each behavioral module as a vector autoregressive (AR) process capturing a stereotyped trajectory through PCA space. Additionally in that model, the switching dynamics between different modules were represented using a Hidden Markov Model (HMM). Together, this model is referred to herein as "AR-HMM."

In some embodiments, AR-HMM makes predictions about mouse behavior based upon its ability to discover (within training data) the set of behavioral modules and transition patterns that provide the most parsimonious explanation for the overall structure of mouse behavior as it evolves over time. Accordingly, a trained AR-HMM can be used to reveal the identity of behavioral modules and their transition structure from within a behavioral dataset, and thereby expose the underlying organization of mouse behavior. After training, the AR-HMM can assign every frame of the training behavioral data to one of the modules it has discovered, revealing when any given module is expressed by mice during a given experiment.

Consistent with the AR-HMM recognizing the inherent block structure in the 3D behavioral data, the module boundaries identified by the AR-HMM respected the inherent block structure embedded within the pose dynamics data. Furthermore, the model-identified module duration distribution was similar to the changepoints-identified block duration distribution; however, the module boundaries identified by the AR-HMM refined the approximate boundaries suggested by the changepoints analysis (78 percent of module boundaries were within 5 frames of a changepoint). Importantly, the ability of the AR-HMM to identify behavioral modules depended upon the inherent sub-second organization of mouse pose data, as shuffling the frames that make up the behavioral data in small chunks (i.e. <300 milliseconds) substantially degraded model performance, while shuffling the behavioral data in bigger chunks had little effect. These results demonstrate that the AR-HMM recognizes the inherent sub-second block structure of the behavioral data.

Additionally, specific behavioral modules identified by the AR-HMM encoded a set of distinct and reused motifs of motion. For instance, the PCA trajectories assigned by the model to one behavioral module traced similar paths through PCA space. Consistent with each of these trajectories encoding a similar motif of action, collating and inspecting the 3D movies associated with multiple data instances of this specific module confirmed that it encodes a stereotyped motif of behavior, one human observers would refer to as rearing. In contrast, data instances drawn from different behavioral modules traced distinct paths through PCA space. Furthermore, visual inspection of the 3D movies assigned to each of these modules demonstrated that each encodes a repeatedly used and coherent pattern of three-dimensional motion that can be distinguished and labeled with descriptors (e.g., "walk," "pause," and "low rear" modules).

To quantitatively and comprehensively assess the distinctiveness of each behavioral module identified by the AR-HMM, the inventors performed a cross-likelihood analysis, which revealed that the data instances associated with a given module are best assigned to that module, and not to any of the other behavioral modules in the parse. In contrast, the AR-HMM failed to identify any well-separated modules in a synthetic mouse behavioral dataset that lacks modularity, demonstrating that the discovered modularity within the real behavioral data is a feature of the dataset itself rather than being an artifact of the model. Furthermore, restarting the model training process from random starting points returns the same or a highly similar set of behavioral modules, consistent with the AR-HMM homing in on and identifying an intrinsic modular structure to the behavioral data. Together these data suggest that mouse behavior—when viewed through the lens of the AR-HMM— is fundamentally organized into distinct sub-second modules.

Additionally, if the AR-HMM identifies behavioral modules and transitions that make up mouse behavior, then synthetic behavioral data generated by a trained AR-HMM can provide a reasonable facsimile of real pose dynamics data. The AR-HMM appeared to capture the richness of mouse behavior, as synthetic behavioral data (in the form of spine dynamics, or a 3D movie of a behaving mouse) was qualitatively difficult to distinguish from behavioral data generated by an actual animal. Mouse pose dynamics data therefore appear to have an intrinsic structure organized on sub-second timescales that is well-parsed by the AR-HMM into defined modules; furthermore, optimal identification of these modules and effective prediction of the structure of behavior requires overt modeling of modularity and switching dynamics.

The systems and methods of the present invention can be applied to a variety of animal species, such as animals in animal models, humans in clinical trials, humans in need of diagnosis and/or treatment for a particular disease or disorder. Without limitations, these animals include mice, dogs, cats, cows, pigs, goats, sheep, rats, horses, guinea pigs, rabbits, reptiles, zebrafish, birds, fruit flies, worms, amphibians (e.g., frogs), chickens, non-human primates, and humans.

The systems and methods of the present invention can be used in a variety of applications including, but not limited to, drug screening, drug classification, genetic classification, disease study including early detection of the onset of a disease, toxicology research, side-effect study, learning and memory process study, anxiety study, and analysis in consumer behavior.

The systems and methods of the present invention are particularly useful for diseases that affect the behavior of a subject. These diseases include neurodegenerative diseases such as Parkinson's disease, Huntington's disease, Alzheimer's disease, and Amyotrophic lateral sclerosis, neurodevelopmental psychiatric disorders such as attention deficit hyperactivity disorder, autism, Down syndrome, Mendelsohnn's Syndrome, and Schizophrenia.

In some embodiments, the systems and methods of the present invention can be used to study how a known drug or test compound can alter the behavioral state of a subject. This can be done by comparing the behavioral representations obtained before and after the administration of the known drug or test compound to the subject. As used herein, the term "behavioral representation" refers to a set of sub-second behavioral modules and their transition statistics determined using the systems or methods of the invention. Without limitation, the behavioral representation can be in the form of a matrix, a table, or a heatmap.

In some embodiments, the systems and methods of the present invention can be used for drug classification. The systems and methods of the present invention can create a plurality of reference behavioral representations based on existing drugs and the diseases or disorders they treat, wherein each reference behavioral representation represents a class of drugs (e.g., antipsychotic drugs, antidepressants, stimulants, or depressants). A test behavioral representation can be compared to the plurality of reference behavioral representation, and if the test behavioral representation is similar to one of the plurality of reference behavioral representations, the test compound is determined to belong to the same class of drugs that is represented by said particular of reference behavioral representation. Without limitation, the test compound can be a small molecule, an antibody or an antigen-binding fragment thereof, a nucleic acid, a polypeptide, a peptide, a peptidomimetic, a polysaccharide, a monosaccharide, a lipid, a glycosaminoglycan, or combinations thereof.

In some embodiments, this may include a system for automatically classifying an animal's behavior as belonging to one class of drugs versus a list of alternatives. For instance, to develop the system, we may provide a training set of many mice under many different drug conditions, and build a linear or non-linear classifier to discover what combinations and ranges of features constitute membership in a particular drug class. This classifier may be then fixed as soon as training is completed, allowing us to apply it to previously unseen mice. Potential classifier algorithms may include logistic regression, support vector machine with linear basis kernel, support vector machine with radial basis function kernel, multi-layer perceptron, random forest classifier, or k-Nearest Neighbors classifier.

Similar to drug classification, in some embodiments, the systems and methods of the present invention can be used in gene-function classification.

In someone embodiments of drug screening, an existing drug that is known to treat a particular disease or disorder can be administered to a first test subject. The systems and methods of the present invention can then be used on the first test subject to obtain a reference behavioral representation, which includes a set of behavioral modules that can characterize the therapeutic effects of the drug on the first test subject. Subsequently, a test compound can be administered to a second test subject of the same animal type as the first test subject. The systems and methods of the present invention can then be used on the second test subject to obtain a test behavioral representation. If the test behavioral representation is found to be similar to the reference behavioral representation, the test compound is determined to be effective in treating the particular disease or disorder. If the test behavioral representation is found to not be similar to the reference behavioral representation, the test compound is determined to be ineffective in treating the particular disease or disorder. It should be noted that the first and second test subject can each be a group of test subjects, and the behavioral representation obtained can be an average behavioral representation.

Similar to drug screening, in some embodiments, the systems and methods of the present invention can be used in gene-therapy screening. Gene therapies can include delivery of a nucleic acid and gene knockout.

In some embodiments, the systems and methods of the present invention can be used in the study of disease or disorder. For example, the systems and methods of the invention can be used to discover new behavioral modules in subjects having a particular disease or disorder. For example, the systems and methods of the present invention can permit early diagnosis of a disease or disorder by identifying a reference behavioral representation in subjects having the disease or disorder or subjects that are in the process of developing the disease or disorder. If the reference behavioral representation or a significant portion thereof is also observed in a subject suspected of having the disease or disorder, the subject is diagnosed as having the disease or disorder. Thus early clinical interventions can be administered to the subject.

Additionally, in some embodiments, the systems and methods of the present invention can be used in the in the study of consumer behavior, for example, how a consumer responds to a scent (e.g., perfume). The systems and methods of the present invention can be used to identify a reference behavioral representation that represents positive reactions to the scent. In the presence of the scent, a person exhibiting the reference behavioral representation or a significant portion thereof is determined to be reacting positively to the scent. Reference behavioral representation that represents negative reactions to the scent can also be identified and used to gauge a person's reaction.

BRIEF DESCRIPTION OF THE DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

FIG. 6A. Modules identified by the AR-HMM sorted by usage (n=25 mice, 500 total minutes, data from circular open field). FIG. 6B. Hinton diagram of the observed bigram probabilities, depicting the probability that any pair of modules are observed as ordered pairs.

FIG. 6C. Module usage, sorted by context. Mean usages across animals depicted with dark lines, with bootstrap estimates depicted in fainter lines (n=100). Marked modules discussed in main text and shown in FIG. 6D: square=circular thigmotaxis, circle=rosette, diamond=square thigmotaxis, cross=square dart. FIG. 6D. Occupancy graph of mice in circular open field (left, n=25, 500 minutes total) indicating average spatial positions across all experiments. Occupancy graph depicting deployment of circular thigmotaxis module (middle, average orientation across the experiment indicated as arrow field) and circle-enriched rosette module (right, orientation of individual animals indicated with arrows). FIG. 6E. Occupancy graph of mice in square box (left, n=15, 300 minutes total) indicating cumulative spatial positions across all experiments. Occupancy graph depicting a square-enriched thigmophilic module (middle, average orientation across the experiment indicated as arrow field), and square-specific darting module (right, orientation of individual animals indicated with arrows).

FIGS. 8A-8E depict, in accordance with various embodiments of the present invention, depict graphs illustrating how odor avoidance alters transition probabilities. FIG. 8A. Occupancy plot of mice under control conditions (n=24, 480 total minutes) and exposed to the monomolecular fox-derived odorant trimethylthiazoline (TMT, 5% dilution in carrier DPG, n=15, 300 total minutes) in the lower left quadrant (arrow). FIG. 8B. Module usage plot sorted by "TMT-ness. Dark lines depict mean usages, bootstrap estimates depicted in fainter lines. Marked modules discussed in this specification and FIG. 8E: square=sniff in TMT quadrant, circle=freeze away from TMT. FIG. 8C, left and middle. Behavioral state maps for mice exploring a square box under control conditions (blank) and after TMT exposure, with modules depicted as nodes (usage proportional to the diameter of each node), and bigram transition probabilities depicted as directional edges. The two-dimensional layout is meant to minimize the overall distance between all connected nodes and is seeded by spectral clustering to emphasize neighborhood structure. FIG. 8C. Statemap depiction of the difference between blank and TMT. Usage differences are indicated by the newly sized colored circles (upregulation indicated in blue, downregulation indicated in red, blank usages indicated in black). Altered bigram probabilities are indicated in the same color code. FIG. 8D. Mountain plot depicting the joint probability of module expression and spatial position, plotted with respect to the TMT corner (X axis); note that the "bump" two-thirds of the way across the graph occurs due to the two corners equidistant from the odor source. FIG. 8E. Occupancy plot indicating spatial position in which mice after TMT exposure emit an investigatory sniffing module (left) or a pausing module.

FIG. 9A. Usage plot of modules exhibited by mice (n=6+/+, n=4+/−, n=5 −/−, open field assay, 20 minute trials), sorted by "mutant-ness". Mean usages across animals depicted with dark lines, with bootstrap estimates depicted in fainter lines. FIG. 9B. State map depiction of baseline OFA behavior for +/+ animals as in FIG. 4C (left); difference state maps as in FIG. 4C between the +/+ and +/− genotype (middle), and +/+ and −/− genotype (right). FIG. 9C. Illustration of the "waddle" module in which the hind limbs of the animal are elevated above the shoulder girdle, and the animal locomotes forward with a wobbly gait.

FIG. 10A. Mountain plot depicting the probability of expression of each behavioral module (each assigned a unique color on the Y axis) as a function of time (X axis), with two seconds of light stimulation initiated at time zero (each plot is the average of 50 trials). Note that because of the trial structure (in which mice were sequentially exposed to increasing light levels) modest variations in the baseline pattern of behavior are captured before light onset across conditions. Stars indicate two modules that are expressed during baseline conditions that are also upregulated at intermediate powers (11 mW) but not high powers (32 mW); cross indicates pausing module upregulated at light offset. FIG. 10B. Average position of example mice (with arrows indicating orientation over time) of the two modules induced under the highest stimulation conditions. Note that these plots are taken from one animal and representative of the complete dataset (n=4); because of variability in viral expression the threshold power required to elicit behavioral changes varied from animal to animal, but all expressed the spinning behaviors identified in FIG. 10A.

FIG. 11A depicts Imaging a mouse in the circular open field with a standard RGB camera (left) and a 3D depth camera (right, mouse height is color mapped, mm=mm above floor) captures the three-dimensional pose of the mouse. FIG. 11B depicts an arrow that indicates the inferred axis of the animal's spine; all mouse images are centered and aligned along this axis to enable quantitative measurements of pose dynamics over time during free behavior. Visualization of pose data reveals inherent block structure within 3D pose dynamics. Compression of preprocessed and spine-aligned data through the random projections technique reveals sporadic sharp transitions in the pose data as it evolves over time. Similar data structure was observed in the raw data and in the height of the spine of the animal as it behaves (upper panel, spine height at any given position is colormapped, mm=mm above floor). When the animal is rearing (as it is here at the beginning of the datastream), its cross-sectional profile with respect to the camera becomes smaller; when the animal is on all fours its profile becomes larger. FIG. 11C shows a changepoints analysis which identifies potential boundaries between these blocks (normalized probability of a changepoint indicated in the trace at the bottom of the behavioral data). Plotting the duration of each block as identified by the changepoints analysis reveals a block duration distribution (n=25, 500 total minutes imaging, mean=358 ms, SD 495 ms). Mean block duration values are plotted in black, with the duration distribution associated with each individual mouse plotted in gray. FIG. 11C, middle and right. Autocorrelation analysis reveals that the rate of decorrelation in the mouse's pose slows after about 400 milliseconds (left, mean plotted in dark blue, individual mouse autocorrelations plotted in light blue, tau=340±58 ms). Plotting the ratio in spectral power between a behaving and dead mouse (right, mean plotted in black, individual mice plotted in grey) reveals most behavioral frequency content is represented between 1 and 6 Hz (mean=3.75±0.56 hz);

FIG. 12A depicts how a projection of mouse pose data into Principal Components (PC) space (bottom) reveals that the individual blocks identified in the pose data encode reused trajectories. After subjecting mouse pose data to principal components analysis, the values of the first two PCs at each point in time were plotted in a two-dimensional graph (point density is colormapped). Tracing out the path associated with a block highlighted by changepoints analysis (top) identifies a trajectory through PC space (white). By searching through pose data using a template matching procedure, additional examples of this block were identified that encoded similar trajectories through PC space (time indicated as progression from blue to red), suggesting that the template block represented a reused motif of motion. FIG. 12B depicts modeling mouse pose data with the AR-HMM identifies individual behavioral modules. The AR-HMM parses the behavioral data into a limited set of identifiable modules (top—marked "labels", each module is uniquely color coded). Multiple data instances associated with a single behavioral module each take a stereotyped trajectory through PCA space (bottom left, trajectories in green); multiple trajectories define behavioral sequences (bottom center). Depicting the side-on view of the mouse (inferred from depth data, bottom right) reveals that each trajectory within a behavioral sequence encodes a different elemental action (time within the module is indicated as increasingly darker lines, from module start to end). FIG. 12C depicts isometric-view illustrations of the three-dimensional imaging data associated with walk, pause and low rear modules. FIG. 12D depicts cross-likelihood analysis depicting the probability that a data instance assigned to a particular module will be effectively modeled by another module. Cross-likelihoods were computed for the open field dataset, and the likelihood that any given data instance assigned to a particular module would be accurately modeled by a different module is heatmapped (units are vats, where enats is the likelihood ratio); note the high-likelihood diagonal, and the low likelihoods associated for all off-diagonal comparisons. Plotting the same metric on a model trained on synthetic data whose autocorrelation structure matches actual mouse data but which lacks any modularity reveals that the AR-HMM fails to identify modules in the absence of underlying modularity in the training data.

FIG. 13Ai-13Aii depict that a block structure is present in random projections data, spine data and raw pixel data derived from aligned mouse pose dynamics.

This changepoint ratio was not highly sensitive to K; a setting of 48 (at the observed maximum) was therefore chosen.

Figure 22:
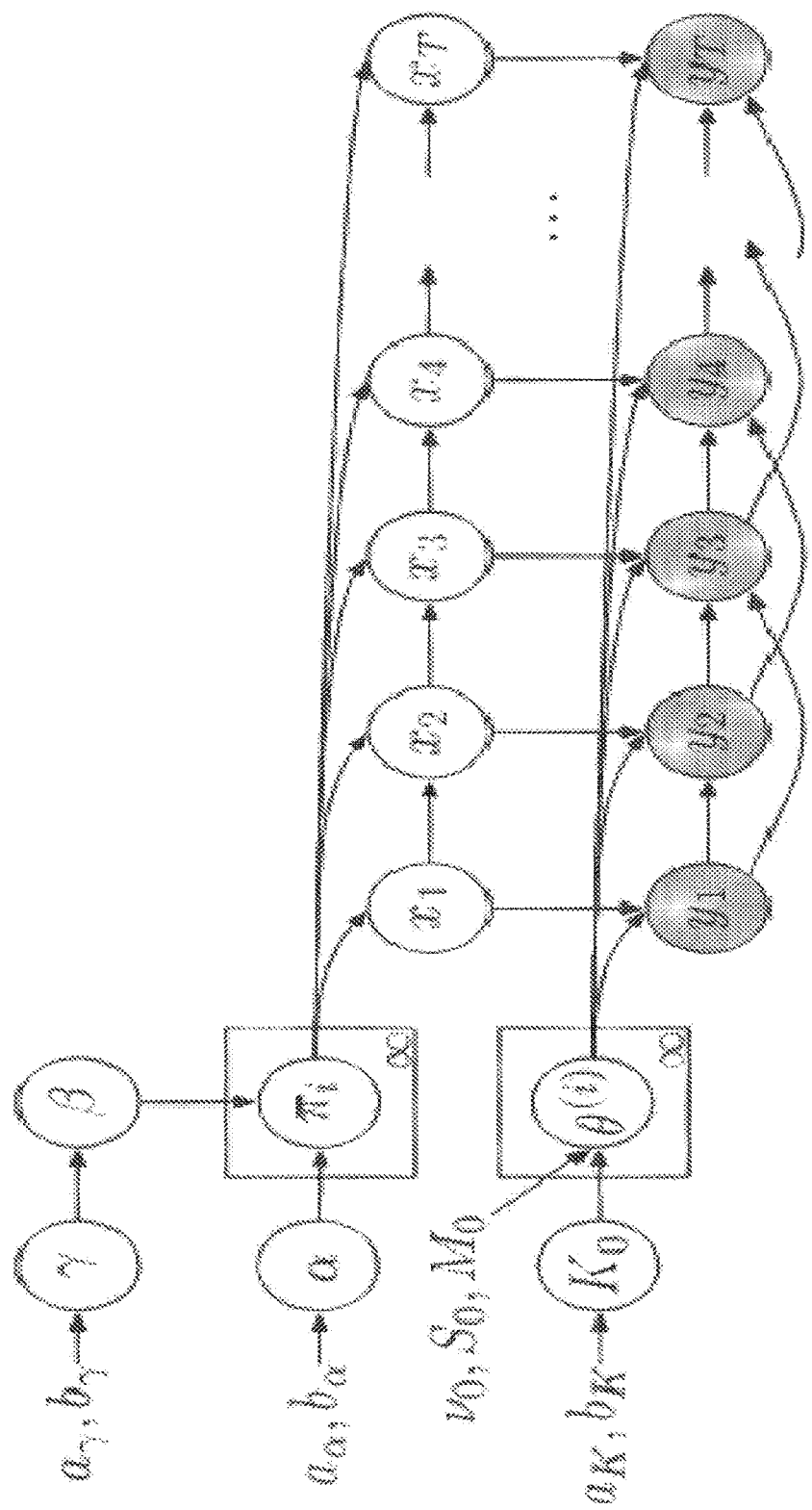

FIG. 22 depicts, in accordance with various embodiments of the present invention, a graphical model for the AR-HMM. The shaded nodes labeled y_t for time indices t=1, 2, . . . ,T represent the preprocessed 3D data sequence. Each such data node y_t has a corresponding state node x_t which assigns that data frame to a behavioral mode. The other nodes represent the parameters which govern the transitions between modes (i.e. the transition matrix m) and the autoregressive dynamical parameters for each mode (i.e. the set of parameters θ).

In the drawings, the same reference numbers and any acronyms identify elements or acts with the same or similar structure or functionality for ease of understanding and convenience. To easily identify the discussion of any particular element or act, the most significant digit or digits in a reference number refer to the Figure number in which that element is first introduced.

DETAILED DESCRIPTION

In some embodiments, properties such as dimensions, shapes, relative positions, and so forth, used to describe and claim certain embodiments of the invention are to be understood as being modified by the term "about."

Various examples of the invention will now be described. The following description provides specific details for a thorough understanding and enabling description of these examples. One skilled in the relevant art will understand, however, that the invention may be practiced without many of these details. Likewise, one skilled in the relevant art will also understand that the invention can include many other obvious features not described in detail herein. Additionally, some well-known structures or functions may not be shown or described in detail below, so as to avoid unnecessarily obscuring the relevant description.

The terminology used below is to be interpreted in its broadest reasonable manner, even though it is being used in conjunction with a detailed description of certain specific examples of the invention. Indeed, certain terms may even be emphasized below; however, any terminology intended to be interpreted in any restricted manner will be overtly and specifically defined as such in this Detailed Description section.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly while operations may be depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Overview

The inventors have discovered systems and methods for automatically and objectively identifying and classifying behavior modules of animals by processing video data of the animals. These systems may classify animal behavioral state by quantitative measurement, processing, and analysis of an animal posture or posture trajectory in three-dimensions using a depth camera. These system and methods obviate the need for a priori definition for what should constitute a measurable unit of action, thus making the classification of behavioral states objective and unsupervised.

In one aspect, the invention relates to a method for analyzing the motion of a subject to separate it into sub-second modules, the method comprising: (i) processing three dimensional video data that represent the motion of the subject using a computational model to partition the video data into at least one set of sub-second modules and at least one set of transition periods between the sub-second modules; and (ii) assigning the at least one set of sub-second modules to a category that represents a type of animal behavior.

Figure 1:
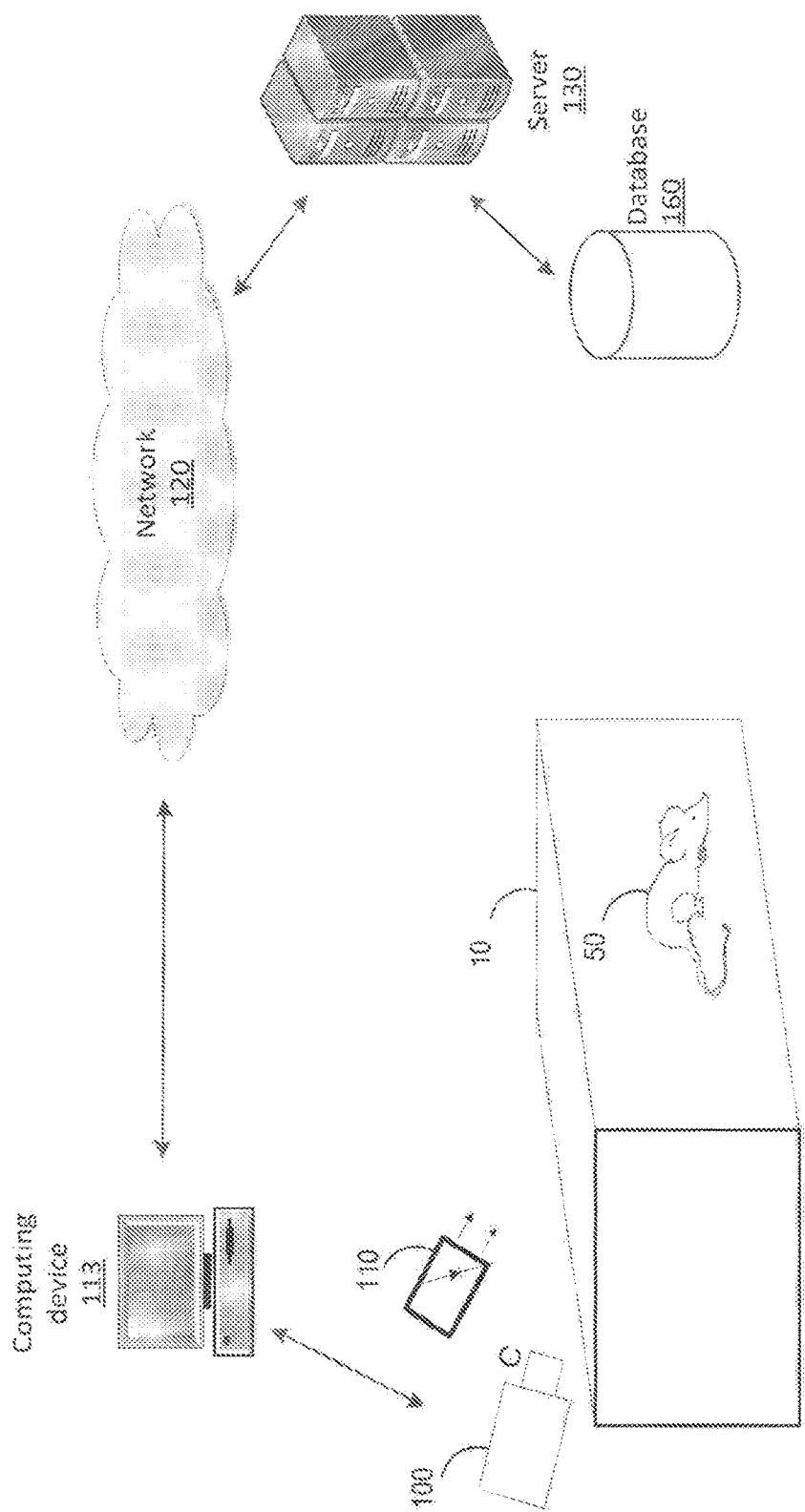
FIG. 1 depicts, in accordance with various embodiments of the present invention, a diagram of a system designed to capture video data of an animal.

FIG. 1 illustrates an embodiment of the process a system may utilize to automatically classify video frames or sets of frames into behavior modules. For instance, the system may include a video recorder 100 and tracking system 110. In some embodiments, video recorder 100 may be a 3D depth camera and the tracking system 110 may project structured infrared light into the experimental field 10. Infrared receivers on the tracking system may be able to determine the location of an object based on parallax. In some embodiments, the video recorder 100 may be connected to the tracking system 110 or in some embodiments they may be separate components.

The video recorder 100 may output data related to video images and or tracking data from the tracking system 110 to a computing device 113. In some embodiments, the computing device 113 will perform pre-processing of the data locally before sending over a network 120 to be analyzed by a server 130 and to be saved in a database 160. In other embodiments, the data may be processed, and fit locally on a computing device 113.

In one embodiment, a 3D depth camera 100 is used to obtain a stream of video images of the animal 50 having both area and depth information. The background image (the empty experimental area) is then removed from each of the plurality of images to generate processed images having light and dark areas. The contours of the light areas in the plurality of processed images can be found and parameters from both area and depth image information within the contours can then be extracted to form a plurality of multi-dimensional data points, each data point representing the posture of the animal at a specific time. The posture data points can then be clustered so that point clusters represent animal behaviors.

Then, the preprocessed depth-camera video data may be input into the various models in order to classify the video data into sub-second "modules" and transition periods that describe repeated units of behavior that are assembled together to form coherent behaviors observable by the human eye. The output of the models that classify the video data into modules may output several key parameters including: (1) the number of behavioral modules observed within a given set of experimental data (i.e. the number of states), (2) the parameters that describe the pattern of motion expressed by the mouse associated with any given module (i.e. state-specific autoregressive dynamical parameters), (3) the parameters that describe how often any particular module transitions to any other module (i.e. the state transition matrix), and (4) for each video frame an assignment of that frame to a behavioral module (i.e. a state sequence associated with each data sequence). In some embodiments, these latent variables were defined by a generative probabilistic process and were simultaneously estimated using Bayesian inference algorithms.

Camera Setup and Initialization

Various methods may be utilized to record and track video images of animals 50 (e.g., mice). In some embodiments, the video recorded may be recorded in three dimensions. Various apparatuses are available for this function, for instance the experiments disclosed herein utilized Microsoft's Kinect for Windows. In other embodiments, the following additional apparatuses may be utilized: (1) stereo-vision cameras (which may include groups of two or more two-dimensional cameras calibrated to produce a depth image, (2) time-of-flight depth cameras (e.g. CamCube, PrimeSense, Microsoft Kinect 2, structured illumination depth cameras (e.g. Microsoft Kinect 1), and x-ray video.

The video recorder 100 and tracking system 110 may project structured infrared light onto the imaging field 10, and compute the three-dimensional position of objects in the imaging field 10 upon parallax. The Microsoft Kinect for Windows has a minimum working distance (in Near Mode) of 0.5 meters; by quantitating the number of missing depth pixels within an imaged field, the optimal sensor positioned may be determined. For example, the inventors have discovered that the optimal sensor position for a Kinect is between 0.6 and 0.75 meters away from the experimental field depending on ambient light conditions and assay material.

Data Acquisition

Data output from the video recorder 100 and tracking system 110 may be received by and processed by a computing device 113 that processes the depth frames and saves them in a suitable format (e.g., binary or other format). In some embodiments, the data from the video recorder 100 and tracking system 110 may be directly output over a network 120 to a server 130, or may be temporarily buffered and/or sent over a USB or other connection to an associated computing device 113 that temporarily stores the data before sending over a network 120 to a centralized server 130 for further processing. In other embodiments, the data may be processed by an associated computer 113 without sending over a network 120.

For instance, in some embodiments, data output from a Kinect may be sent to a computer over a USB port utilizing custom Matlab or other software to interface the Kinect via the official Microsoft .NET API that retrieves depth frames at a rate of 30 frames per second and saves them in raw binary format (16-bit signed integers) to an external hard-drive or other storage device. Because USB3.0 has sufficient bandwidth to allow streaming of the data to an external hard-drive or computing device with storage in real-time. However, in some embodiments, a network may not have sufficient bandwidth to remotely stream the data in real time.

Data Pre-Processing

In some embodiments, after the raw images of the video data are saved and/or stored in a database or other memory, various pre-processing may take place to isolate the animal in the video data and orient the images of the animal along a common axis for further processing. In some embodiments, the orientation of the head may be utilized to orient the images in a common direction. In other embodiments, an inferred direction of the spine may be incorporated.

For instance, tracking the evolution of an imaged mouse's pose over time requires identifying the mouse within a given video sequence, segmenting the mouse from the background (in this case the apparatus the mouse is exploring), orienting the isolated image of the mouse along the axis of its spine, correcting the image for perspective distortions, and then compressing the image for processing by the model.

Isolating Video Data of the Animal

Figure 2A:
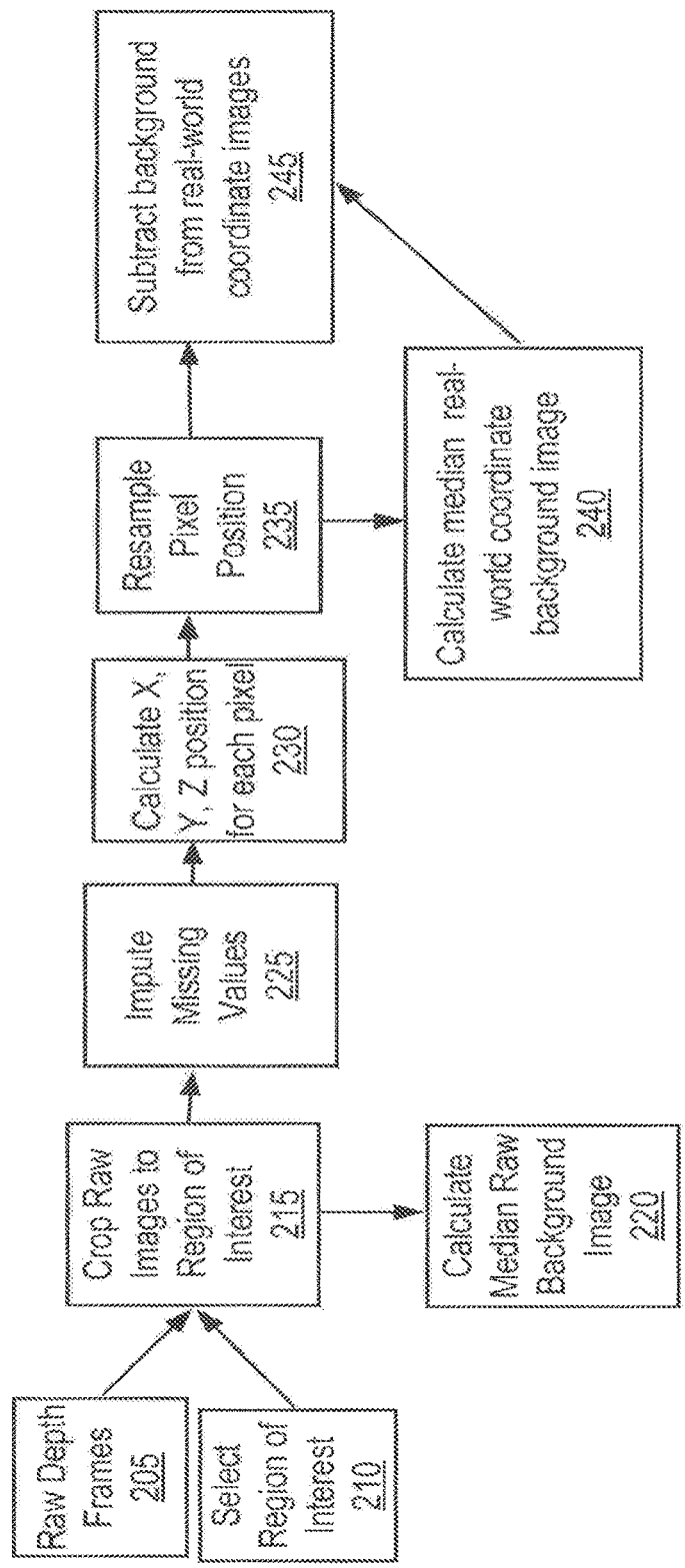
FIG. 2A depicts, in accordance with various embodiments of the present invention, a flow chart showing processing steps performed on video data.

FIG. 2A illustrates a process the system may perform for isolating a region of interest and subtracting background images to isolate the video data of the animal 50. First, to isolate the experimental arena in which the mouse is behaving, the system may first identify a region-of-interest (ROI) 210 for further analysis. In other embodiments, the region-of-interest 210 may include the entire field of view 10 of recorded video data. To isolate the region, one may manually trace along the outside edge of any imaged arena; pixels outside the ROI 210 may be set to zero to prevent spurious object detection. In other embodiments, the system may automatically define a ROI 210 using various methods. In some embodiments, the system may filter the raw imaging data with an iterative median filter, which is well suited to removing correlated noise from the sensor, for example, in a Kinect.

After selecting the region of interest 210, the raw images may be cropped to the region of interest 215. Then missing pixel values can be input 225, after which an X, Y, and Z position can be calculated 230 for each pixel, and the pixel position can be resampled. Accordingly, the images can be resampled onto real-world coordinates. Then, the system calculates the median real-world coordinate background image 240, and those can be subtracted from the real-world coordinate images 245.

To subtract the background image of the arena from the video data, various techniques may be performed, including for example, subtracting the median value of a portion of the video data for a set time period (e.g. 30 seconds). For instance, in some embodiments, the first 30 seconds of data from any imaging stream may be subtracted from all video frames and any spurious values less than zero may be reset to zero.

Figure 2B:
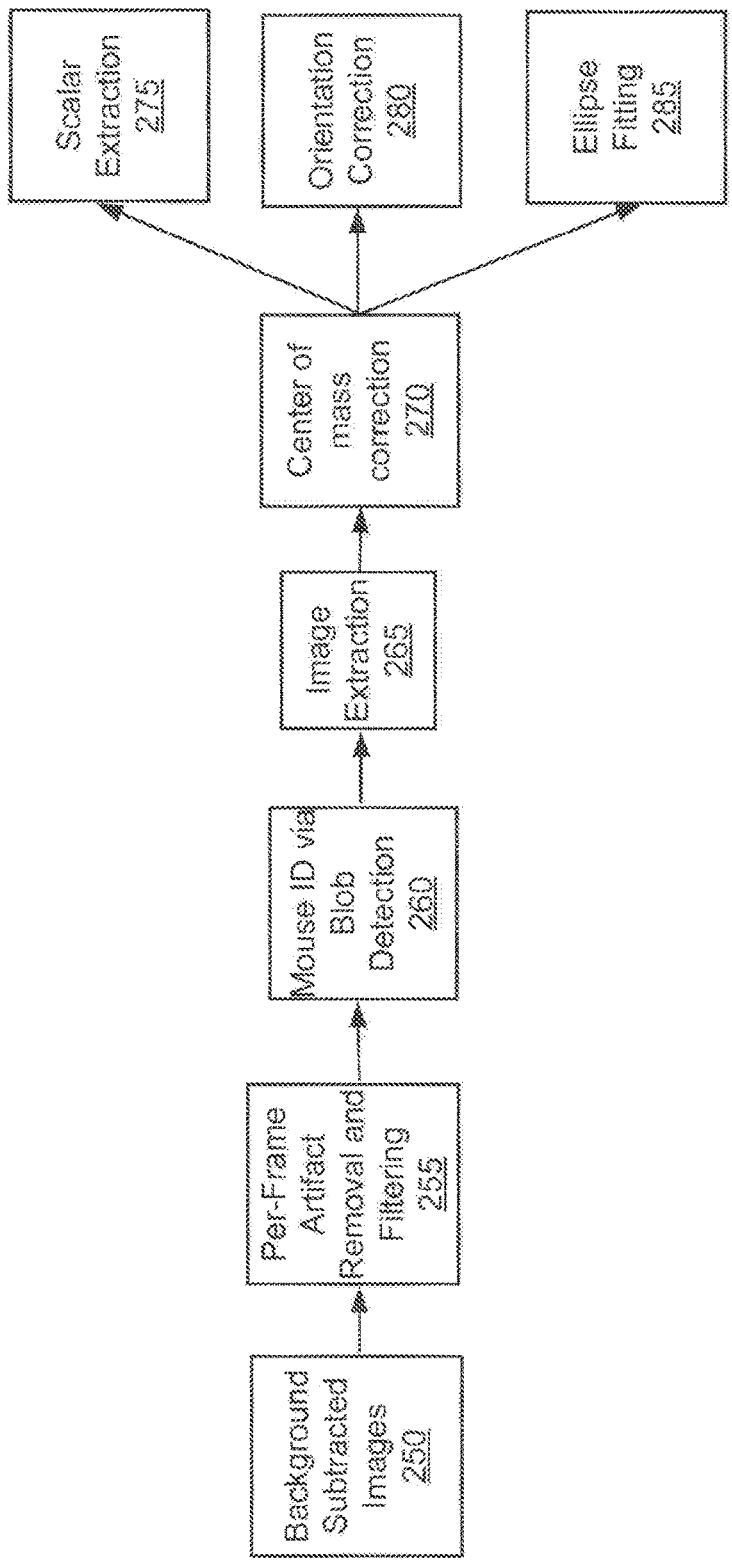
FIG. 2B depicts, in accordance with various embodiments of the present invention, a flow chart showing processing steps performed on video data.

To further ensure the analysis focuses on the animal, the system may binarize the image (or perform similar processes using thresholds) and eliminate any objects that did not survive a certain number of iterations of morphological opening. Accordingly, once this is finished, the system may perform the additional processing illustrated in FIG. 2B. Accordingly, the background subtracted images (mouse video data) 250 may be filtered and the artifacts may be removed 255. In some embodiments, this may involve iterative median filtering.

The animal in the image data may then be identified by defining it as the largest object within the arena that survived the subtraction and masking procedures, or by blob detection 260. Then, the image of the mouse may be extracted 265.

Identifying the Orientation of the Animal

The centroid of the animal (e.g. mouse) may then be identified 270 as the center-of-mass of the preprocessed image or by other suitable methods; an ellipse may then be fit to its contour 285 to detect its overall orientation. In order to properly orient the mouse 280, various machine learning algorithms may be trained (e.g. a random forest classifier) on a set of manually-oriented extracted mouse images. Given an image, the orientation algorithm then returns an output indicating whether the mouse's head is oriented correctly or not.

Once the position is identified, additional information may be extracted 275 from the video data including the centroid, head and tail positions of the animal, orientation, length, width, height, and each of their first derivatives with respect to time. Characterization of the animal's pose dynamics required correction of perspective distortion in the X and Y axes. This distortion may be corrected by first generating a tuple of (x,y,z) coordinates for each pixel in real-world coordinates, and then resampling those coordinates to fall on an even grid in the (x,y) plane using Delaunay triangulation.

Output to a Model Based or Model-Free Algorithm

Figure 3:
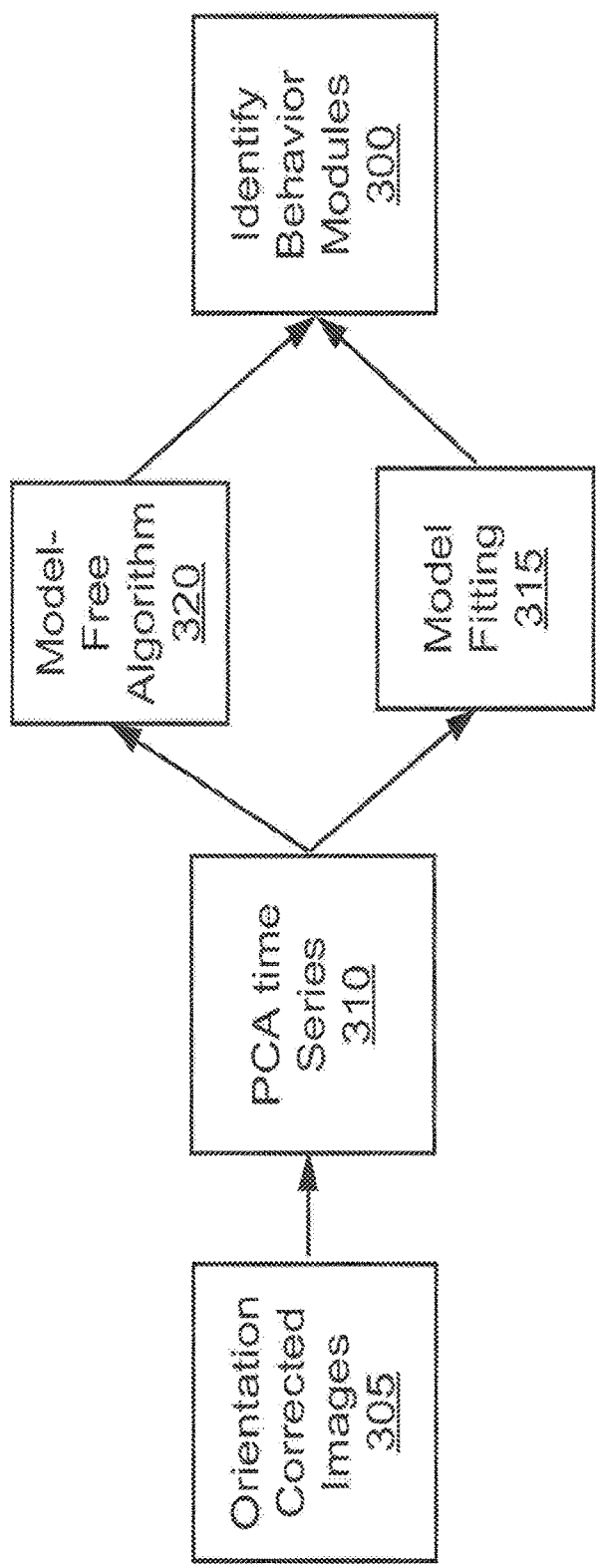
FIG. 3 depicts, in accordance with various embodiments of the present invention, a flow chart showing analysis performed on the video data output from the processing steps.

As illustrated in FIG. 3, the output of the orientation corrected images or frames in some embodiments will be to a principle component analysis time series 310 or other statistical methods for reducing data points. In some embodiments, the data will be run through a model fitting algorithm 315 such as the AR-HMM algorithm disclosed herein, or may be run through a model free algorithm 320 as disclosed in order to identify behavior modules 300 contained within the video data. Additionally, in some embodiments, the PCA time series will not be performed.

In embodiments with model-free algorithms 320, various combinations of algorithms can be utilized with the goal of isolating sub-second modules of behavior that have similar orientation profile and trajectories. Disclosed herein are some examples of these algorithms, however, additional algorithms could be envisioned that segment the data into behavior modules.

Reducing Dimensionality of Image

In some embodiments, both that include model-free algorithms 320 or the model fitting 315 algorithm, the information captured in each pixel often is either highly correlated (neighboring pixels) or uninformative (pixels on the border of the image that never represent the mouse's body). To both reduce redundant dimensions and make modeling computationally tractable, various techniques may be employed to dimensionally reduce each image. For example, a five-level wavelet decomposition may be performed, thereby transforming the image into a representation in which each dimension captured and pooled information at a single spatial scale; in this transformation, some dimensions may code explicitly for fine edges on the scale of a few millimeters, while others encoded broad changes over spatial scales of centimeters.

This wavelet decomposition however will expand the dimensionality of the image. In order to reduce this dimensionality, principal components analysis may then be applied to these vectors, in order to project the wavelet coefficients into ten dimensions, which the inventors have found still captures >95% of total variance. For instance, principle components may be built using a canonical dataset of 25 C57 BL/6 mice, aged 6 weeks, recorded for 20 minutes each, and all datasets were projected into this common pose space. Accordingly, the output of the PCA may then be input into the modeling algorithm for module identification.

In some embodiments, random projections technique may be utilized to reduce the dimensionality of the data. Random projections is an approach that produces new dimensions derived from an original signal, with dimensionality D_orig, by randomly weighting each original dimension, and then summing each dimension according to that weighting, producing a single number per data point. This procedure can be repeated several times, with new random weightings, to produce a set of "randomly projected" dimensions. The Johnson-Lindenstrauss lemma shows that distances between points in the original dataset with dimensionality D_orig is preserved in the randomly projected dimensions, D_proj, where D_proj<D_orig.

Model-Free Algorithms: Identifying Behavior Module Length

In some embodiments that have a model-free algorithm 320, in order to evaluate timescale over which an animal's behavior is self-similar—which reflects the rate at which an animal transitions from one pattern of motion to another—an autocorrelation analysis may be performed. Because some data smoothing is required to remove sensor-specific noise, computing the auto-correlogram as the statistical correlation between time-lagged versions of a signal will result in a declining auto-correlogram, even for an animal (e.g. mouse) that is posed in rigor mortis. Therefore, correlation distance between all 10 dimensions of the mouse's pose data may be utilized as the comparator between time-lagged versions of the time-series signal in question, resulting in a flat autocorrelation function of value ~1.0 for a dead animal, and a declining autocorrelation function for a behaving animal (e.g., mouse). The rate at which this auto-correlogram declines in a behavior mouse is a measure of a fundamental timescale of behavior, which may be characterized as a time-constant, tau, of an exponentially-decaying curve. Tau can be fitted using the Levenberg-Marquardt algorithm (non-linear least squares) using the SciPy optimization package.

In some embodiments, a power-spectral density (PSD) analysis may be performed on the mouse behavioral data to further analyze its time domain structure. For instance, a Wiener filter may be utilized to identify the time frequencies that must be boosted in the signal derived from a dead mouse in order to best match a behaving mouse. This can be implemented simply by taking the ratio of the PSD of a behaving mouse over the PSD of a dead mouse. In some embodiments, the PSD may be computed using the Welch periodogram method, which takes the average PSD over a sliding window across the entire signal.

Model-Free Algorithms: Locating Change Points for Transition Periods

In some embodiments where a model is not used to identify modules 320, various methods may be utilized to identify the changepoints for the transition periods. Plotting the random projections of the mouse depth image over time yields obvious striations, each a potential changepoint over time. To automate the identification of these changepoints, which represent potential boundaries between the block structure apparent in the random projections data, a simple changepoint identification technique called the filtered derivative algorithm may be utilized. For example, an algorithm can be employed that calculates the derivative of the per-frame unit-normalized random projections with a lag of k=4 frames. For each time point, for each dimension, an algorithm may determine whether the signal has crossed some threshold h=0.15 mm. Then, the binary changepoint indicator signal may be summed across each of D=300 random projection dimensions, and then the resulting 1D signal may be smoothed with a Gaussian filter with a kernel standard deviation of sigma=0.43 frames. Change points may then be identified as the local maxima of this smoothed 1D time-series. This procedure depends in part upon the specific values of the parameters k, h and sigma; for example, those values that maximize the number of changepoints in the behaving mouse while yielding no change points in a dead mouse may be utilized.

Model-Free Algorithms: Identifying Similar or Repeating Modules

In some embodiments, where data is being analyzed without a model 320, certain algorithms may be utilized to identify similar or repeated modules. Accordingly, a set of repeating modules may be identified as the vocabulary or syllables of the animal behavior. Therefore, to determine whether any reasonably long snippet of behavior (greater than just a few frames) was ever "repeated" (without reliance on a underlying model for behavior), the system may utilize a template matching procedure to identify similar trajectories through PCA space. To identify similar trajectories, for example, the systems and methods may calculate the Euclidean distance between some target snippet, the "template", and every possible snippet of equal length (often defined by the approximate block boundaries identified by changepoints analysis). Other similar methods could be employed for identifying modules, including other statistical based methods.

In some embodiments, the collection of modules that are similar would be selected as the most similar snippets, ignoring snippets discovered that were shifted less than 1 second from each other (to ensure we select behavioral snippets that occur distanced in time from each other, and also in separate mice).

Data Modeling

In other embodiments, systems and methods may be employed that identify behavior modules in video data utilizing data models 315. For instance, a data model may implement the well-established paradigm of generative probabilistic modeling, which is often used to model complex dynamical processes. This class of models is generative in the sense that it describes a process by which observed data can be synthetically generated by the model itself, and they are probabilistic because that process is defined mathematically in terms of sampling from probability distributions. In addition, by fitting an interpretable model to data, the data were 'parsed' in a manner that revealed the latent variable structure that the model posits gave rise to the data (including parameters describing the number and identities of the states as well as parameters describing the transitions between the states).

In some embodiments, the model 315 may be expressed utilizing a Bayesian framework. The Bayesian framework provides a natural way to express hierarchical models for the organization of behavior, priors or regularizers that reflect known or observed constraints on the patterns of motion within the 3D dataset, and a coherent representation of uncertainty. This framework also provides significant and well-established computational machinery for inferring key parameters of any model. Within the Bayesian framework, for a particular model structure (e.g. the spatiotemporal nature of the states and their possible transitions) and prior distributions on the latent variables, the data fixes a posterior distribution over the latent variables.

Below, the model-based methods used to characterize behavior are defined in two steps: first, a mathematical definition of the generative model and priors used, and second, a description of the inference algorithms.

Example Model for Identifying Behavior Modules— AR-HMM

In some embodiments, systems may utilize a discrete-time hidden Markov model 315 (HMM) to identify behavior modules. HMMs encompass a range of stochastic processes for modeling sequential and time series data. The HMM model posits that at each point in time (e.g. for every frame of imaging data), the mouse is within a discrete state (Markov state) that can be given a label. Each Markov state represents a brief three-dimensional motif of motion the animal undertakes while within that state. Because observed three-dimensional behavior of mice appears to depend upon the specific pattern of motion the animal expressed in the immediate past, ideally each Markov state would predict the mouse's future behavior based upon its immediate past pose dynamics. Each Markov state is therefore composed of both a latent discrete component, which identifies the behavioral mode of the animal, and a number of lags of the observation sequence, which are used to predict the short-timescale behavior of the animal based on the behavioral mode. This model structure is often called a switching vector-autoregressive (SVAR) model or autoregressive HMM (AR-HMM).

Figure 4:
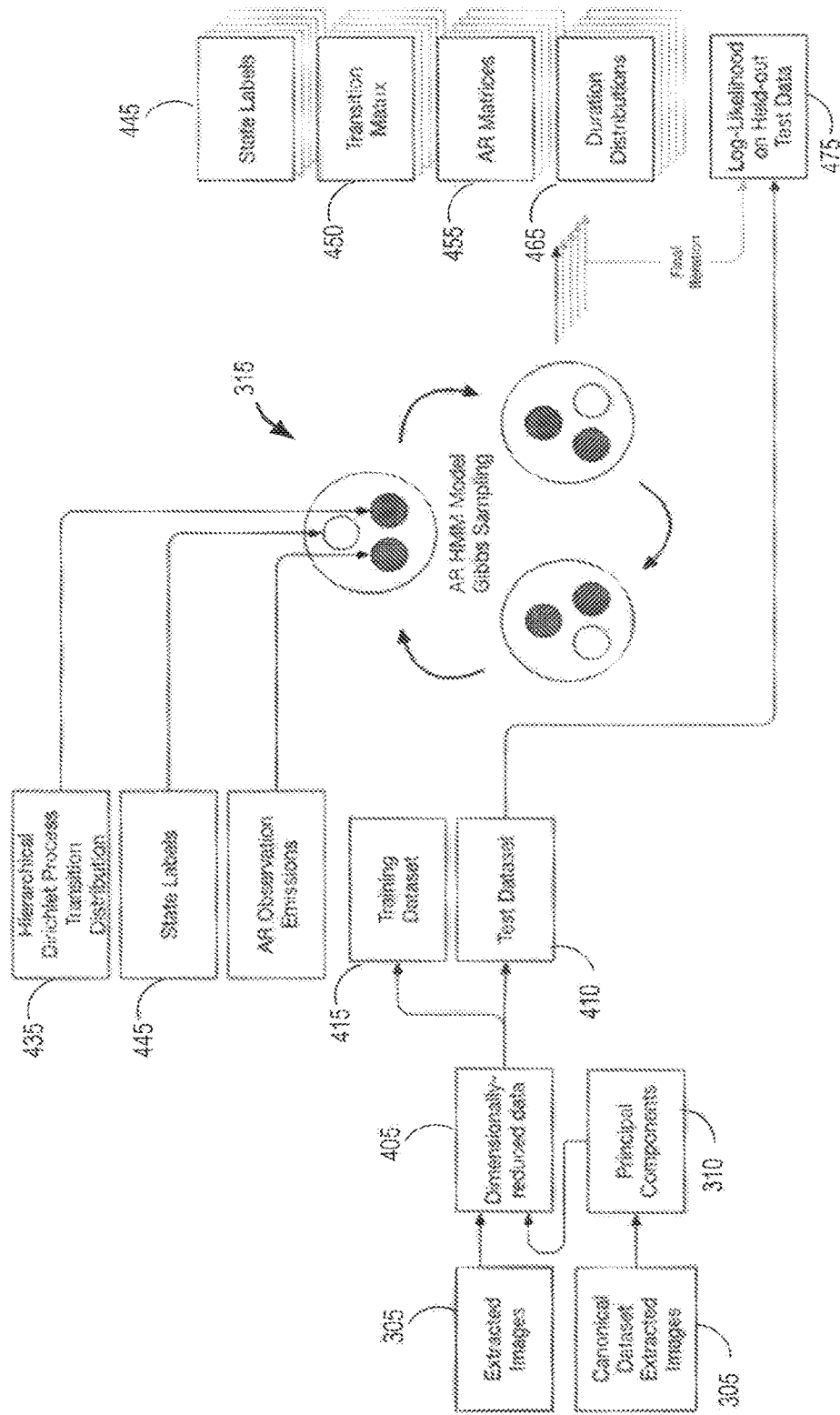
FIG. 4 depicts, in accordance with various embodiments of the present invention, a flow chart showing the implementation of an AR-HMM algorithm.

FIG. 4 provides an example of how an AR-HMM algorithm can convert input data (spine aligned depth imaging data 305 that has been dimensionally reduced 405 using PCA 310) into a fit model that describes the number of behavioral modules and the trajectories they encode through PCA space, the module-specific duration distributions that govern how long any trajectory within a given module lasts, and the transition matrix that describes how these individual modules interconnect over time.

In addition, the AR-HMM can be configured to assign a label to every frame of the training data associating it with a given behavioral module. After pre-processing and dimensional reduction 405, imaging data is broken into training 415 and test sets 410. The training set 415 is then submitted to the AR-HMM 315. After randomly initializing the parameters of the model 315 (which here refers to the autoregressive parameters that describe each module's trajectory through PCA space, the transition matrix describing the probabilities that governs temporal interconnections between modules, the duration distribution parameters that describe how long any instance of a given module is likely to last, and the labels assigned to each frame of imaging data associating that frame with a particular module) the AR-HMM attempts to fit the model 315 by varying one parameter while holding the others constant. The AR-HMM alternates between two main updates: the algorithm 315 first attempts to segment the imaging data into modules given a fixed set of transition statistics and a fixed description of the AR parameters that describe any given module, and then the algorithm switches to fixing the segmentation and updating the transition matrix and the AR parameters 455. The AR-HMM 315 uses a similar approach to assigning any given frame of imaging data to a given module. It first computes the probability of that a given module is the "correct" module, which is proportional to a measure of how well the state's corresponding autoregressive parameters 455 describe the data at that time index and how well the resulting state transitions agree with the transition matrix 450.

In the second step, the AR-HMM 315 varies the autoregressive parameters 455 and transition parameters 450 to better fit the assigned data, thus updating the each of the behavioral modules and the model of the transitions among modes. The product of this process are the parameters described 455, the quality of these parameters in terms of describing behavior are then evaluated using likelihood measurements of the data that was held-out from training 475.

By identifying the discrete latent states 445 associated with 3D pose sequence data, an HMM model 315 can identify segments of data that exhibit similar short-timescale motion dynamics and explain such segments in terms of reused autoregressive parameters. For each observation sequence there is an unobserved state sequence: if the discrete state at time index t is $x\_t=i$, then the probability that the discrete state $x\_(t+1)$ takes on value j is a deterministic function of i and j and is independent of all previous states. Symbolically, $$P(x_{t+1}|x_t,x_{t-1},x_{t-2},\ldots,x_1)=P(x_{t+1}|x_t)$$

$$P(x_{t+1}=j|x_t=i)=\pi_{ij}$$

where $\pi$ is a transition matrix 450 in which the (i,j) element is the probability of transitioning from state i to state j. In some embodiments, the discrete state's dynamics may be fully parameterized by the transition matrix, which is considered here not to change with time. One of the tasks of the inference algorithm (described below) was to infer probable values for the discrete state sequences and the transition matrix governing their deployment, thus inferring a sequence of reused behavioral modules and transition patterns that govern how these modules are connected over time.

Given a discrete state sequence, a corresponding 3D pose data sequence can be modeled as a conditionally vector autoregressive (VAR) process. Each state-specific vector autoregression can capture short-timescale motion dynamics particular to the corresponding discrete state; in other words, each behavioral module can be modeled as its own autoregressive process. More precisely, given the discrete state $x\_t$ of the system at any time index t, the value of the observed data vector at that time index $y\_t$ is distributed according to a state-specific noisy regression on K previous values of the observation sequence, $y\_(t-1), \ldots, y\_(t-K)$. The inference algorithm may also be tasked with inferring the most probable values for each state's autoregressive dynamical parameters as well as the number of lags used in the dynamics.

In some embodiments, these switching autoregressive dynamics defined the core of the AR-HMM. However, because different animal populations or experimental conditions are expected to give rise to differences in behavior, when considering two or more such experimental conditions models may be built hierarchically: different experimental conditions may be allowed to share the same library of state-specific VAR dynamics but learned their own transition patterns as well as any unique VAR dynamical modes. This simple extension allows a model to reveal changes in the parameters due to changes in the experiment. Furthermore, the compositional Bayesian inference algorithms employed immediately extends such hierarchical models.

To employ Bayesian inference methods, unknown quantities, including the transition matrix 450 and the autoregressive parameters 455 that describe each state 445, can be treated with a uniform representation as latent random variables. In particular, weak prior distributions 465 can be placed on these quantities and their posterior distributions 465 after conditioning on observed 3D imaging data were investigated. For the autoregressive parameters, a prior that included a Lasso-like penalty can be used to encourage uninformative lag indices to have their corresponding regression matrix coefficients tend to zero.

For the transition matrix 450, a hierarchical Dirichlet process 435 prior can used, to regularize the number of discrete latent states 445. In addition, the transition matrix 450 prior also included a sticky bias, which is a single nonnegative number that controlled the tendency of the discrete states to self-transition. Because this parameter controls the timescale of the inferred switching dynamics, this parameter can be set such that the output of the model inference algorithms matches (as closely as possible) the model-free duration distribution determined by a change-point analysis as disclosed herein (or other method of identifying the module length) and the autocorrelogram generated from the preprocessed and unmodeled 3D pose data. In some embodiments, this parameter can be tuned—for example to define the prior over the timescale of behavior.

In some embodiments, simpler models can be used than the AR-HMM model by removing certain portions of the model structure. For instance, removing the discrete switching dynamics captured in the transition matrix and replacing them with a mixture model may generate an alternative model in which the distribution over each discrete state does not depend on its previous state. This would be the case if animals had a set of behavioral modules from which to choose, and the likelihoods of expressing any given one of them did not depend on the order in which they appear. This simplification resulted in the autoregressive mixture model (AR-MM).

Alternatively, replacing the conditionally autoregressive dynamics with simple state-specific Gaussian emissions results in a Gaussian-emission HMM (G-HMM); this model explores the hypothesis that each behavioral module is best described by a simple pose, rather than being a dynamical trajectory. Applying both simplifications yields a Gaussian mixture model (G-MM), in which behavior is simply a sequence of poses over time in which the probability of expressing any given pose does not depend on the prior pose. Removing the switching dynamics yields a pure autoregressive (AR) or linear dynamical system (LDS) model, in which behavior is described as a trajectory through pose space without any reused discrete behavioral modules at all.

Analysis of Behavior Modules

In some embodiments, systems may provide the ability to provide an indication of the relationship between behavior modules, describe the most frequently used behavior modules, or perform other useful analysis of behavior modules.

For example, in order to represent the grammatical relationship between behavioral syllables, the probability (e.g. bigram) that two syllables were found occurring one after the other (a "bigram" of modules) can be calculated as a fraction of all observed bigrams. In some embodiments, to calculate this value for each pair (i,j) of modules, for example, a square n×n matrix, A, may be utilized where n is the number of total modules in the label sequence. Then, the systems and methods may scan through the label sequences that were saved at the last iteration of Gibbs sampling, incrementing the entry A[i,j] for every time the system identifies a syllable i directly preceding a syllable j. At the end of the label sequence, the system may divide by the number of total bigrams observed.

In order to visually organize those modules that were specifically up-regulated or selectively expressed as a result of a manipulation, the system may assign a selectivity index to each module. For example, where p(condition) indicates the percent usage of a module in a condition, the system may sort modules in the circular open field versus square box comparison by (p(circle)-p(square)/(p(circle)+p(square))). In the comparison between blank odor and fox odor (TMT), the system may sort modules by (p(tmt)−p(blank))/(p(tmt)+p(blank)).

Statemap Visualizations

The system may also output the syllable bigram probabilities and syllable usages on n syllables on a graph G=(V, E) in which each node i∈V={1,2, . . . , n} corresponds to syllable i and each directed edge (i,j)∈E={1,2, . . . , n}$^2$\{(i,i):i∈V} corresponds to a bigram. The graph may be output as a set of circular nodes and directed arcs so that the size of each node is proportional to the corresponding syllable's usage and the width and opacity of each arc is proportional to the corresponding bigram's probability within a minimum and maximum range depicted in the figure legends. To lay out each graph in a reproducible non-(pseudo-)random way (up to global rotation of the figure), the system may initialize the position of the nodes using the spectral layout algorithm and fine-tuned node positions using the Fructherman-Reingold iterative force-directed layout algorithm; we used both algorithms can be used as implemented in the NetworkX software package.

Overview of Main Inference Algorithms

In some embodiments, inference algorithms may be applied to the models 315 to estimate the parameters. For example, an approximate Bayesian inference can be performed using Gibbs sampling, a Markov Chain Monte Carlo (MCMC) inference algorithm. In the MCMC paradigm, the inference algorithm constructs approximate samples from the posterior distribution of interest, and these samples are used to compute averages or as a proxy for posterior modes. The sequence of samples produced by the algorithm dwells in regions of high posterior probability while escaping regions of low posterior probability or bad local optima. In the main AR-HMM model, the latent variables of interest include the vector autoregressive parameters, the hidden discrete state sequence, and the transition matrix (e.g. the autoregressive parameters that define the pose dynamics within any given behavioral module, the sequence of the modules, and the transition probabilities between any given module and any other module). Applying the MCMC inference algorithm to 3D imaging data generate a set of samples of these latent variables for the AR-HMM.

The Gibbs sampling algorithm has a natural alternating structure, directly analogous to the alternating structure of expectation-maximization (EM) and variational mean field algorithms. Applied to the AR-HMM, after initialization to a random sample from the prior, the algorithm can be alternated between two main updates: first, the algorithm can resample the hidden discrete state sequences given the transition matrix and autoregressive parameters, and second, the algorithm can resample the parameters given the hidden states.

In other words, the algorithm 315 first attempts to segment the imaging data into modules 300 given a fixed set of transition statistics and a fixed description of the AR parameters that describe any given module, and then the algorithm switches to fixing the segmentation and updating the transition matrix 450 and the AR parameters 455. To assign each of the 3D pose video frames to one of the behavioral modes 300 in the first step of this process, the state label 445 for a particular time index can be sampled randomly from the set of possible discrete states, where the probability of sampling a given state can be proportional to a measure of how well the state's corresponding autoregressive parameters described the data at that time index and how well the resulting state transitions agree with the transition matrix 450. In the second step, given the assignment of data subsequences to states, the autoregressive parameters and transition parameters can be resampled to fit the assigned data, thus updating the dynamical model of each of the behavioral modes and the model of the transitions among modes. The procedure implemented by the Gibbs sampling algorithm can be noisy, enabling the algorithm to escape local maxima that may prevent the algorithm from effectively exploring parameter space.

EXAMPLES

Below are disclosed examples of the specific implementations of the models described herein for performing the disclosed examples. Variations of these models may be implemented to identify behavior models.

Prior on the Transition Matrix

A sticky HDP prior was placed on the transition matrix it with concentration parameters $\alpha, \gamma > 0$ and sticky parameter $K > 0$ $$\rho_j \overset{iid}{\sim} \text{Beta}(1, \gamma)$$

$$\beta_i = (1 - \rho_i) \prod_{j<i} \rho_j$$

$$\pi_i \overset{iid}{\sim} DP(\alpha\beta + \kappa\delta_i)$$

$$i = 1, 2, \ldots$$

where $\delta_{ij}$ is 1 when i=j and is 0 otherwise and $\pi$ denotes the ith row of $\pi$. Gamma priors are placed on $\alpha$ and $\gamma$, setting $\alpha \sim \text{Gamma}(1,1/100)$ and $\gamma \sim \text{Gamma}(1,1/100)$. Generation of the discrete state sequence Given the transition matrix, the prior on a discrete state sequence x was $$X_t \sim \pi_{x_{t-1}} t=2,3,\ldots,T$$

where $x_1$ is generated by the stationary distribution under $\pi$.

Prior on the Autoregressive Parameters

The autoregressive parameters $\theta = \{\theta^{(i)}\}_{i=1}^{\infty} = \{A^{(i)}, b^{(i)}, \Sigma^{(i)}\}$ for each state i=1,2, ... were sampled from a Matrix Normal Inverse-Wishart prior:

$$(A,b), \Sigma \sim \text{MNIW}(\nu_0, S_0, M_0, K_0)$$

or equivalently $$\Sigma \sim \text{InvWishart}(\nu_0, S_0)$$

$$\text{vec}((A, b)) \sim \text{Normal}\bigl(\text{vec}(M_0), \Sigma \otimes K_0\bigr)$$

where $\otimes$ denotes a Kronecker product and (A, b) denotes the matrix formed by appending b to A as a column. In addition, a block ARD prior on $K_0$ is used to encourage uninformative lags to be shrunk to zero:

$$K_0 = \text{diag}(k_1, \ldots, k_{KD})$$

$$k_i \overset{iid}{\sim} \text{InvGamma}(1/25, 1/25).$$

Generation of the 3D Pose Sequence Principle Components

Given the autoregressive parameters and discrete state sequence, the data sequence y was generated according to an affine autoregression:

$$Y_t \sim \text{Normal}(A^{(x_t)} \tilde{y}_{t-1} + b^{(x_t)}, \Sigma^{(x_t)}) t=K+1, K+2, \ldots, T$$

where $\tilde{y}$ denotes a vector of K lags:

$$\tilde{y}_t \overset{def}{=} \begin{bmatrix} y_{t-K}^T & y_{t-K+1}^T & y_{t-1}^T \end{bmatrix}^T$$

The alternative models are special cases of the AR-HMM and were constructed by adding constraints. In particular, the Gaussian-emission HMM (G-HMM) corresponds to constraining $A^{(i)}=0$ for each state index i. Similarly, the autoregressive mixture (AR-MM) and Gaussian mixture (GMM) correspond to constraining the transition matrix to be constant across rows, $\pi_{ij}=\pi_{i'j}=\pi_j$ for each i and i', in the AR-HMM and G-HMM, respectively.

Specific Implementation of Inference Algorithms to Examples

As discussed above, the Gibbs sampling inference algorithm alternated between two principal stages: updating the segmentation of the data into modules given a fixed transition matrix and autoregressive parameters, and updating the transition matrix and autoregressive parameters given a fixed segmentation. Mathematically, updating the segmentation sampled the label sequence x conditioned on the values of the data y, the autoregressive parameters $\theta$, and the transition matrix $\pi$; that is, sampling the conditional random variable $x|\theta,\pi,y$. Similarly, updating the transition matrix and autoregressive parameters given the segmentation sampled $\pi|x$ and $\theta|x,y$, respectively.

For inference in the AR-HMM the weak limit approximation to the Dirichlet process was used, in which the infinite model was approximated by a finite one. That is, choosing some finite approximation parameter L, $\beta$ and $\pi$ were modeled using finite Dirichlet distributions of size L $$\beta \sim Die(\gamma/L, \ldots, \gamma/L)$$

$$\pi_k \sim Dir(\alpha\beta_1, \ldots, \alpha\beta_j + k\delta kj, \ldots, \alpha\beta_L)$$

where $\pi_k$ denotes the ith row of the transition matrix. This finite representation of the transition matrix allowed the state sequence x to be resampled as a block and for large L provides an arbitrarily good approximation to the infinite Dirichlet process.

Using a weak limit approximation, the Gibbs sampler for the AR-HMM iterated resampling the conditional random variables $$x|\pi, \theta, y \theta |x, y \text{ and } \beta, \pi|x$$

For simplicity, throughout this section notation for conditioning on hyperparameters and the superscript notation for multiple observation sequences is suppressed.

Sampling $x|\pi, \theta, y$

Sampling the state labels x given the dynamical parameters, $\pi$ and $\theta$, and the data y corresponds to segmenting the 3D video sequence and assigning each segment to a behavioral mode that describes its statistics.

Given the observation parameters $\theta$ and the transition parameters $\pi$, the hidden state sequence x is Markov with respect to a chain graph. The standard HMM backward message passing recursions are $$B_t(k) = p(y_{t+1:T}|\theta, \pi, x_t = k) = \sum_{j=1}^{K} p(x_{t+1} = j|x_t = k, \pi) p(y_{t+1}|x_{t+1} = j, \theta) B_{t+1}(j)$$

for $t = 1, 2, \ldots, T-1$ and $k = 1, 2, \ldots, K$, where $B_T(k) = 1$ and where $y_{t+1:T} = (y_{t+1}, y_{t+2}, \ldots, y_T)$. Using these messages, the conditional distribution of the first state marginalizing over all the future states $X_{2:T}$ is $$p(x_1 = k|\pi, \theta, y) \propto p(x_1 = k|\pi) p(y_1|x_1 = k, \theta) B_1(k)$$

which can be sampled efficiently. Given a sampled value z 1, the conditional distribution of the second state $x_2$ is $$p(x_2 = k|\pi, \theta, y, x_1 = \bar{z}) \propto p(x_2 = k|x_1 = \bar{z}_1, \pi) p(y_2|x_2 = k, \theta) B_2(k).$$

Therefore after passing HMM messages backward the state sequence can be recursively sampled forwards.

Sampling $\theta|x, y$

Sampling the autoregressive parameters $\theta$ given the state sequence x and the data sequence y corresponds to updating each mode's dynamical parameters to describe the 3D video data segments assigned to it.

To resample the observation parameters $\theta$ conditioned on a fixed sample of the state sequence x and the observations y one can exploit conjugacy between the autoregressive likelihood and the MNIW prior. That is, the conditional also follows the MNIW distribution:

$$p(A^{(k)}, \Sigma^{(k)}|x, y, S_0, v_0, M_0, k_0) = p(A^{(k)}, \Sigma_{(k)}|S_n, v_n, M_n, K_n)$$

where $(S_n, v_n, M_n, K_n)$ are posterior hyperparameters that are functions of the elements of y assigned to state k as well as the preceding lagged observations:

$$S_n = S_0 + S_{yy^T} + (M_0 K_0^{-1} M_0^T - M_n K_n^{-1} M_n^T)$$

$$M_n = (M_0 K_0^{-1} + S_{y\tilde{y}^T}) K_n$$

$$K_n = (K_0^{-1} + S_{\tilde{y}\tilde{y}^T})^{-1}$$

$$v_n = v_0 + n$$

where $$S_{yy^T} = \sum_{t: x_t = k} y_t y_t^T$$

$$S_{\tilde{y}\tilde{y}^T} = \sum_{t: x_t = k} \tilde{y}_t \tilde{y}_t^T$$

$$S_{y\tilde{y}^T} = \sum_{t: x_t = k} y_t \tilde{y}_t^T$$

$$n = \#\{t: x_t = k\}.$$

Therefore resampling $\theta|x, y$ includes three steps: collecting statistics from the data assigned to each state, forming each state's posterior hyperparameters, and updating each state's observation parameter by simulating a draw from the appropriate MNIW. Simulating $(A, \Sigma) \sim MNIW(S_n, v_n, M_n, K_n)$ proceeds as $$\Sigma \sim InvWishart(S_n, v_n)$$

$$A = M_n + \sum^{\frac{1}{2}} G K_n^{-\frac{1}{2}} \text{ where } G_{ij} \stackrel{iid}{\sim} \mathcal{N}(0, 1).$$

Sampling $\beta, \pi|x$

Sampling the transition parameters $\pi$ and $\beta$ given the state sequence x corresponds to updating the probabilities of transitions among behavioral modules to reflect the transition patterns observed in the state sequence. Updating $\beta$ encouraged redundant behavioral modes to be pruned from the model, while updating each $\pi_{ij}$ fit the transitions observed from state i to state j.

Resampling the transition parameters $\beta$ and $\pi$, which are draws from the weak limit approximation to the (sticky) HDP, was performed using an auxiliary variable sampling scheme. That is, $\beta, \pi|x$ was generated by first sampling auxiliary variables $m|\beta, x$. Then $\beta, \pi|x, m$ was generated by first sampling from the marginal $\beta|m$ and then the conditional $\pi|\beta, x$.

The matrix of transition counts in the sampled state sequence x is $$n_{kj} = \#\{t: x_t = k, x_{t+1} = j, t = 1, 2, \ldots, T-1\}.$$

Suppressing conditioning notation for simplicity, the auxiliary variables m $\{m_{kj}: k, j = 1, 2, \ldots, K\}$ are sampled via $$m_{kj} = \sum_{l=1}^{n_{kj}} b_{kjl} \text{ where } b_{kjl} \stackrel{iid}{\sim} \text{Bernoulli}\left(\frac{\alpha\beta_j}{\alpha\beta_j + \kappa} \frac{\alpha\beta_j + \kappa\delta_{kj}}{\alpha\beta_j + 1 + \kappa\delta_{kj}}\right)$$

where Bernoulli(p) denotes a Bernoulli random variable that takes value 1 with probability p and takes value 0 otherwise. Note that the update for the HDP-HMM without a sticky bias corresponds to setting k=0 in these updates.

Given the auxiliary variables, the update to $\beta$ is a Dirichlet-multinomial conjugate one, where $$\beta|m \sim Dir(\gamma/K + m_{\cdot 1}, \gamma/K + m_{\cdot 2}, \ldots, \gamma/L + m_{\cdot k})$$

where $m_{\cdot j} = \sum_{k=1}^{K} m_{kj}$ for $j = 1, 2, \ldots, K$. The update to $\pi|\beta, x$ is similar, with $$\pi_k|\beta, x \sim Dir(\alpha\beta_1 + n_{k1}, \ldots, \alpha\beta_j + n_{kj} + k\delta_{kj}, \ldots, \text{alpha}\beta_k + n_{kK}).$$

Application of the Models to the Examples

Datasets from the open-field, odor, and genetic manipulation experiments were modeled jointly to increase statistical power. Because the neural implants associated with the optogenetics experiment modestly altered the profile of the animal, these data were modeled separately. In all experiments, the first 10 principal components for each frame of each imaged mouse were gathered. Data were then subdivided and assigned either a "train" or a "test" label, in a 3:1 train:test ratio. The mice labeled "test" were held-out from the training process, and used to test generalization performance via measurement held-out likelihood. This approach allowed us to directly compare algorithms whose composition reflected different underlying structures for behavior.

We trained models on data using the procedures described herein; modeling was robust to both initialization settings and to parameter and hyperparameter settings (with the exception of kappa, see below). Specifically, the number of lags used in our AR observation distributions and the number of used states in our transition matrix with an HDP prior was found to be robust to the particular hyperparameter settings on both priors. We varied the hyperparameters of our sparsifying ARD prior by several orders of magnitude, and held-out likelihood, the number of used lags, and the number of used states varied negligibly. We also varied the hyperparameters of our HDP prior by several orders of magnitude and again observed no change to the number of used states or held-out likelihood. All jointly-trained data shared observation distributions, but each treatment class was allowed its own transition matrix. Each model was updated through 1000 iterations of Gibbs sampling; upon the last iteration of Gibbs sampling the model output was saved; all further analysis was performed on this final update.

The "stickiness" of the duration distribution of our behavioral modules—defined by the kappa setting of the model—influenced the average duration of behavioral modules discovered by the AR-HMM; this allowed us to control the temporal scale at which behavior was modeled. As discussed in the main text, autocorrelation, power spectral density, and the changepoint algorithm identified switching dynamics at a specific sub-second temporal scale (as encapsulated by the changepoints duration distribution and reflected by the spectrogram and autocorrelogram). We therefore empirically set the kappa stickiness parameter of the time-series model to best match the duration distribution discovered by changepoint detection. To find the kappa setting at which these distributions were best matched, we minimized the Kolmogorov-Smirnov distance between the inter-changepoint interval distribution and the posterior behavioral module duration distribution through a dense grid search.

Mouse Strains, Housing and Habituation

Unless otherwise noted, all experiments were performed on 6-8 week old C57/BL6 males (Jackson Laboratories). Mice from the rotβ and rbp4 strains were habituated and tested identically to the reference C57/BL6 mice. Mice were brought into our colony at 4 weeks of age, where they were group-housed for two weeks in a reverse 12 hours light/12 hours dark cycle. On the day of testing, mice were brought into the laboratory in a light-tight container, where they were habituated in darkness for 30 minutes before testing.

Example 1. Behavioral Assays: Innate Exploration

To address these possibilities, we first used the AR-HMM to define the baseline architecture of mouse exploratory behavior in the open field, and then asked how this template for behavior was modified through distinct manipulations of the external world.

For the open field assay (OFA), mice were habituated as noted above, and then placed in the middle of a circular 18" diameter enclosure with 15"-high walls (US Plastics), immediately after which 3D video recording was begun. The animal was allowed to freely explore the enclosure for the 30 minute experimental period. Mice whose behavior was assessed in a square box were handled and measured identically to the OFA, except in the odor box described below.

Figure 5A:
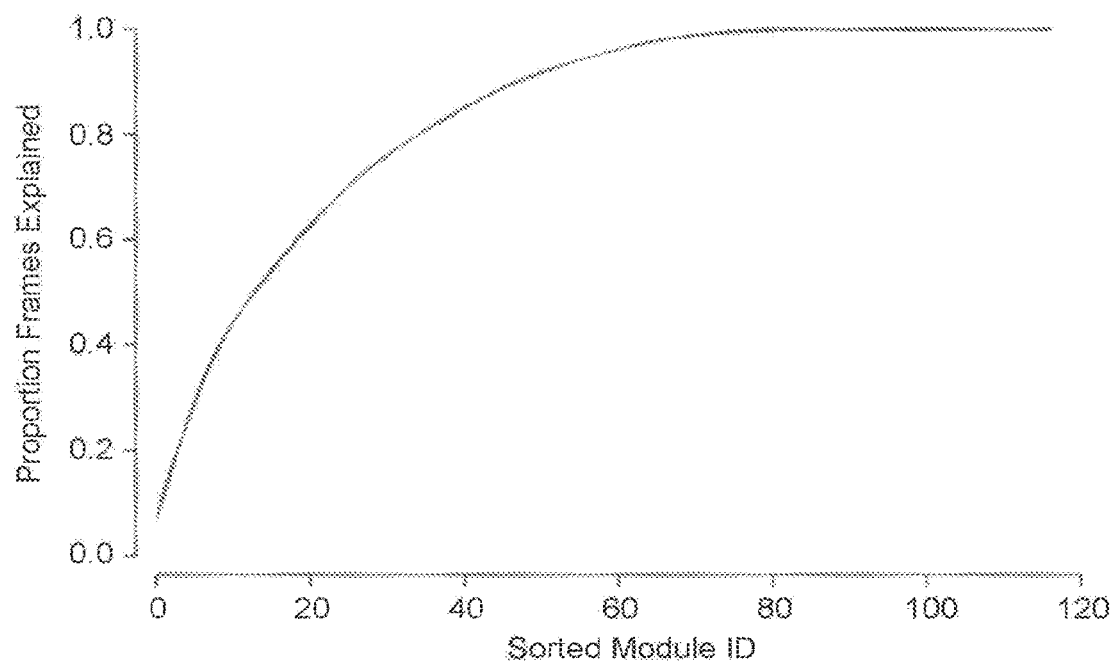
FIG. 5A depicts, in accordance with various embodiments of the present invention, a graph showing the proportion of frames explained by each module (Y axis), plotted against the set of modules, sorted by usage (X axis)
Figure 5B:
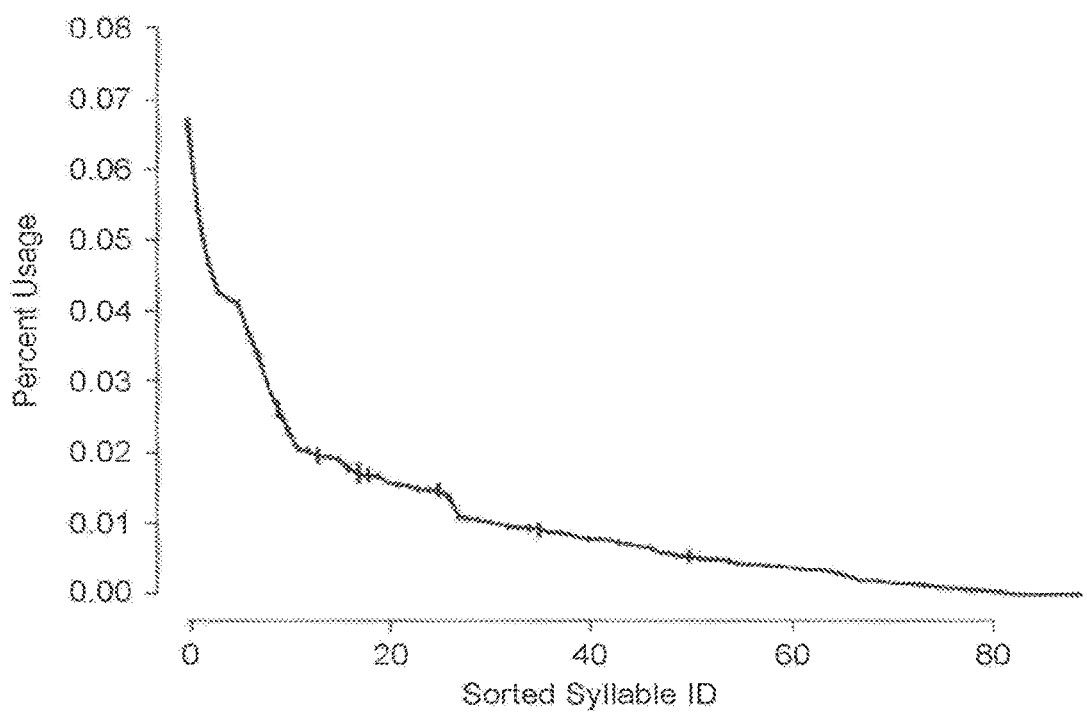
FIG. 5B depicts, in accordance with various embodiments of the present invention, a graph showing modules (X axis) sorted by usage (Y axis) with Bayesian credible intervals indicated.
Figure 6A:
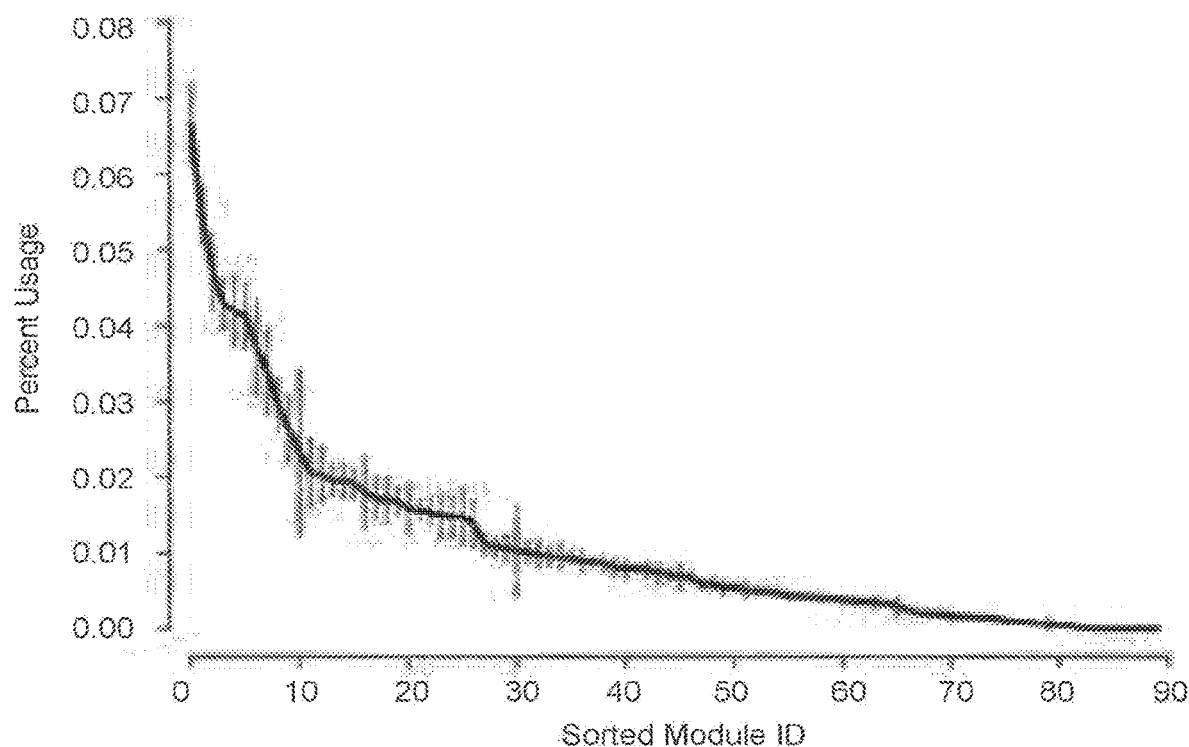
FIGS. 6A-6E depict, in accordance with various embodiments of the present invention, the influences of the physical environment on module usage and spatial pattern of expression.

The AR-HMM identified ~60 reliably-used behavioral modules (51 modules explained 95 percent of imaging frames, and 65 modules explained 99 percent of imaging frames, FIGS. 5A, 5B) from the circular open field dataset, which is representative of normal mouse exploratory behavior in the laboratory (FIG. 6A, n=25 animals, 20 minute trials). FIG. 5A shows the proportion of frames explained by each module (Y axis), plotted against the set of modules, sorted by usage (X axis). Ninety-five percent of frames were explained by 51 behavioral modules; ninety-nine percent of frames were explained by 62 behavioral modules in the open field dataset.

FIG. 5B shows modules (X axis) sorted by usage (Y axis) with Bayesian credible intervals indicated. Note that all the credible intervals are smaller than the SEs computed based upon the bootstrap estimates (FIG. 5B). As noted above, many of these modules encode human-describable components of behavior (e.g. rears, walking, pauses, turns).

Figure 6B:
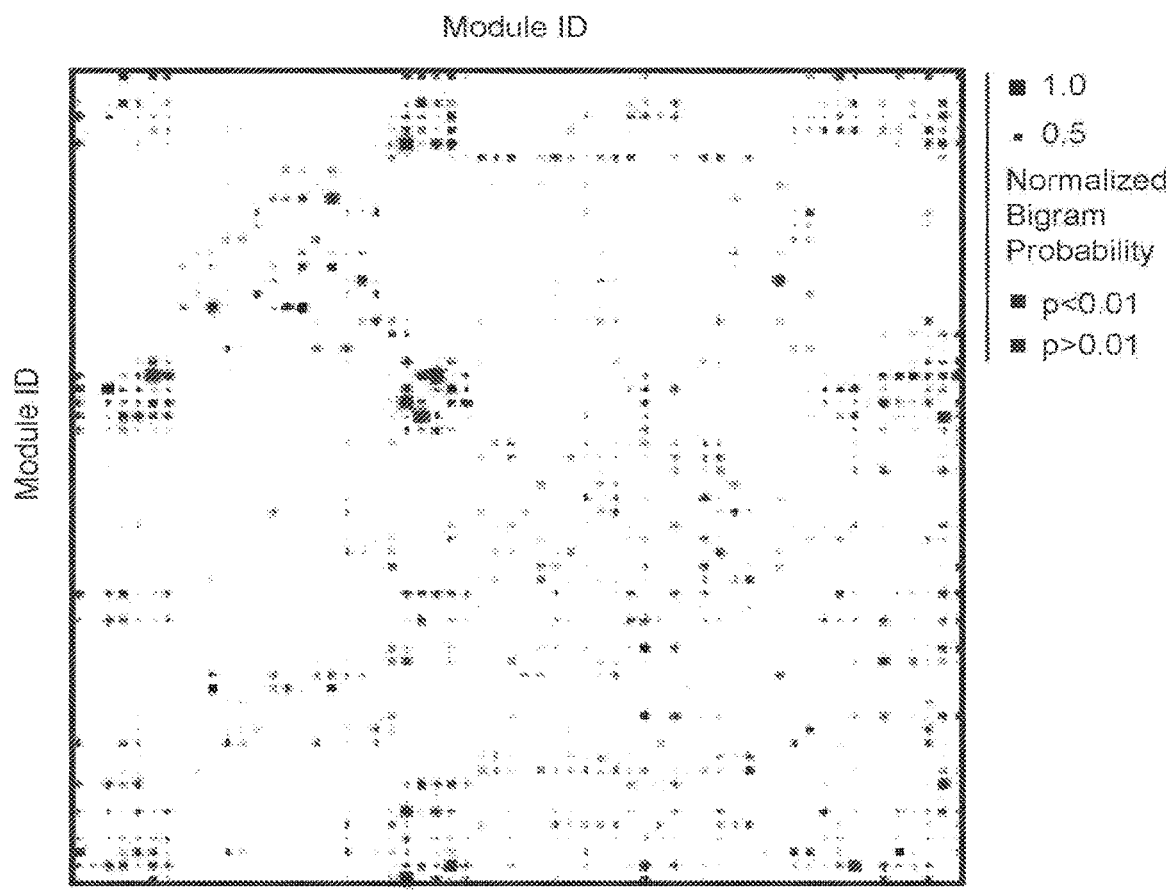

The AR-HMM also measures the probability that any given module precedes or follows any other module; in other words, after model training each module is assigned a pairwise transition probability with every other module in the set; these probabilities summarize the sequences of modules that were expressed by the mouse during behavior. Plotting these transition probabilities as a matrix revealed that they were highly non-uniform, with each module preferentially connected in time to some modules and not others (FIG. 6B; average node degree without thresholding 16.82±0.95, after thresholding bigram probabilities lower than 5 percent, 4.08±0.10). This specific connectivity between pairs of modules restricted the module sequences that were observed in the dataset (8900/~125,000 possible trigrams) demonstrating that certain module sequences were favored; this observation suggests that mouse behavior is predictable, as knowing what the mouse is doing at any given moment in time informs an observer about what the mouse is likely to do next. Information theoretic analysis of the transition matrix confirmed that mouse behavior is significantly predictable, as the average per-frame entropy rate was low relative to a uniform transition matrix (without self-transitions 3.78±0.03 bits, with self-transitions 0.72±0.01 bits, entropy rate in uniform matrix 6.022 bits), and the average mutual information between interconnected modules was significantly above zero (without self-transitions 1.92±0.02 bits, with self-transitions 4.84 bits±0.03 bits). This deterministic quality to behavior likely serves to ensure that the mouse emits coherent patterns of motion; consistent with this possibility, upon inspection frequently-observed module sequences were found to encode different aspects of exploratory behavior.

Figure 6C:
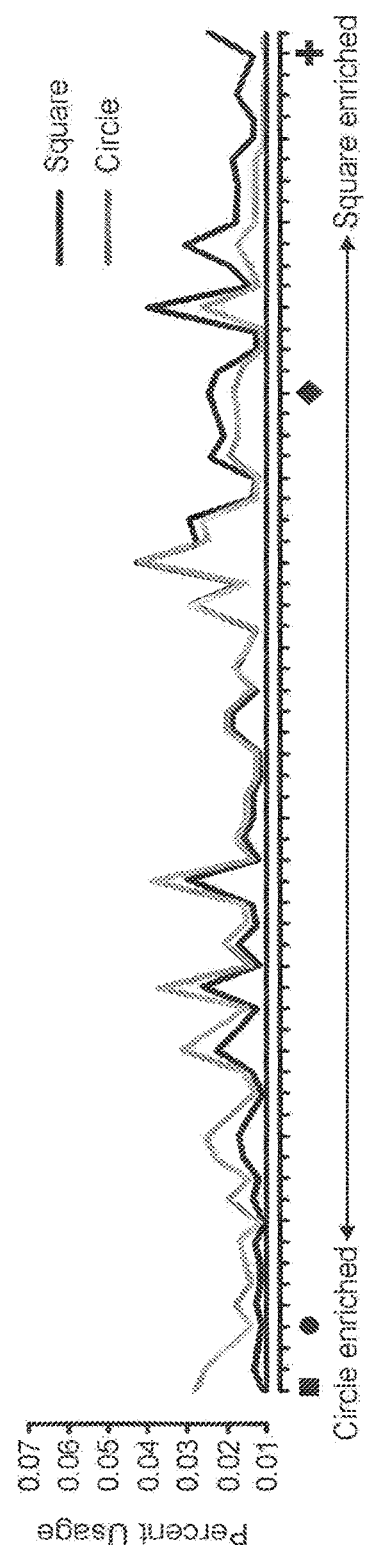

The behavior expressed by mice in the circular open field reflects a context-specific pattern of locomotor exploration. We hypothesized that mice would adapt to changes in apparatus shape by focally altering the structure of behavior to generate new pose dynamics to interact with specific physical features of the environment; to test this hypothesis, we imaged mice within a smaller square box and then co-trained our model with both the circular open field data and square data, thereby enabling direct comparisons of modules and transition under both conditions (n=25 mice in each condition). Although mice tended to explore the corners of the square box and the walls of the circular open field, the overall usage of most modules was similar between these apparatuses, consistent with exploratory behavior sharing many common features across arenas (FIG. 6C). The AR-HMM also identified a small number of behavioral modules that were deployed extensively in one context, but negligibly or not at all in the other, consistent with the idea that different physical environments drive expression of new behavioral modules (FIG. 6C, for all usage differences discussed below $p<10^{-3}$ based upon bootstrap estimation).

Figures 6D, 6E:
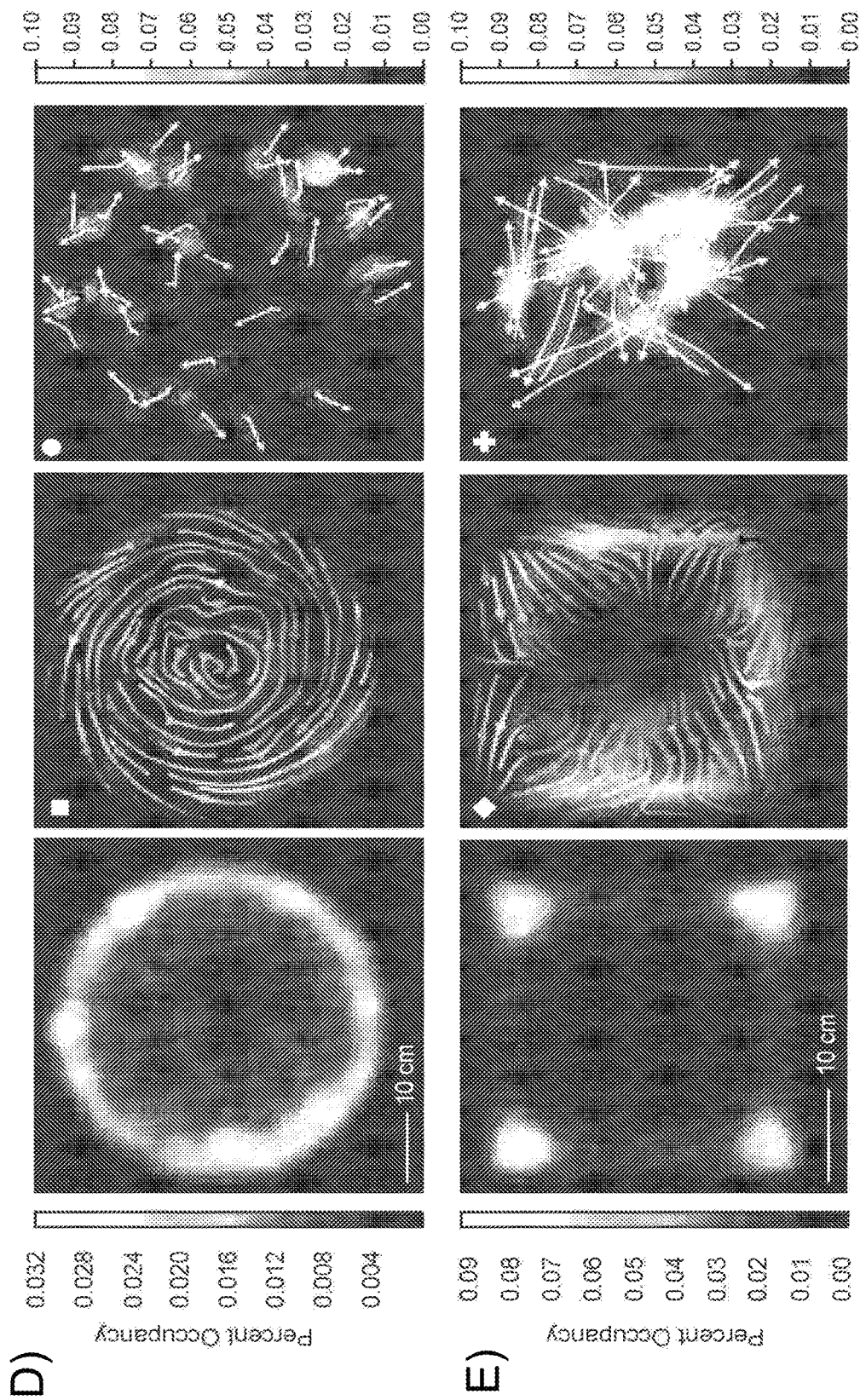

Interestingly, these "new" modules are not only deployed during physical interactions with specific features of the apparatus—which would be predicted to elicit new pose dynamics—but also during unconstrained periods of exploration. For example, one circular arena-specific module encoded a thigmotactic behavior in which the mouse locomotes near the arena wall with a body posture that matches the curvature of the wall. This module was also expressed when the mouse is closer to the center of the circular arena and not in physical contact with the wall, demonstrating that expression of this module is not simply the direct consequence of physical interactions with the wall but rather reflects the behavioral state of the mouse in a curved arena; while thigmotaxis also occurred in the square box, the associated behavioral module encodes locomotion with a straight body and was used during straight trajectories in both square and circular apparatuses (FIGS. 6D-E, middle panels). Similarly, within the square box mice expressed a context-specific module that encodes a dart from the center of the square to one of the adjacent corners; this pattern of motion likely was a consequence of the square having a small central open field, and was not the specific product of a physical constraint placed upon the mouse.

A number of additional modules were found to be preferentially expressed in one context or the other; these upregulated modules appeared to encode behaviors that were deployed in allocentric patterns specified by the shape of the arena. In the circular arena, for example the mouse preferentially expressed a rear in which the mouse's body points outwards while it pauses near the center of the open field, while in the smaller square box mice preferentially executed a high rear in the corners of the box (FIG. 6E, data not shown). These results suggest that what the mouse does (i.e. its egocentric behavior) is modulated based upon where in space the mouse is (i.e. its allocentric position). Taken together, these data demonstrate that mice adapt to new physical environments, at least in part, through recruitment of a limited set of context-specific behavioral modules (that encode context-appropriate pose dynamics) into baseline patterns of action; these new modules—along with other modules whose expression is enriched in one context or the other—are differentially deployed in space to respond to changes in the environment.

Example 2. Behavioral Assays: Stimulus-Driven Innate Behaviors—Response to Odorants Because mice express the same underlying behavioral state—locomotor exploration—in both the circle and the square one might predict that the observed changes to behavioral modules in this case would be focal and limited in extent. Therefore, the inventors asked how the underlying structure of behavior is altered when mice are exposed to a sensory cue—within an otherwise-constant physical environment—that drives a global change in behavioral state that includes the expression of new and motivated actions.

To assess innate behavioral responses to volatile odorants, the inventors developed an odor delivery system that spatially isolates odors in specific quadrants of a square box. Each 12"×12" box was constructed of ¼" black matte acrylic (Altech Plastics), with ¾" holes patterning the bottom of the box in a cross formation, and a 1/16" thick glass cover (Tru Vue). These holes were tapped and connected via PTFE tubing to a vacuum manifold (Sigma Aldrich) that provides negative pressure to isolate odors within quadrants. Odor was injected into the box through ½" NPT-⅜" pipe-fittings (Cole-Parmer). Filtered air (1.0 L/min) was blown over odorant-soaked blotting paper (VWR) placed at the bottom of Vacutainer syringe vials (Covidien). The odorized airstream was then passed through corrugated PTFE tubing (Zeus) into one of the four pipe-fittings in a corner of the odor box.

The inventors verified the ability of the odor box to isolate odors within specified quadrants by visualizing vaporized odor or smoke through sheet illumination of the box with a low-power handheld HeNe laser. This approach allowed us to tune the vacuum flow and odor flow rates to achieve odor isolation, which was verified using a photoionization device (Aurora Scientific). To eliminate the possibility of cross contamination between experiments, the odor boxes were soaked in a 1% Alconox solution overnight, then thoroughly cleaned with a 70% ethanol solution. Mice were habituated to the experimental room for 30 minutes before the initiation of the experiment. Under control conditions, dipropylene glycol with air (1.0 L/min) was delivered to each of the four corners of the apparatus before a single mouse was placed in the center of the box and allowed to freely explore while 3D video records were acquired for 20 minutes. The same cohort of animals was tested for odor responses by subsequently repeating the experiment with odorized air delivered to one of the four quadrants. All 3D video recordings are performed in total darkness. TMT was obtained from Pherotech, and used at 5% concentration.

Figure 7:
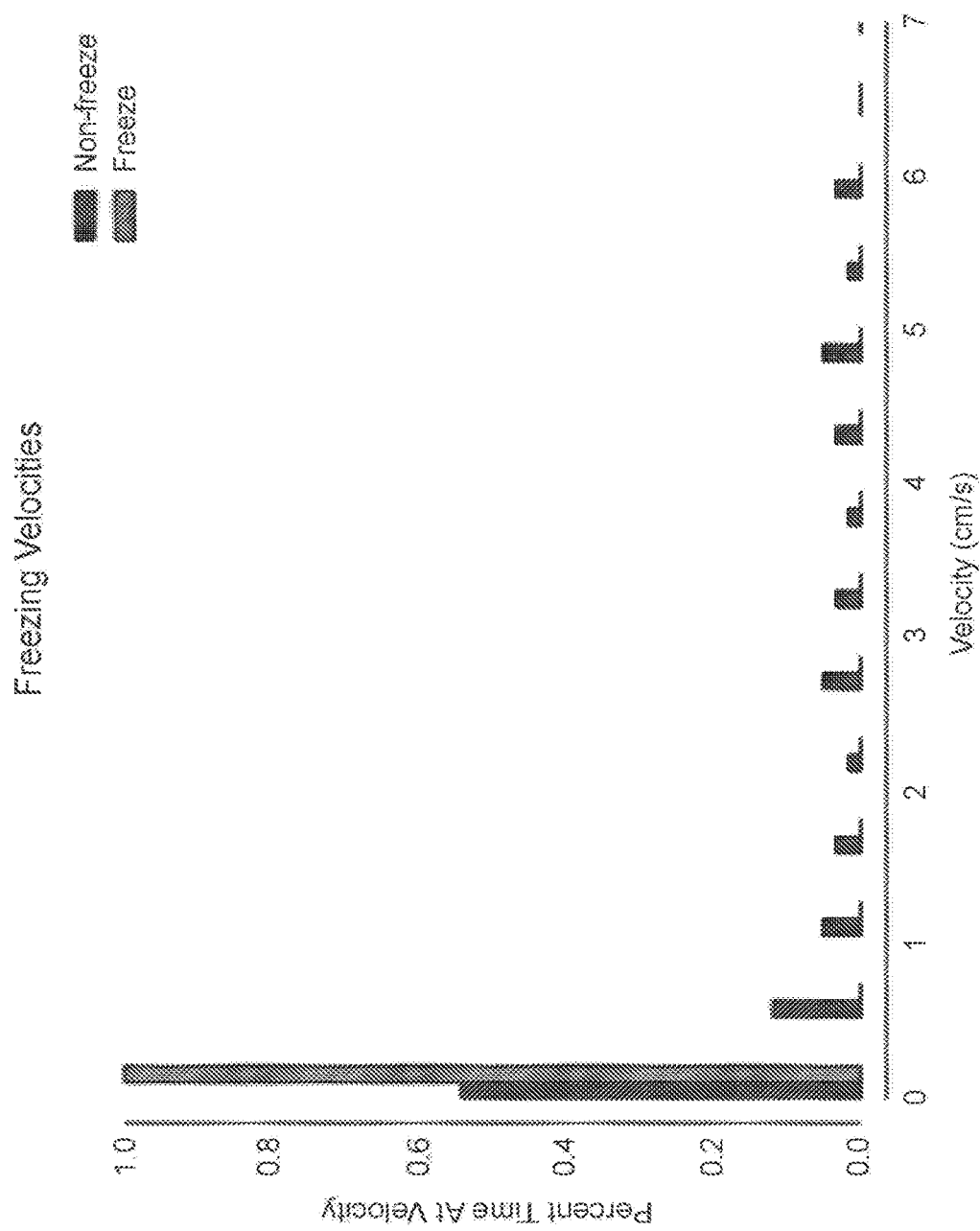
FIG. 7 depicts, in accordance with various embodiments of the present invention, a histogram depicting the average velocity of the modules that were differentially upregulated and interconnected after TMT exposure "freezing" compared to all other modules in the dataset.

Mice exploring the square box were therefore exposed to the aversive fox odor trimethylthiazoline (TMT), which was delivered to one quadrant of the box via olfactometer. This odorant initiates a complex and profound behavioral state change including odor investigation, and escape and freezing behaviors that are accompanied by increases in corticosteroid and endogenous opioid levels. Consistent with these known effects, mice sniffed the odor-containing quadrant, and then avoided the quadrant containing the predator cue and displayed prolonged periods of immobility traditionally described as freezing behavior (FIG. 7). FIG. 7 shows a histogram depicting the average velocity of the modules that were differentially upregulated and interconnected after TMT exposure "freezing" compared to all other modules in the dataset.

Surprisingly, this suite of new behaviors was encoded by the same set of behavioral modules that were expressed during normal exploration; several modules were up- or downregulated after TMT exposure, but no new modules were introduced or eliminated relative to control (n=25 animals in control conditions, n=15 in TMT, model was co-trained on both datasets simultaneously). Instead, TMT altered the usage of and transition probabilities between specific modules, leading to newly-favored behavioral sequences that encode TMT-regulated behaviors (for all usage and transition differences discussed below p<10⁻³ based upon bootstrap estimation).

Plotting the module transitions altered after exposure to TMT defined two neighborhoods within the behavioral statemap; the first included an expansive set of modules and interconnections that were modestly downregulated by TMT, and the second included a focused set of modules and transitions that were upregulated by TMT). During normal behavior these newly-interconnected modules were temporally dispersed and individually appear to encode for different morphological forms of pausing or balling up. In contrast, under the influence of TMT these modules were concatenated into new sequences that, upon inspection and quantification, were found to encode freezing behavior (average during-sequence velocity −0.14±0.54 mm/sec, for other modules 34.7±53 mm/sec). For example, the most commonly-expressed freezing trigram was expressed 716 times after TMT exposure (in 300 minutes of imaging), as opposed to just 17 times under control conditions (in 480 minutes of imaging). The TMT-induced neighborhood structure imposed upon these pausing modules to create freezing demonstrates that behavior can be altered through focal changes in transition probabilities. This local rewriting of transition probabilities was accompanied by an increase in the overall determinism of mouse behavior—its global pattern of action became more predictable as a consequence of TMT exposure (per frame entropy rate fell from 3.92±0.02 bits to 3.66±0.08 bits without self-transitions, and from 0.82±0.01 bits to 0.64±0.02 bits with self-transitions) consistent with the mouse enacting an deterministic avoidance strategy.

Figure 8A:
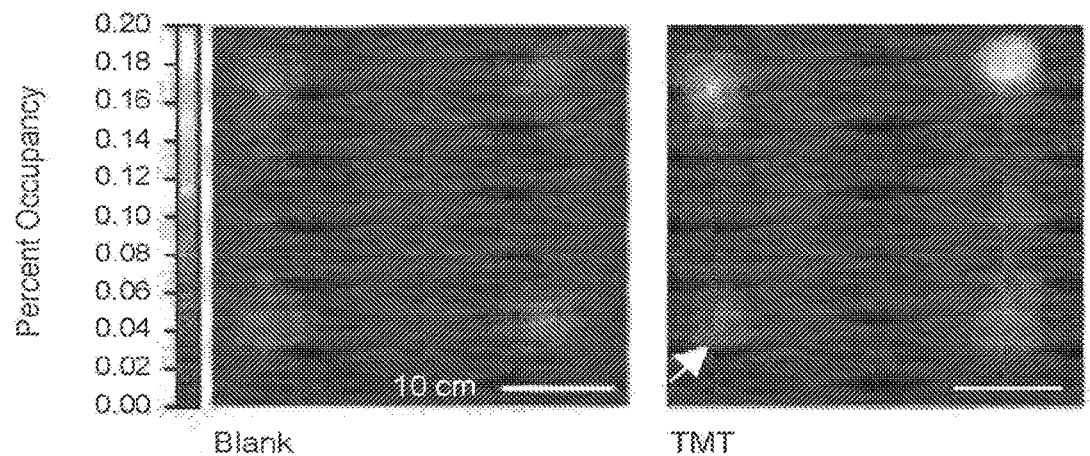
Figure 8B:
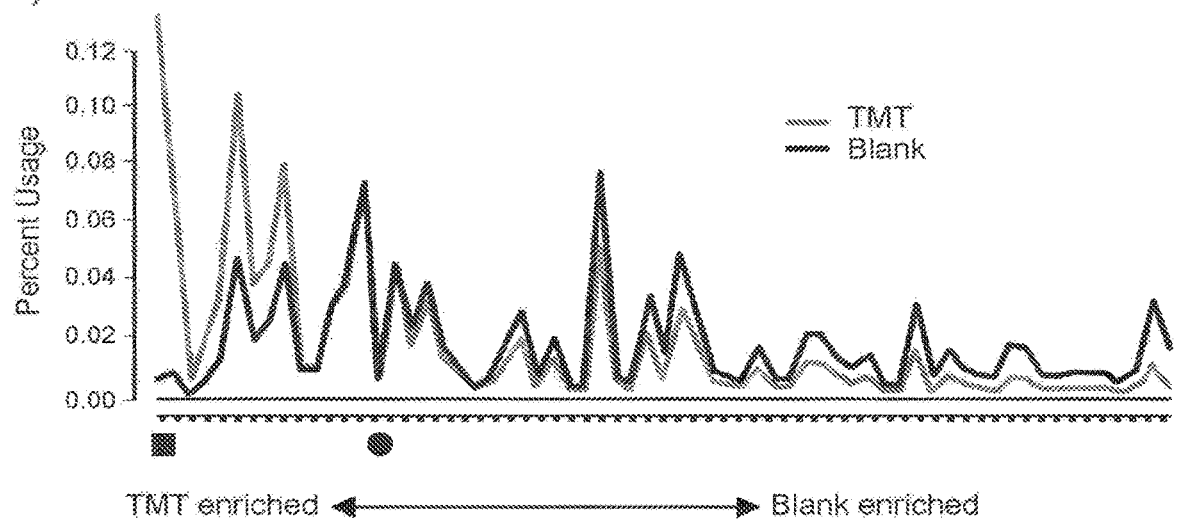
Figure 8D:
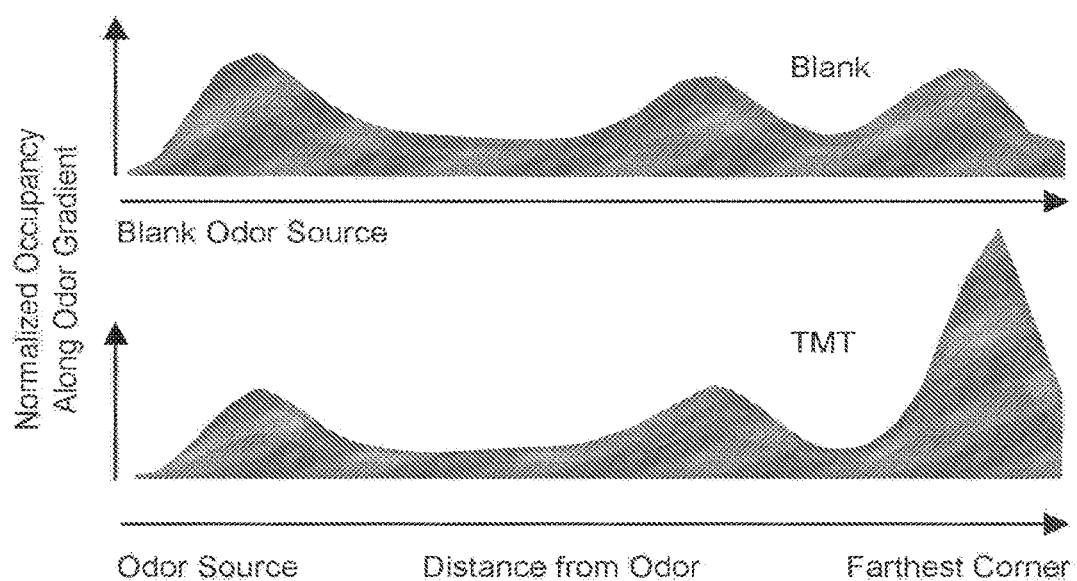
Figure 8E:
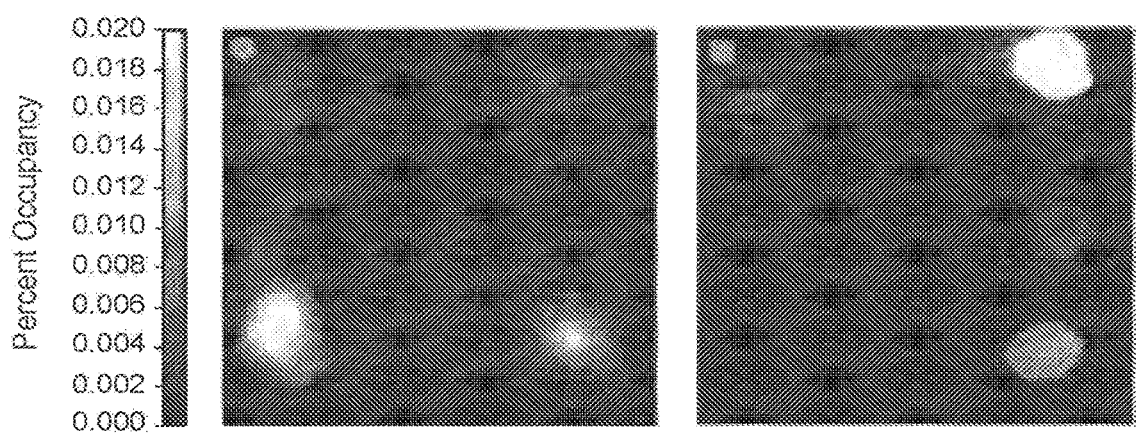

Proximity to the odor source also governed the pattern of expression of specific behavioral modules (FIGS. 8D-8E). For example, a set of freezing-related modules tended to be expressed in the quadrant most distal from the odor source, while the expression of an investigatory rearing module (whose overall usage was not altered by TMT) was specifically enriched within the odor quadrant (FIGS. 8D-8E). Together, these findings suggest two additional mechanisms through which the mouse nervous system can generate new and adaptive behaviors. First, the transition structure between individual modules that are otherwise normally associated with a different behavioral state, such as locomotor exploration, can be altered to generate new behaviors such as freezing. Second, the spatial patterns of deployment of pre-existing modules and sequences can be regulated to support motivated behaviors such as odor investigation and avoidance. Behavioral modules are not, therefore, simply reused over time, but instead act as flexibly interlinked components of behavioral sequences whose expression is dynamically regulated both in time and space.

Example 3. The Effect of Genes and Neural Circuits on Modules

As described above, the fine-timescale structure of behavior is selectively vulnerable to changes in the physical or sensory environment that influence action over timescales of minutes. Furthermore, the AR-HMM appears to comprehensively encapsulate the pattern of behavior expressed by the mouse (within the limits of our imaging). These observations suggest that the AR-HMM— which affords a systematic window into mouse behavior at the sub-second timescale— may be able to both quantify obvious behavioral phenotypes and to reveal new or subtle phenotypes induced after experimental manipulations that influence behavior across a range of spatiotemporal scales.

Figures 9A, 9B, 9C:
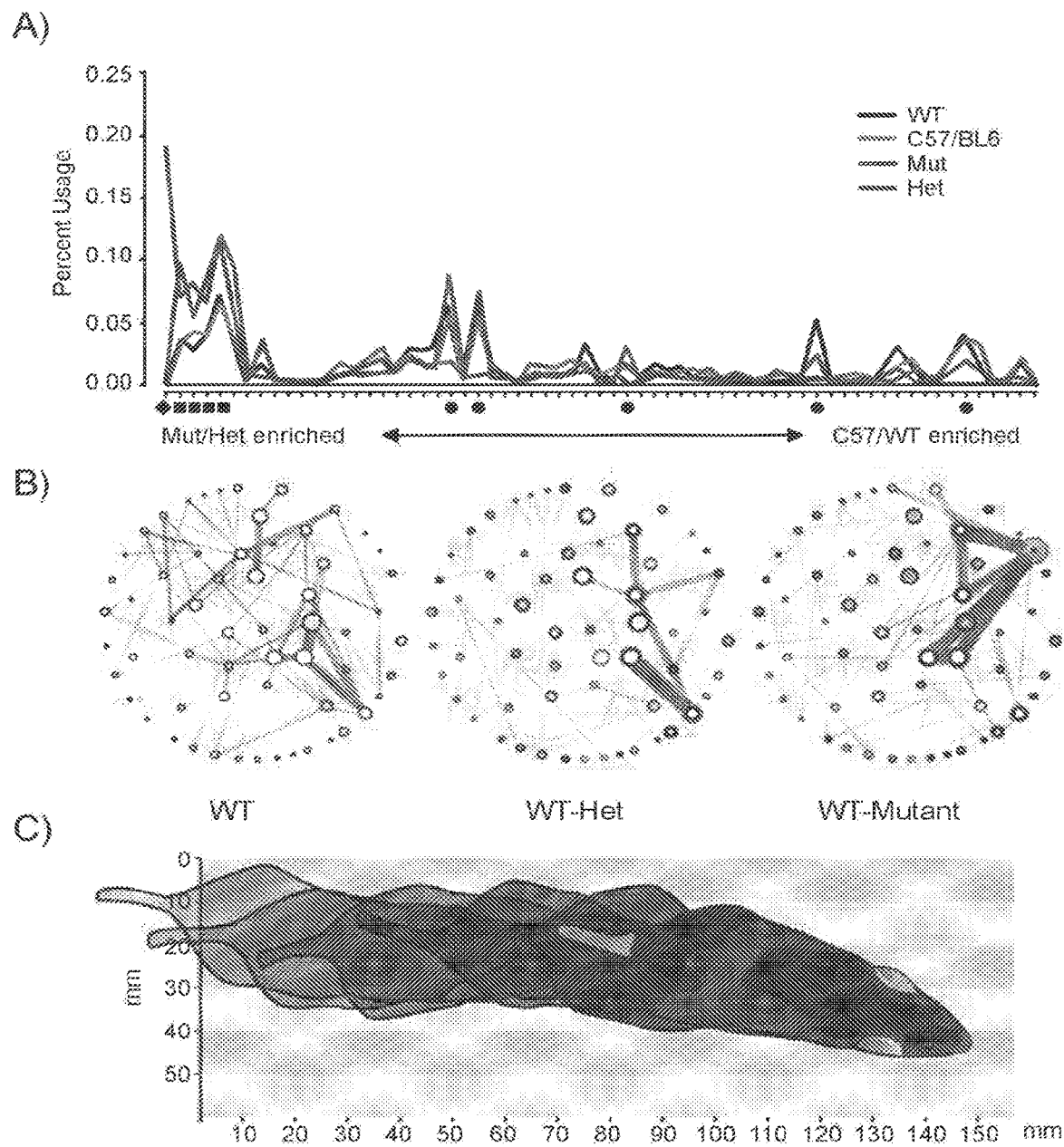
FIGS. 9A-9C depict, in accordance with various embodiments of the present invention, graphs illustrating how the AR-HMM disambiguates wild-type, heterozygous and homozygous mice.

To explore how changes in individual genes—which act on timescales of the lifetime of the mouse—might impact fast behavioral modules and transitions, we characterized the phenotype of mice mutant for the retinoid-related orphan receptor 1β (Ror1β) gene, which is expressed in neurons in the brain and spinal cord; we selected this mouse for analysis because homozygous mutant animals exhibit abnormal gait[37-40], which we would expect to be detected by the AR-HMM. After imaging and modeling, littermate control mice were found to be nearly indistinguishable from fully inbred C57/B16 mice, whereas mutant mice expressed a unique behavioral module that encoded a waddling gait (FIG. 9A, 9C). This alteration in behavior was accompanied by its converse: the expression of five behavioral modules encoding normal forward locomotion at different speeds in wild-type and C57 mice was downregulated in the Ror1β mutant (FIG. 9A, average during-module velocity=114.6±76.3 mm/sec). In addition, expression of a set of four modules that encoded brief pauses and headbobs were also upregulated (FIG. 9A, average during-module velocity=8.8±25.3 mm/sec); this pausing phenotype had not previously been reported in the literature. Interestingly, heterozygous mice—which have no reported phenotype[37-40], appear normal by eye, and exhibit wild-type running wheel behavior[40]—also were found to express a fully-penetrant mutant phenotype: they overexpressed the same set of pausing modules that were upregulated in the full Ror1β mutants, while failing to express the more dramatic waddling phenotype (FIG. 9A).

The AR-HMM therefore describes the pathological behavior of Ror1β mice as the combination of a single neomorphic waddling module and the increased expression of a small group of physiological modules encoding pausing behaviors; heterozygote mice express a defined subset of these behavioral abnormalities, whose penetrance is not intermediate but equals that observed in the mutant. These results suggest that the sensitivity of the AR-HMM enables fractionation of severe and subtle behavioral abnormalities within the same litter of animals, enables discovery of new phenotypes, and facilitates comparisons amongst genotypes. These experiments also demonstrate that genotype-dependent variations in behavior, the consequence of the indelible and lifetime alteration of a specific gene in the genome, can influence module expression and transition statistics that operate on timescales of milliseconds.

Example 4. Behavioral Assays: Optogenetics—Effect of Neural Activity on Modules Finally, the inventors wished to ask whether the behavioral structure captured by the AR-HMM would offer insight into fleeting or unreliable changes in behavior. The inventors therefore briefly triggered neural activity in motor circuits, and asked how stimulation at different levels of intensity influenced the moment-to-moment organization of behavior. The inventors unilaterally expressed the light-gated ion channel Channelrhodopsin-2 in corticostriatal neurons[41,42] and assessed behavioral responses before, during and after two seconds of light-mediated activation of motor cortex (n=4 mice, model was trained separately from previous experiments).

Four adult male Rbp4-Cre (The Jackson Laboratory) mice were anesthetized with 1.5% isoflurane and placed in a stereotaxic frame (Leica). Microinjection pipettes (O.D. 10-15 μm) were inserted into the left motor cortex (coordinates from Bregma: 0.5 AP, −1 ML, 0.60 DV). 0.5 μl of AAV5.EF1a.DIO.hChR2(H134R)-eYFP.WPRE.hGH (~$10^{12}$ infectious units/mL, Penn Vector Core) were injected in each mouse over 10 minutes followed by an additional 10 minutes to allow diffusion of viral particles away from the injection site. After the injection, a bare optic fiber with a zirconia ferrule (O.D. 200 µM, 0.37 numerical aperture) was inserted 100 µm above the injection site and secured to the skull with acrylic cement (Lang). Twenty-eight days following the viral injection, mice were placed in a circular arena and the optical implant was coupled to a laser pump (488 nm, CrystaLaser) via a patch-chord and a rotary joint (Doric Lenses). The laser was directly controlled from a PC. After 20 minutes of familiarization to the arena, the optostimulation was started. The laser power, the pulse width, the inter-pulse interval and the inter-train interval were controlled by custom-made software (NI Labview). Each train of laser pulses consisted of 30 pulses (pulse width: 50 ms) at 15 Hz. The interval between successive trains was set to 18 seconds. 50 trains were delivered for each laser intensity. The animal was progressively exposed to higher laser intensities over the course of the experiment.

Figures 10A, 10B:
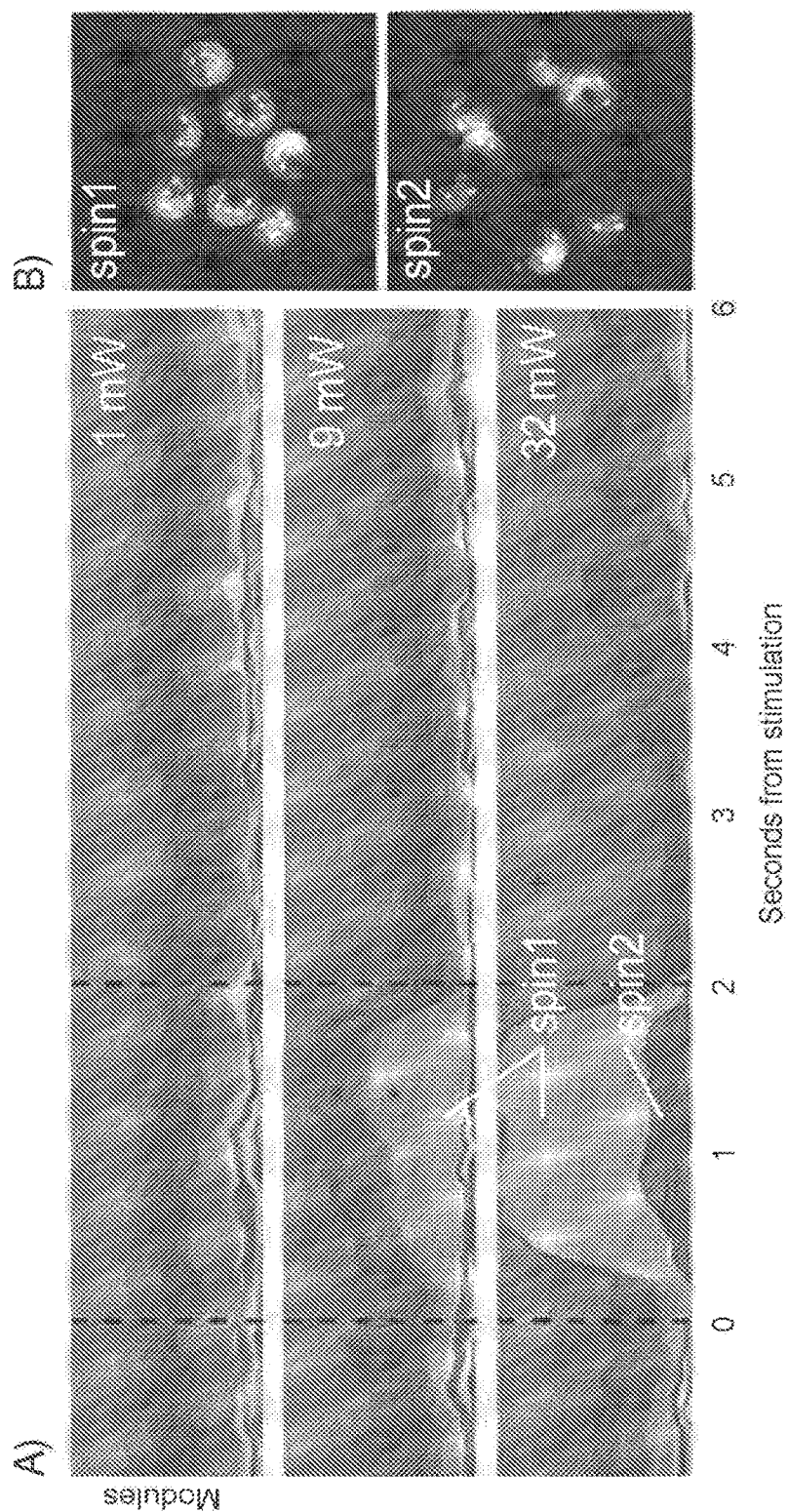
FIGS. 10A-10B depict, in accordance with various embodiments of the present invention, graphs illustrating how optogenetic perturbation of the motor cortex yields both neomorphic and physiological modules.
Figures 11A, 11B:
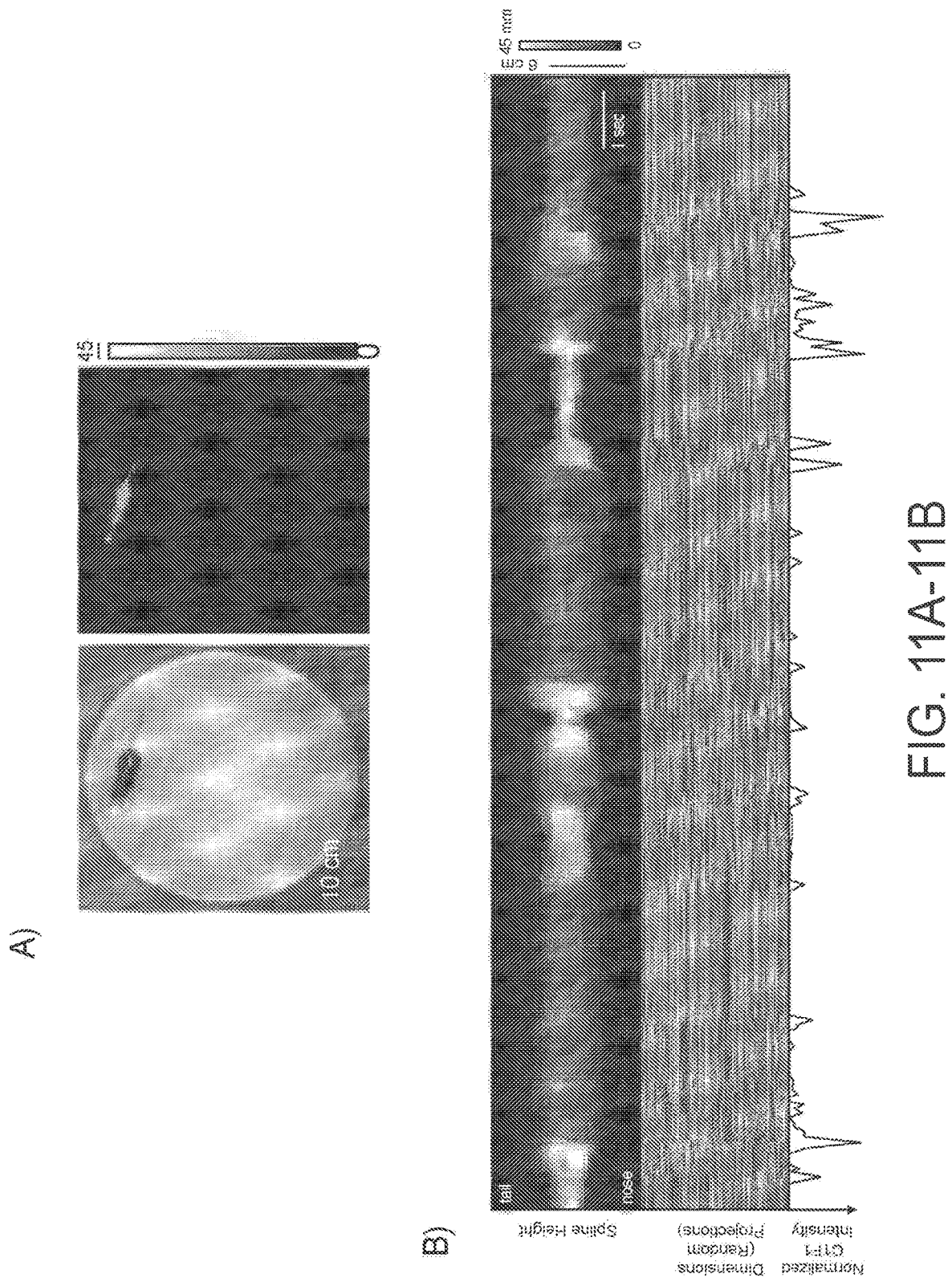
FIGS. 11A-11C depict, in accordance with various embodiments of the present invention, graphs illustrating how depth imaging reveals block structure in mouse pose dynamics data.
Figure 11C:
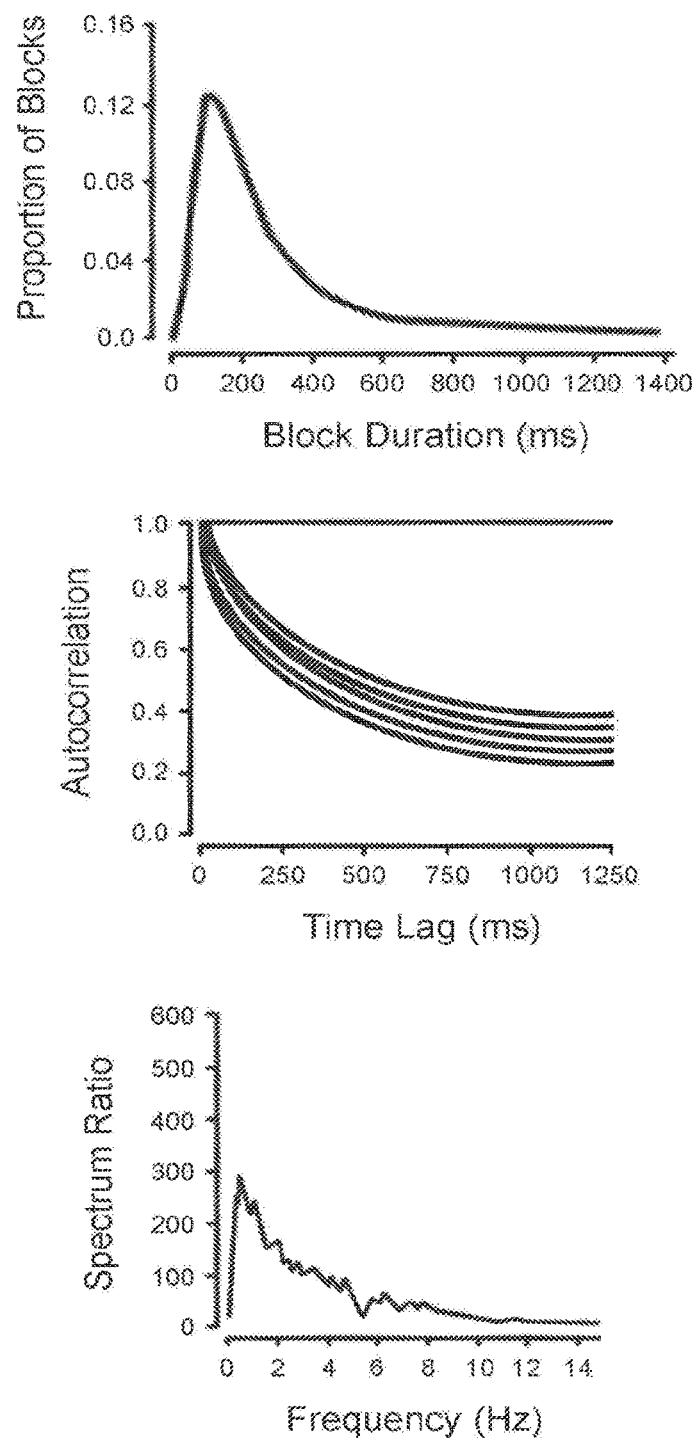
Figure 12A:
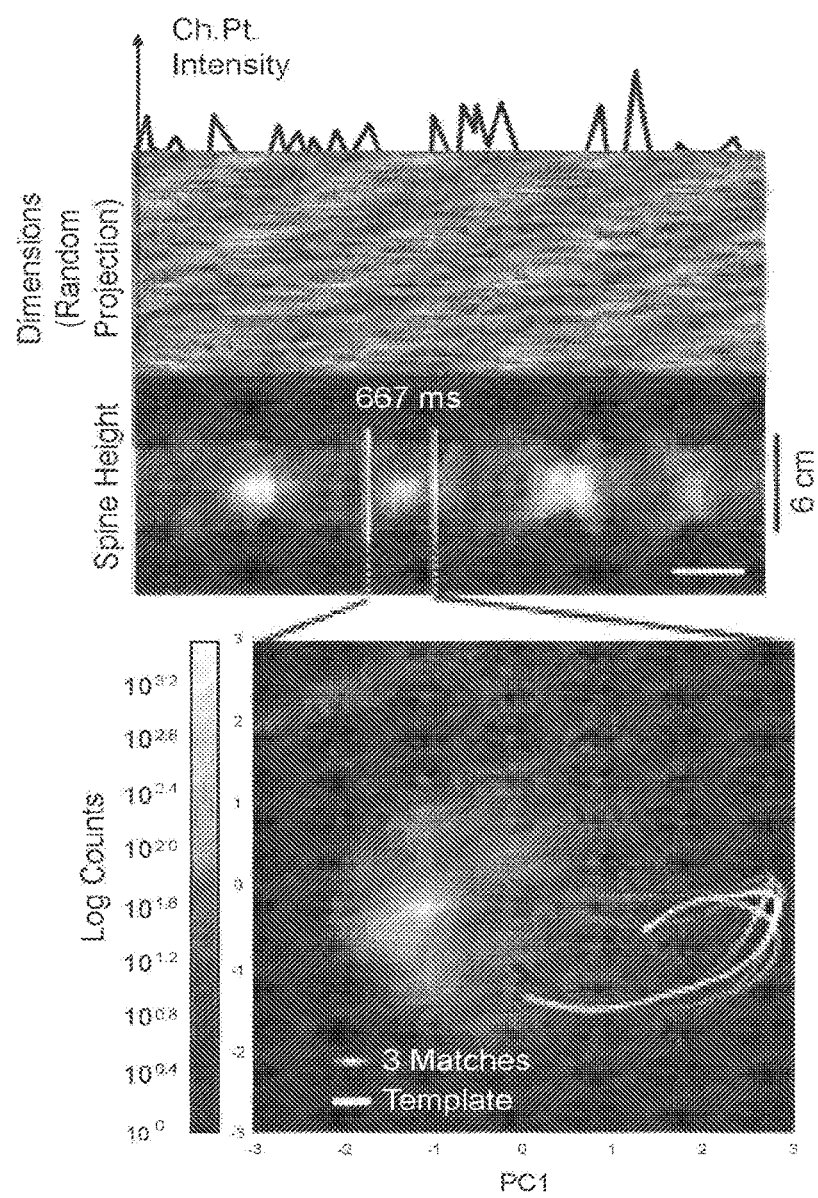
FIGS. 12A-12D depict, in accordance with various embodiments of the present invention, graphs illustrating how mouse pose dynamics data contains reused behavioral modules.
Figure 12B:
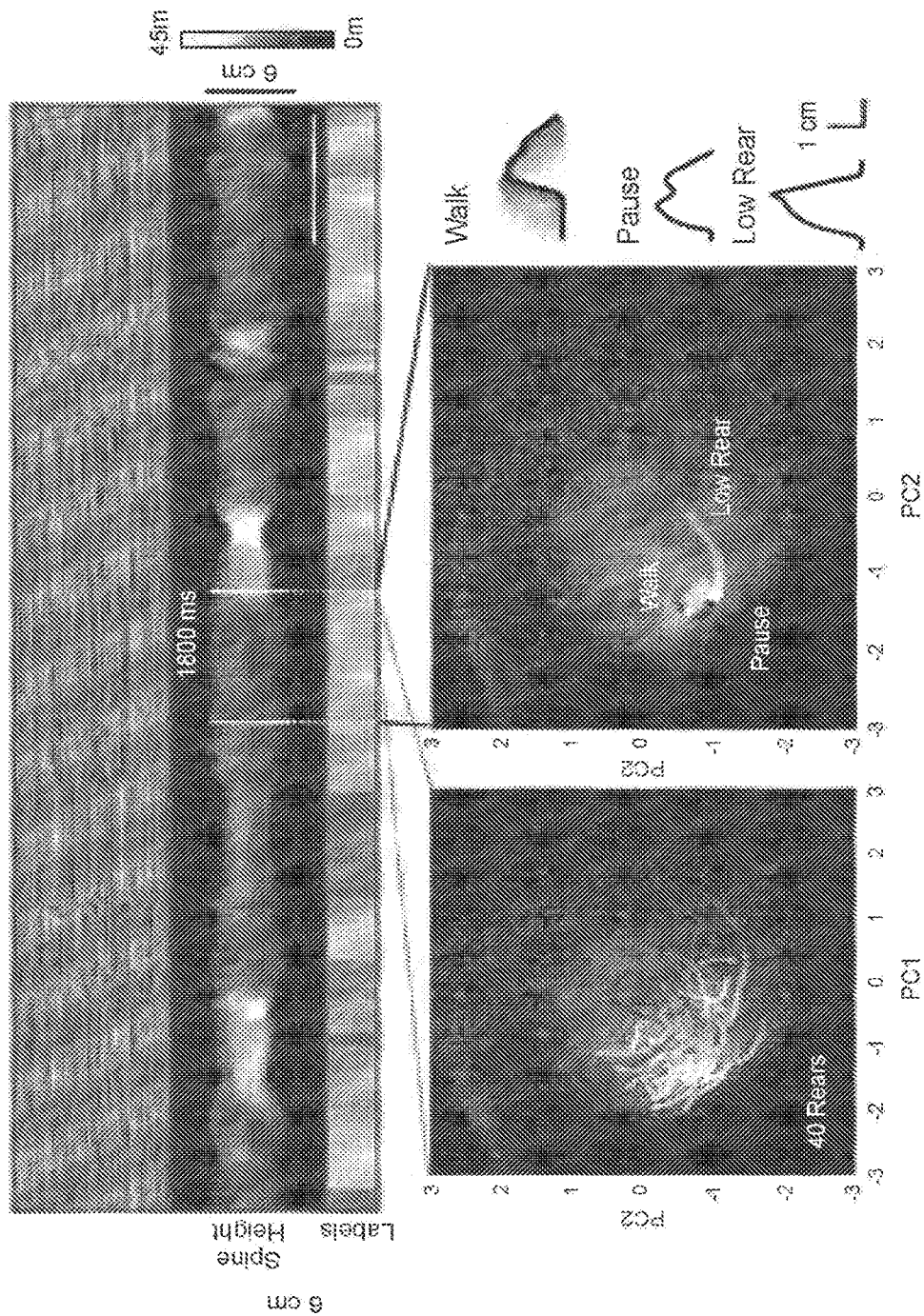
Figures 12C, 12D:
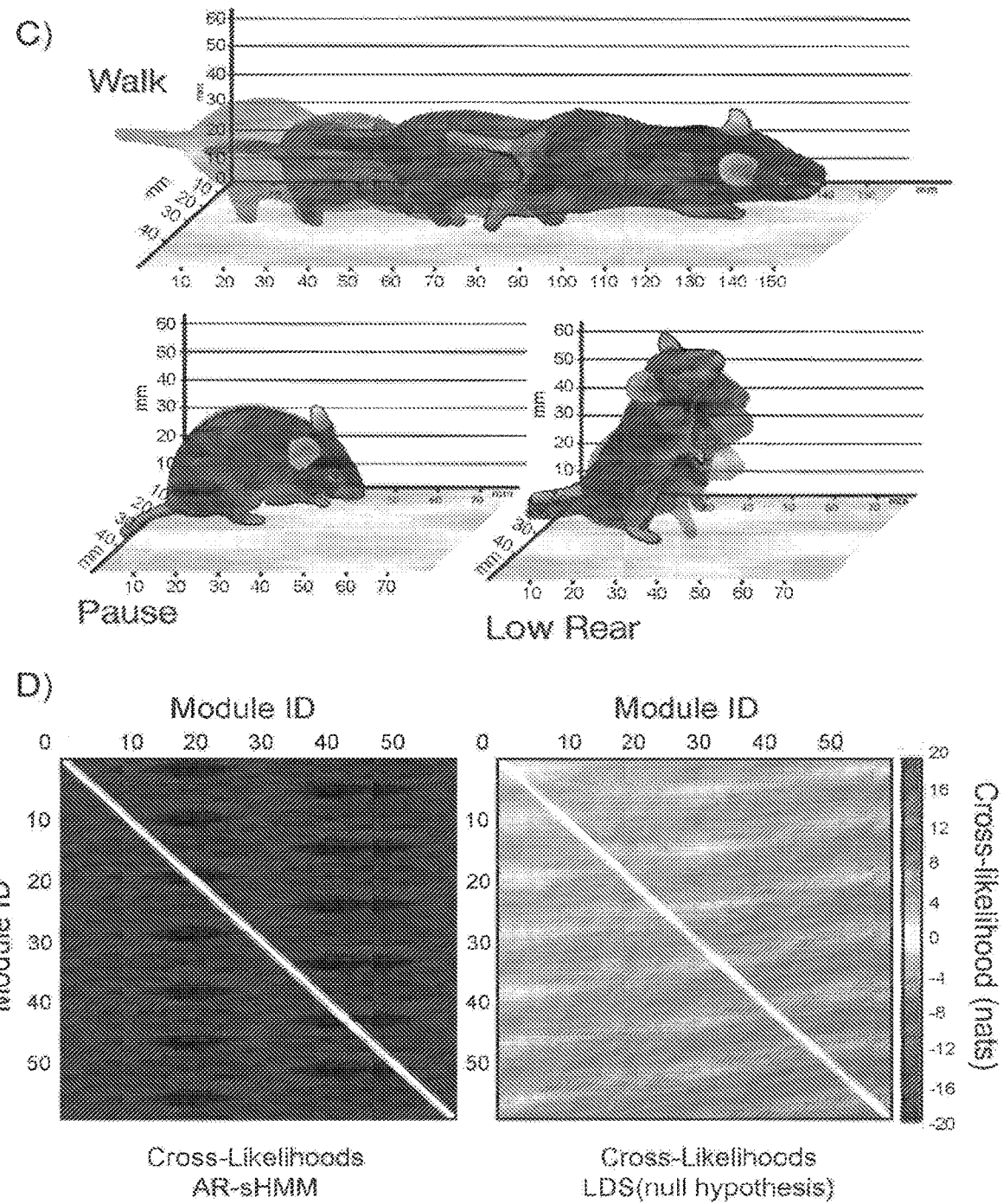
Figure 13A:
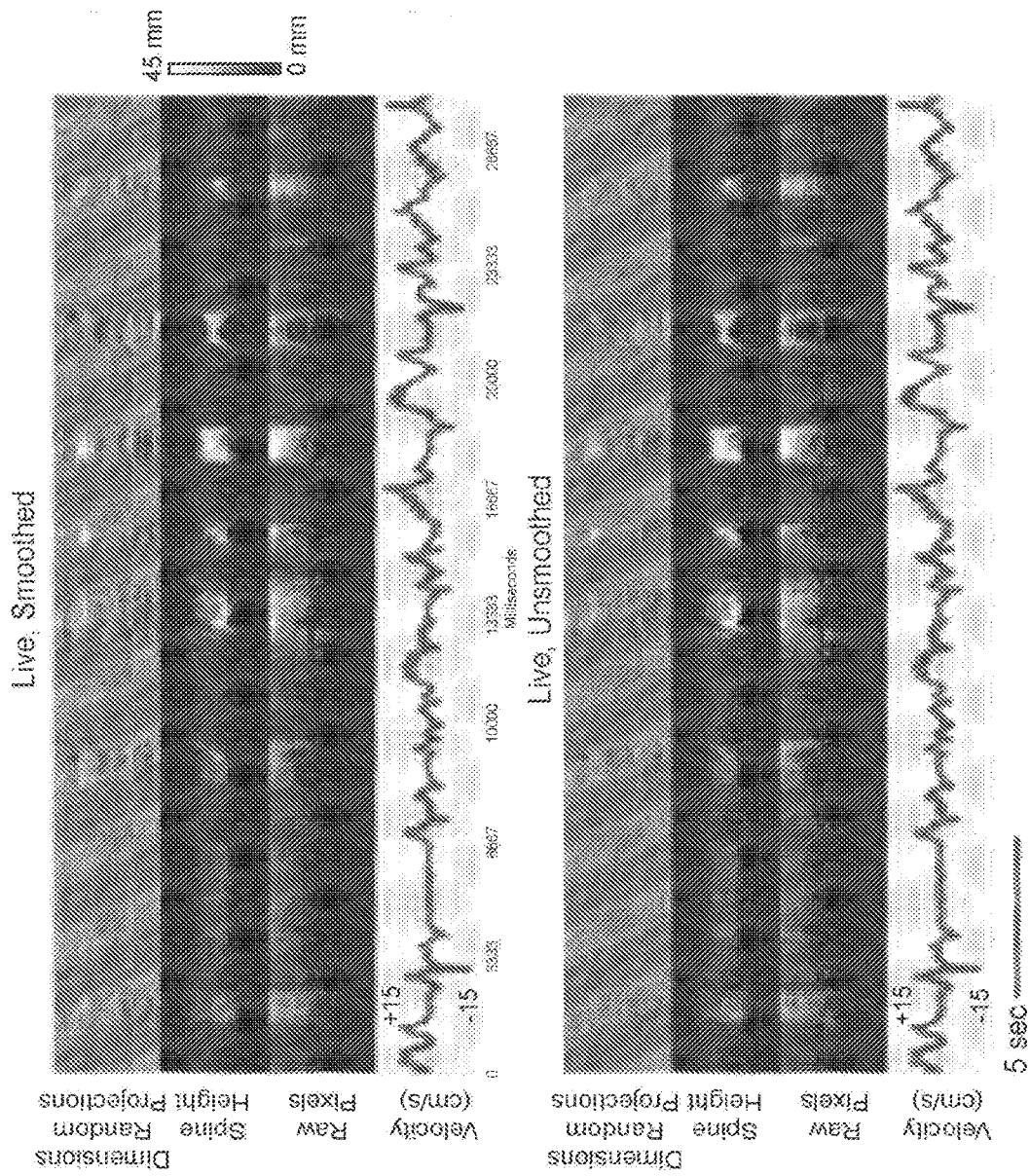
FIGS. 13Ai-13B depict, in accordance with various embodiments of the present invention, graphs illustrate block and autocorrelation structure in Mouse Depth Imaging Data.
Figure 13B:
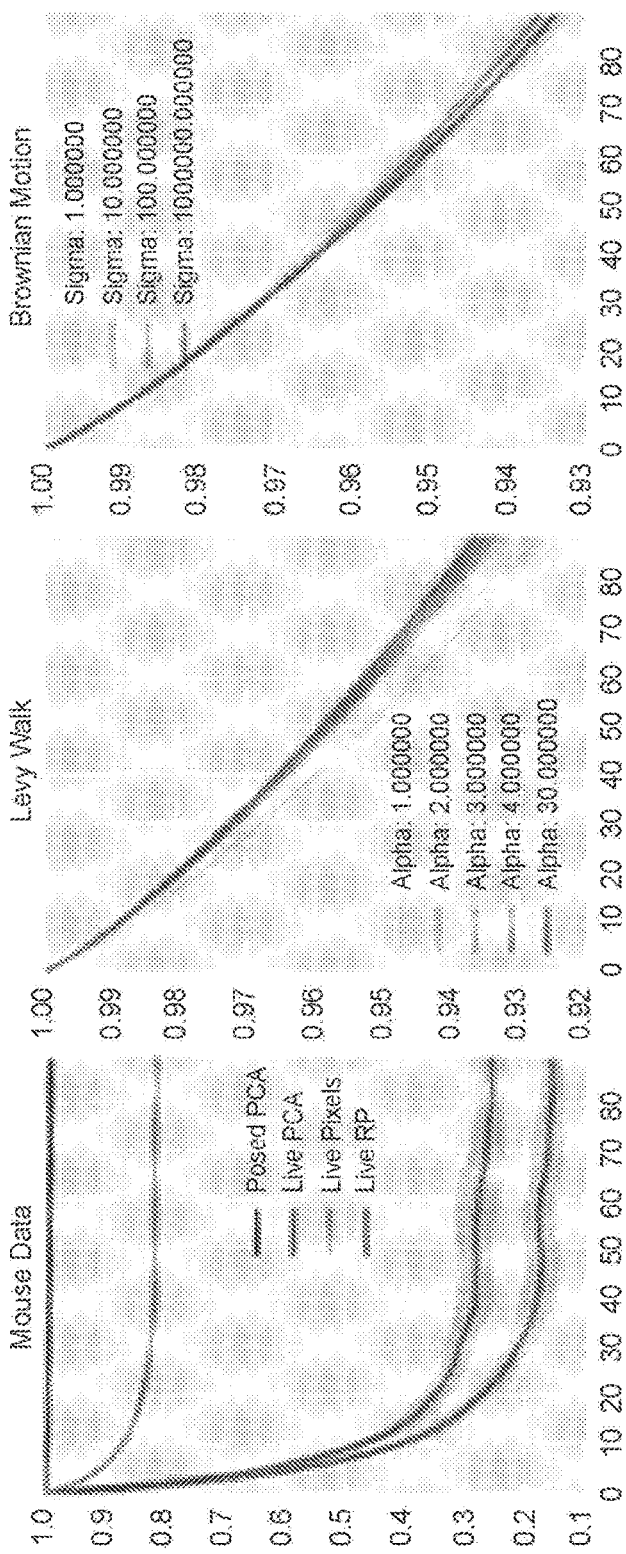
FIG. 13B illustrates that live mice exhibit significant block structure in imaging data (left panels), while dead mice do not (right panels). Compression does not significantly affect autocorrelation structure mouse pose dynamics data. Raw pixels, PCA data and random projections representing the same depth dataset (left panel) all decorrelate at approximately the same rate, demonstrating that data compression does not influence fine-timescale correlation structure in the imaging data. This correlation structure is not observed if mice poses evolve as if taking a Levy flight (middle panel) or random walk (right panel), suggesting that live mice express a specific sub-second autocorrelation structure potentially associated with switching dynamics.
Figure 14:
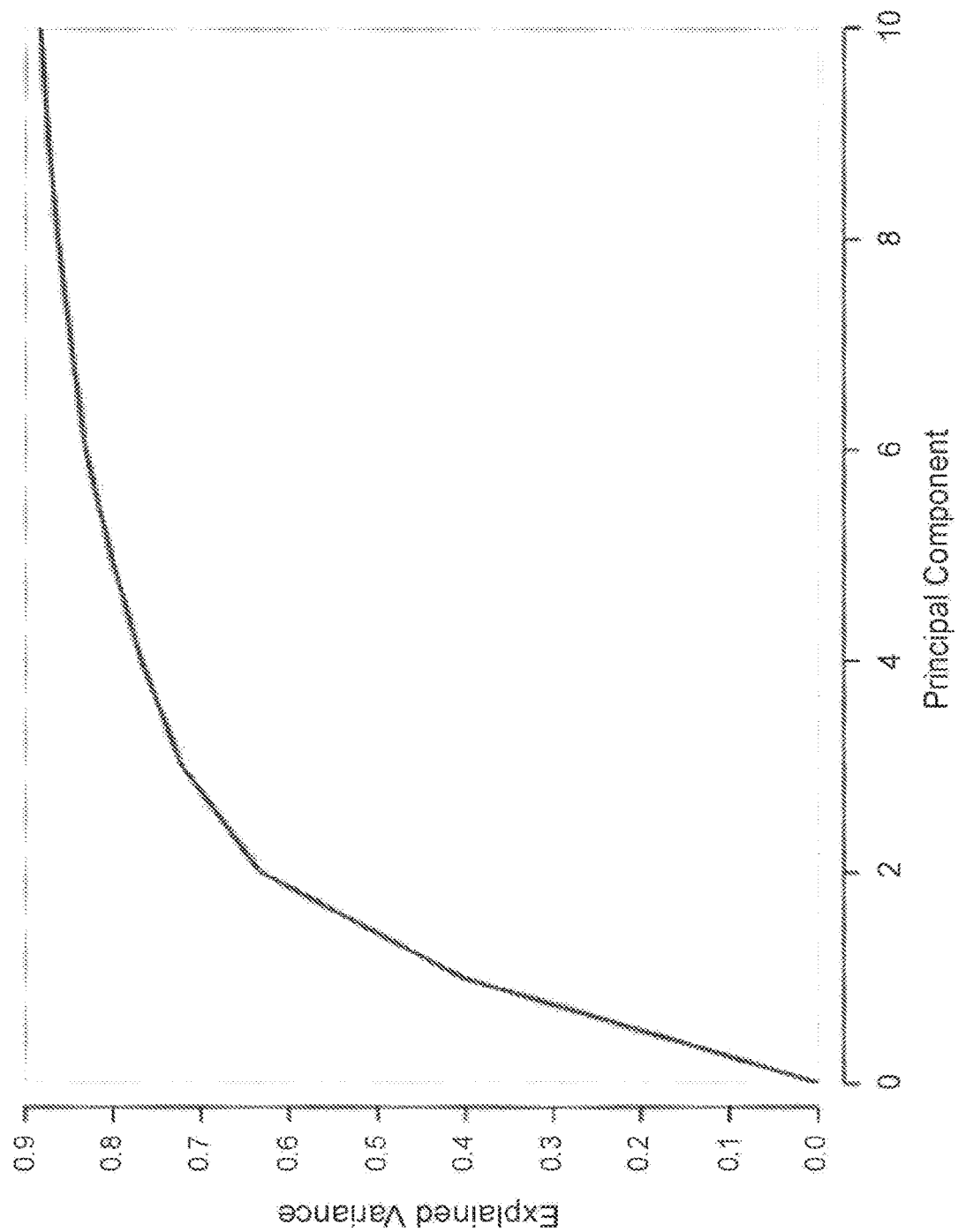
FIG. 14 depicts, in accordance with various embodiments of the present invention, a graph illustrating the variance explained after dimensional rejection using Principal Components Analysis. A Plot comparing variance explained (Y axis) with the number of included PCA dimensions (X axis) reveals that 88 percent of the variance is captured by the first 10 principal components; this number of dimensions was used for data analysis by the AR-HMM.
Figure 15A:
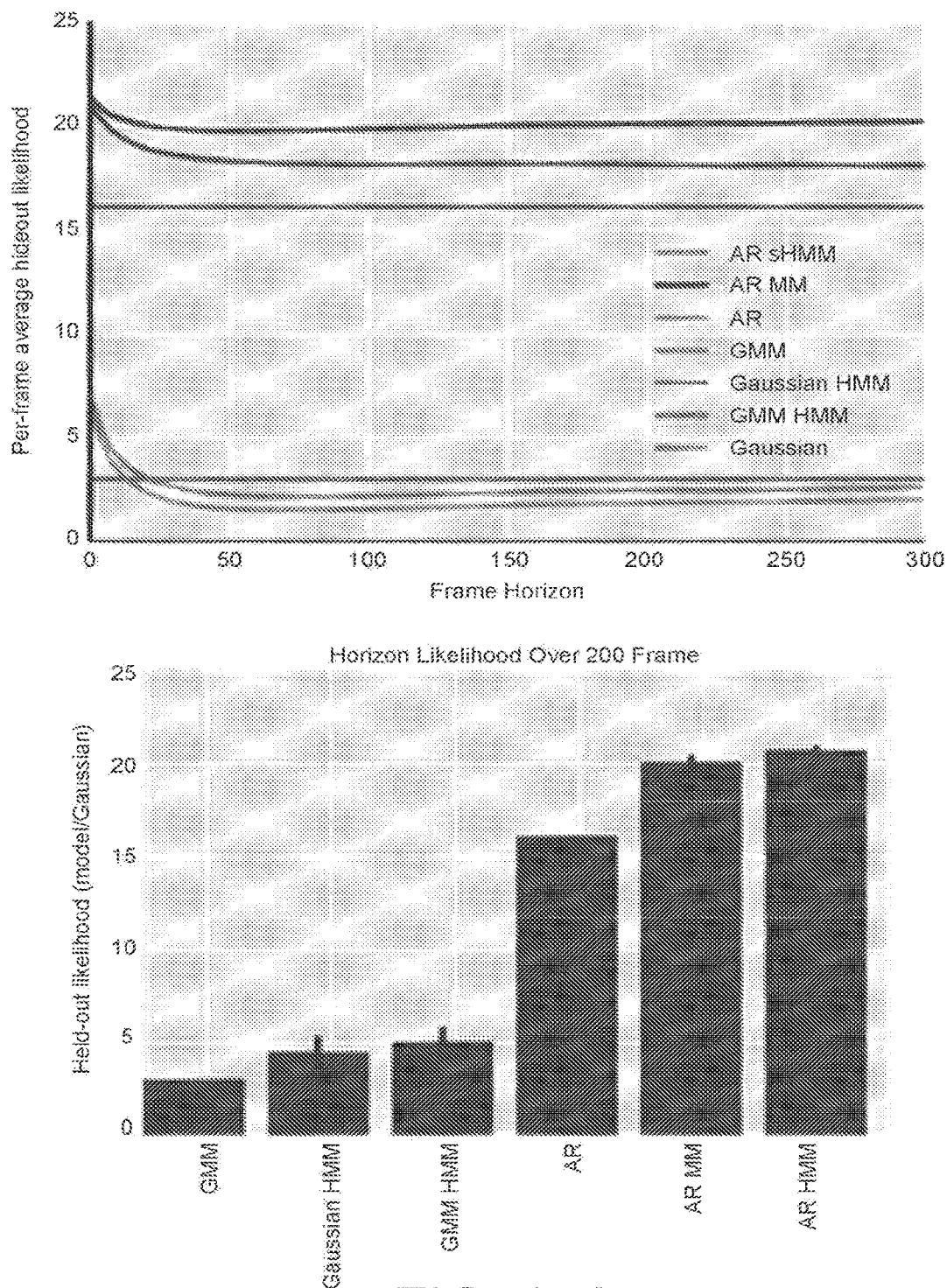
FIG. 15A-15B depicts, in accordance with various embodiments of the present invention, a graph illustrating the comparative modeling of mouse behavior. A series of computational models of behavior were composed, each instantiating a distinct hypothesis about the underlying structure of behavior, and each of these models was trained on mouse behavioral data (in the form of the top 10 principal components extracted from aligned depth data). These models included a Gaussian model (which proposes that mouse behavior is a single Gaussian in pose space), a GMM (a Gaussian Mixture Model, which proposes that mouse behavior is a mixture of Gaussians in pose space), a Gaussian HMM (a Gaussian Hidden Markov Model, which proposes that behavior created from modules, each a Gaussian in pose space, that are interconnected in time with definable transition statistics), a GMM HMM (a Gaussian Mixture Model Hidden Markov Model, which proposes that behavior created from modules, each a mixture of Gaussians in pose space, that are interconnected in time with definable transition statistics), an AR model (which proposes that mouse behavior is a single, continuous autoregressive trajectory through pose space), an AR MM (which proposes that mouse behavior is built from modules, each of which encodes a autoregressive trajectory through pose space, and which transition from one to another randomly), and a AR sHMM (which proposes that mouse behavior is built from modules, each of which encodes a autoregressive trajectory through pose space, and which transition from one to another with definable transition statistics). The performance of these models at predicting the structure of mouse behavioral data these models to which these models had not been exposed is shown on the Y axis (measured in likelihood units, and normalized to the performance of the Gaussian model), and the ability of each model to predict behavior on a frame-by-frame basis is shown on the X axis (upper). Three slices are taken through this plot at different points in time, demonstrating that the optimal AR HMM outperforms alternative models at timescales at which the switching dynamics inherent in the data come into play (e.g. after more than 10 frames, error bars are SEM).
Figure 15B:
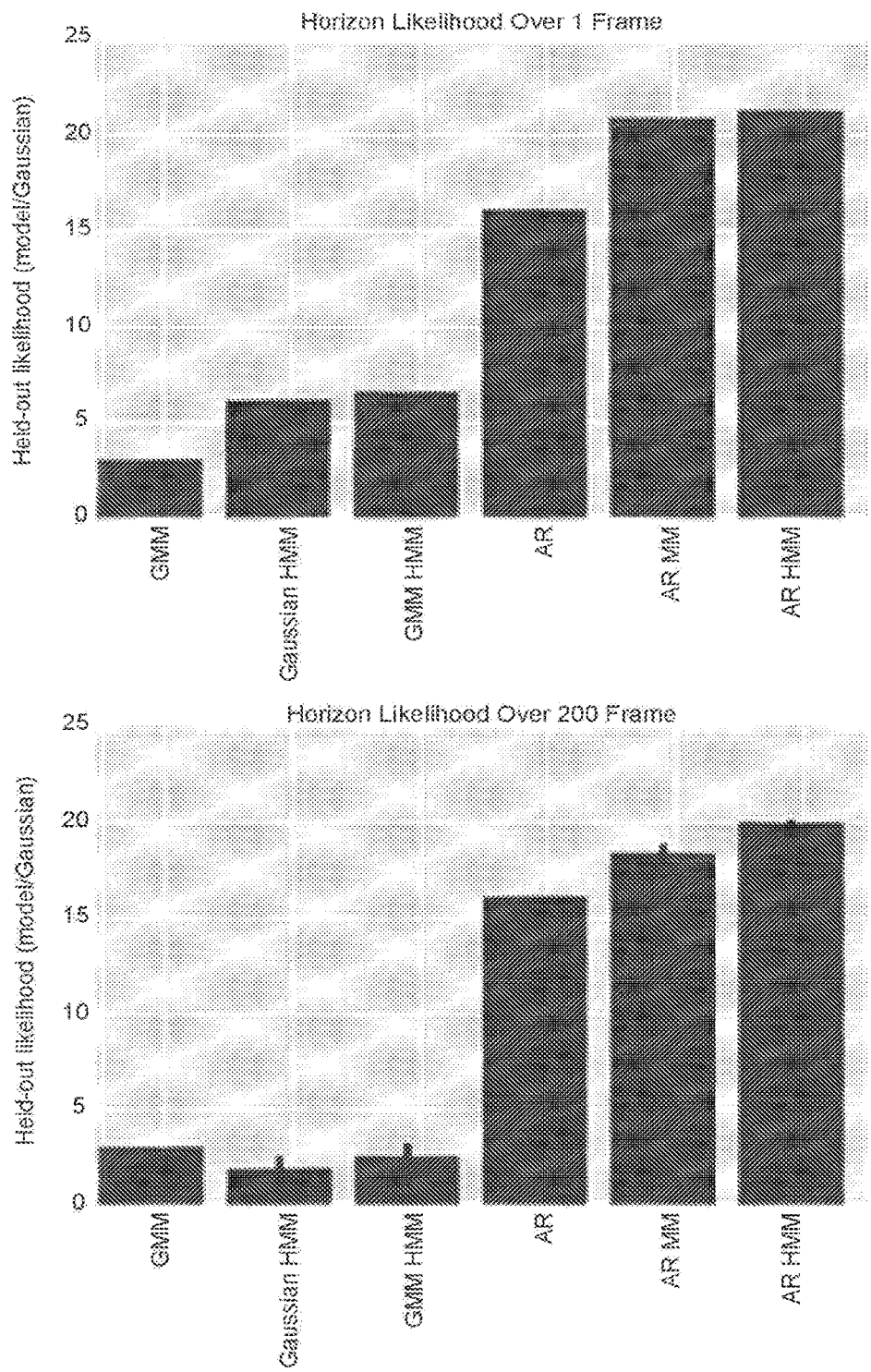
Figure 16:
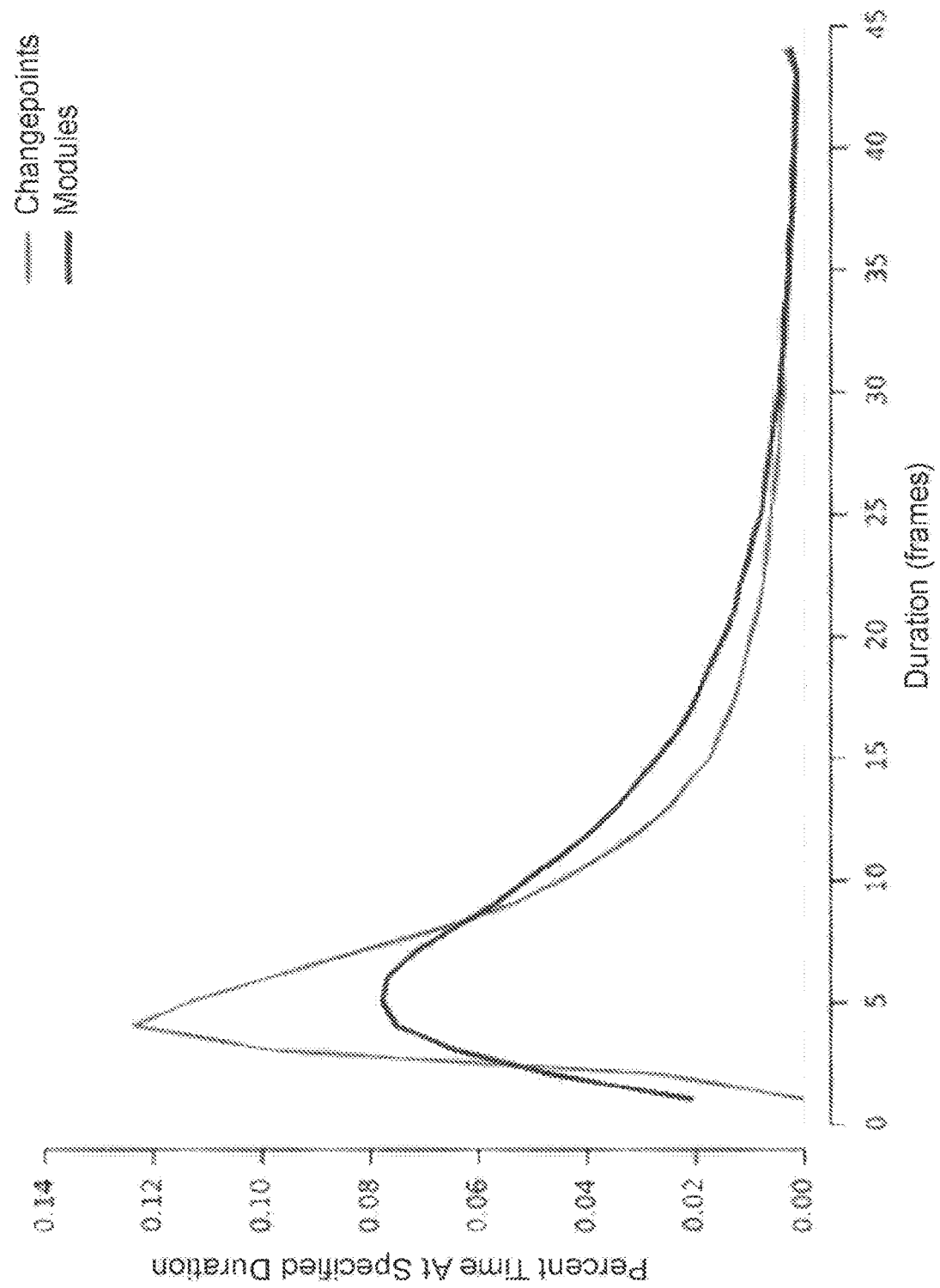
FIG. 16 depicts, in accordance with various embodiments of the present invention, a graph illustrating duration distributions for blocks and modules that are qualitatively similar. Percentage of blocks/modules of a given duration (Y axis) plotted against block duration (X axis) reveals roughly similar duration distributions for the changepoints algorithm identified blocks, and the model-identified behavioral modules. These distributions are expected to be similar although not identical, as the changepoints algorithm identifies local changes in data structure, while the model identifies modules based upon their contents and their transition statistics; note that the model has no direct access to the "local fracture" metrics used by the changepoints algorithm.
Figure 17:
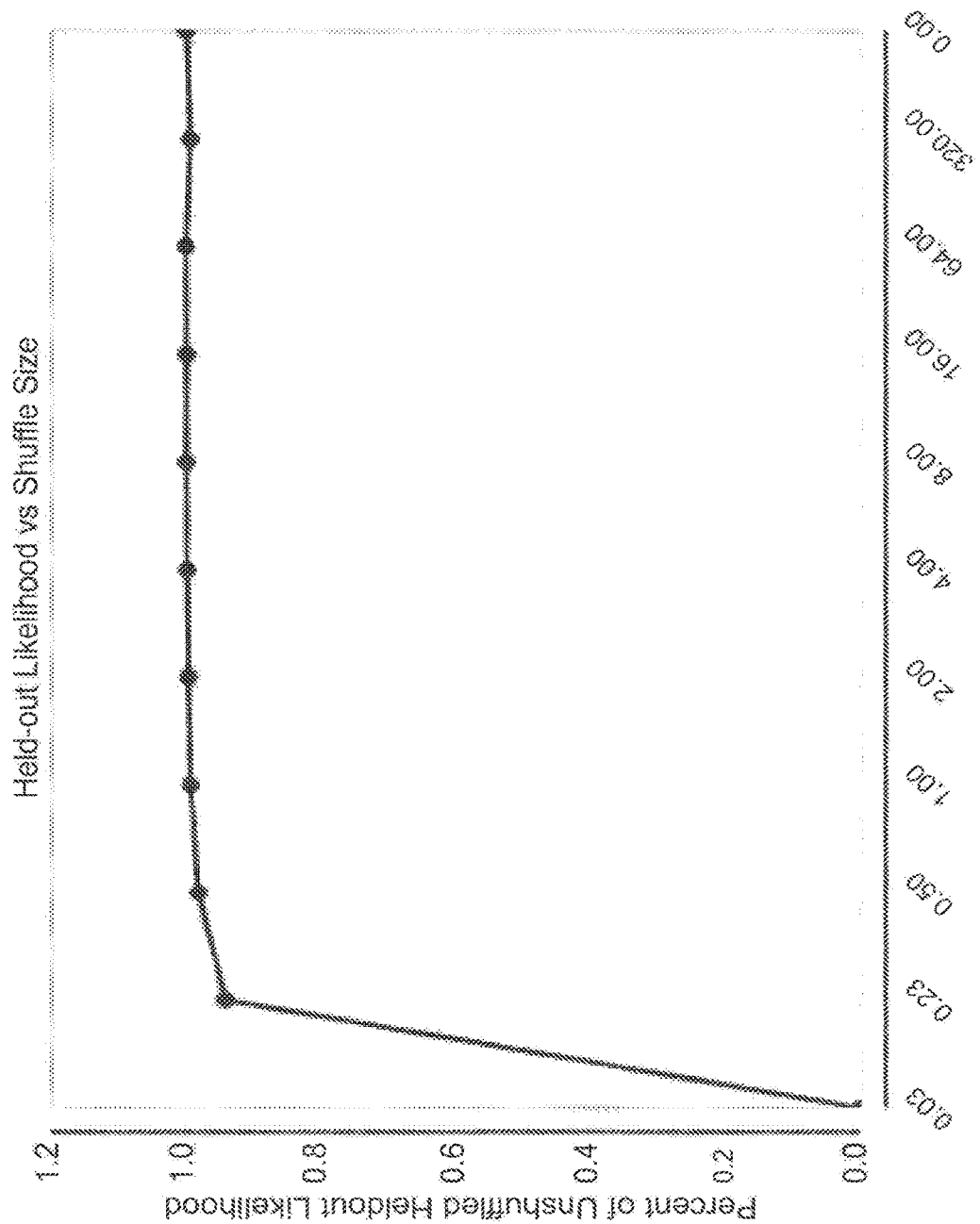
FIG. 17 depicts, in accordance with various embodiments of the present invention, a graph illustrating how shuffling behavioral data at fast timescales that lowers AR-HMM performance.
Figure 18:
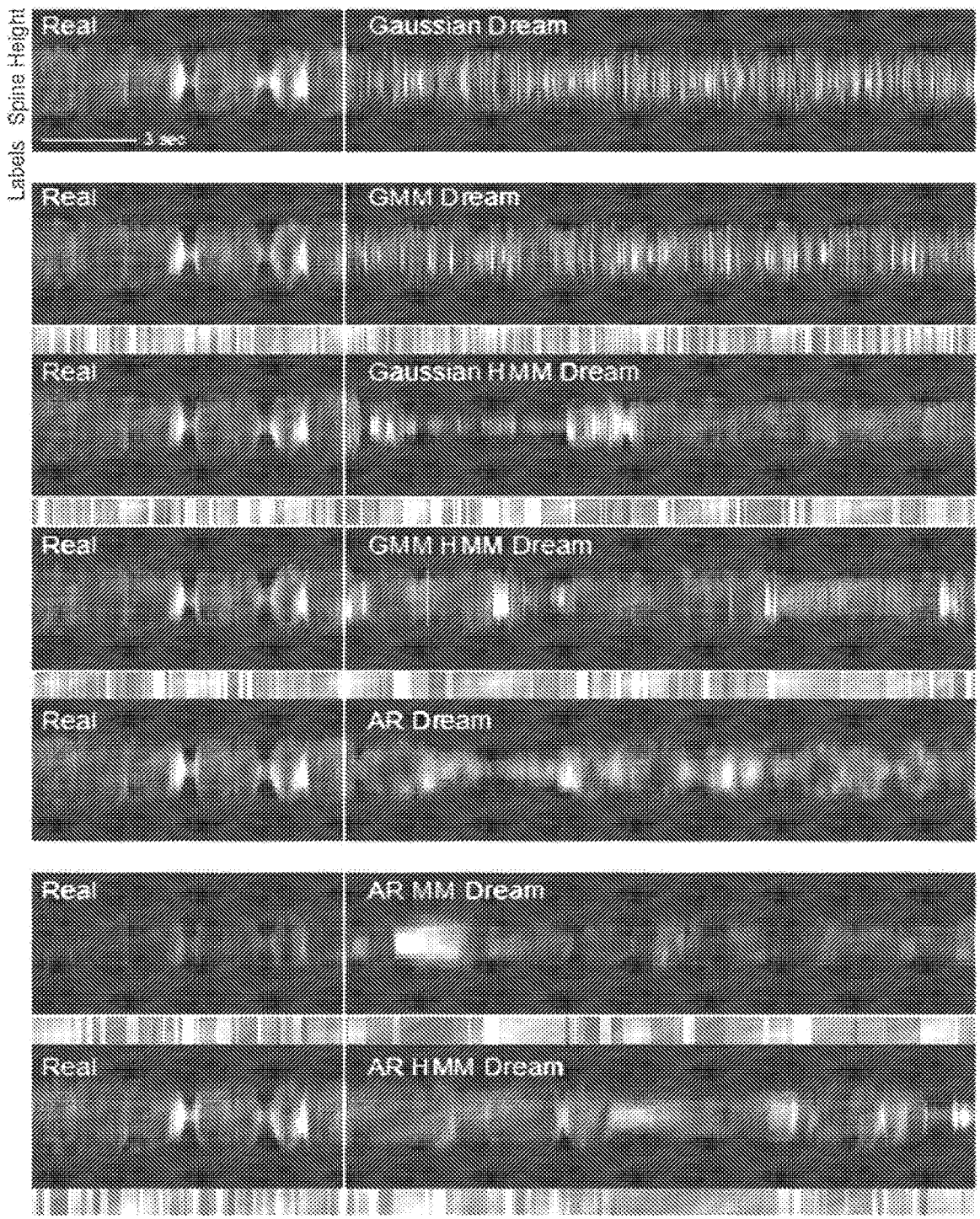
FIG. 18 depicts, in accordance with various embodiments of the present invention, graphs illustrating a visualization of model-generated mouse behavior, each of the models was trained on behavioral data (left) and then allowed to generate its "dream" version of mouse behavior (right); here that output is visualized at the shape of the spine of the animal over time. The individual modules identified by each model are indicated as a color code underneath each model (marked "labels").
Figure 19:
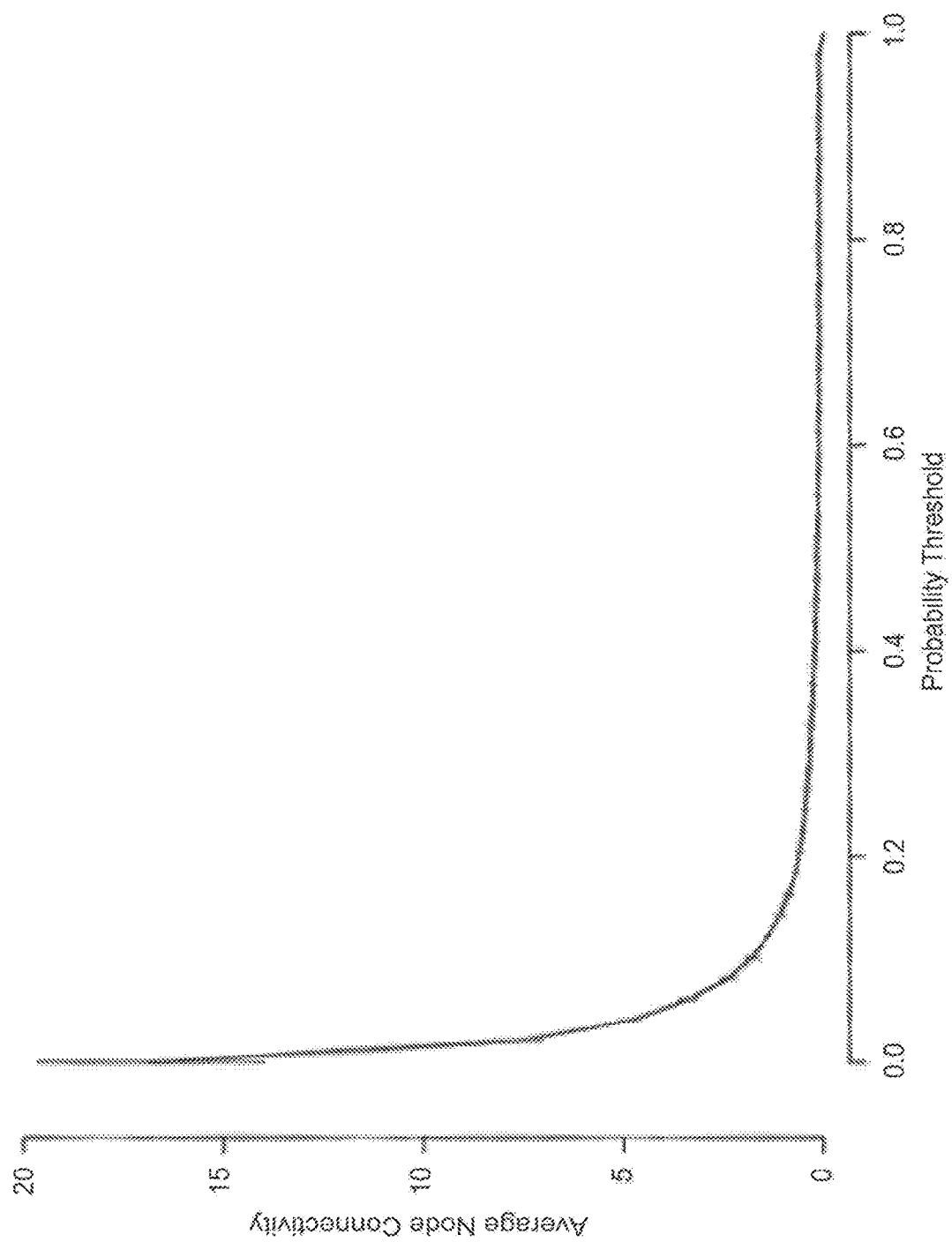
FIG. 19 depicts, in accordance with various embodiments of the present invention, a graph illustrating how module interconnectivity is sparse. Without thresholding the average module is interconnected with 16.85±0.95 other modules; this modest interconnectivity falls sharply with even modest thresholding (X axis, thresholding applied to bigram probabilities), consistent with sparse temporal interconnectivity between individual behavioral modules.
Figure 20:
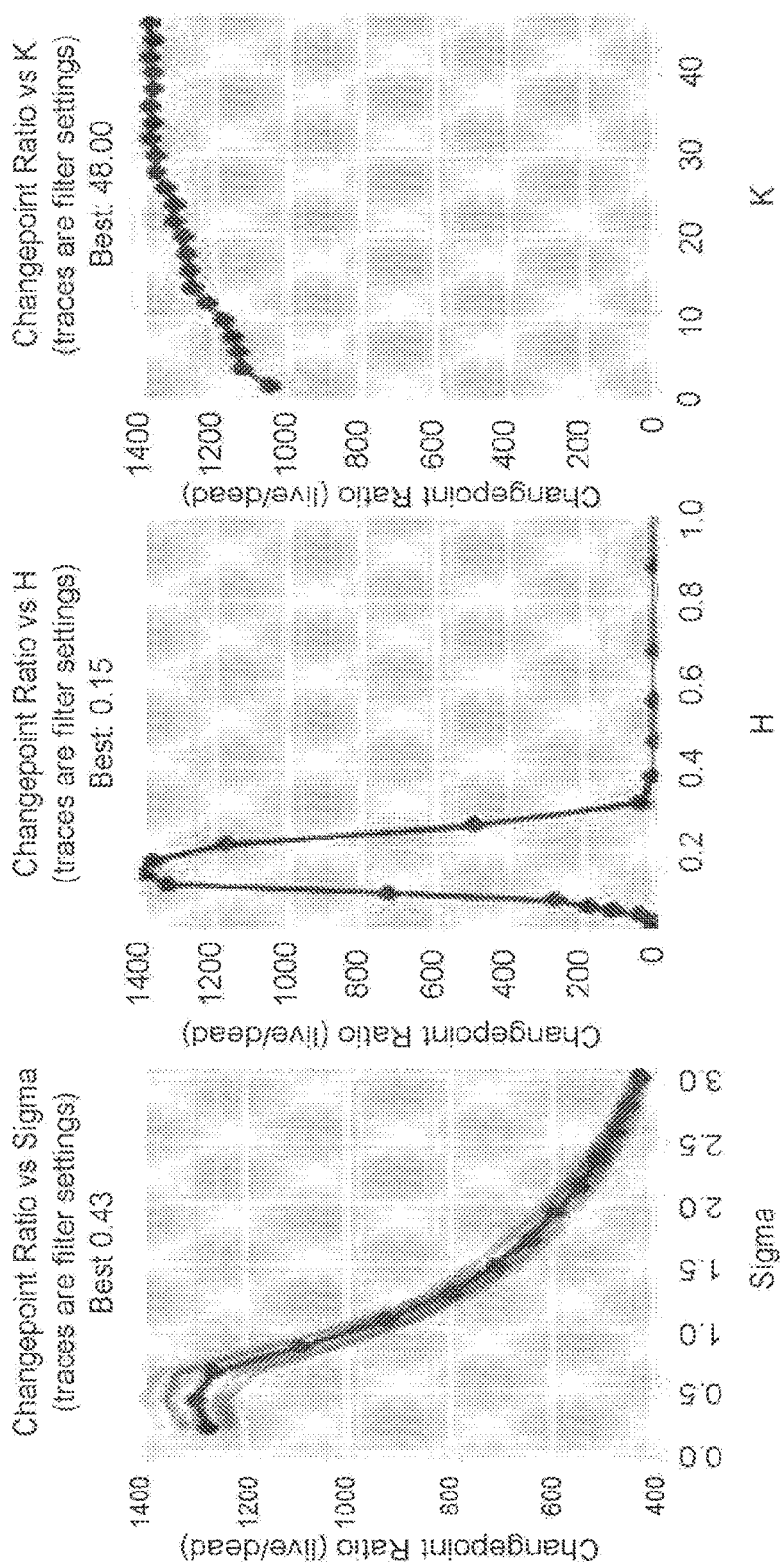
FIG. 20 depicts, in accordance with various embodiments of the present invention, graphs illustrating the identification of the filtering parameters. To filter data from the Kinect we used iterative an iterative median filtering approach in which we applied a median filter iteratively both in space and in time; this approach has been shown to effectively maintain data structure while smoothing away noise. To identify optimal filter settings, we imaged dead mice that were differentially posed in rigor mortis; ideal filter settings would distinguish mice that were posed differently, but be unable to distinguish data from the same mouse. Filter setting are indicated as ((pixels), (frames)) with the numbers within each parenthesis referring to the iterative settings for each round of filtering. To assess filter performance, we computed a within/between pose correlation ratio (Y axis), in which the mean spatial correlation for all frames of the same pose was divided by the mean spatial correlation for all frames of different poses. This revealed that light filtering (with settings ((3), (3,5))) optimized discriminability in the data.
Figure 21:
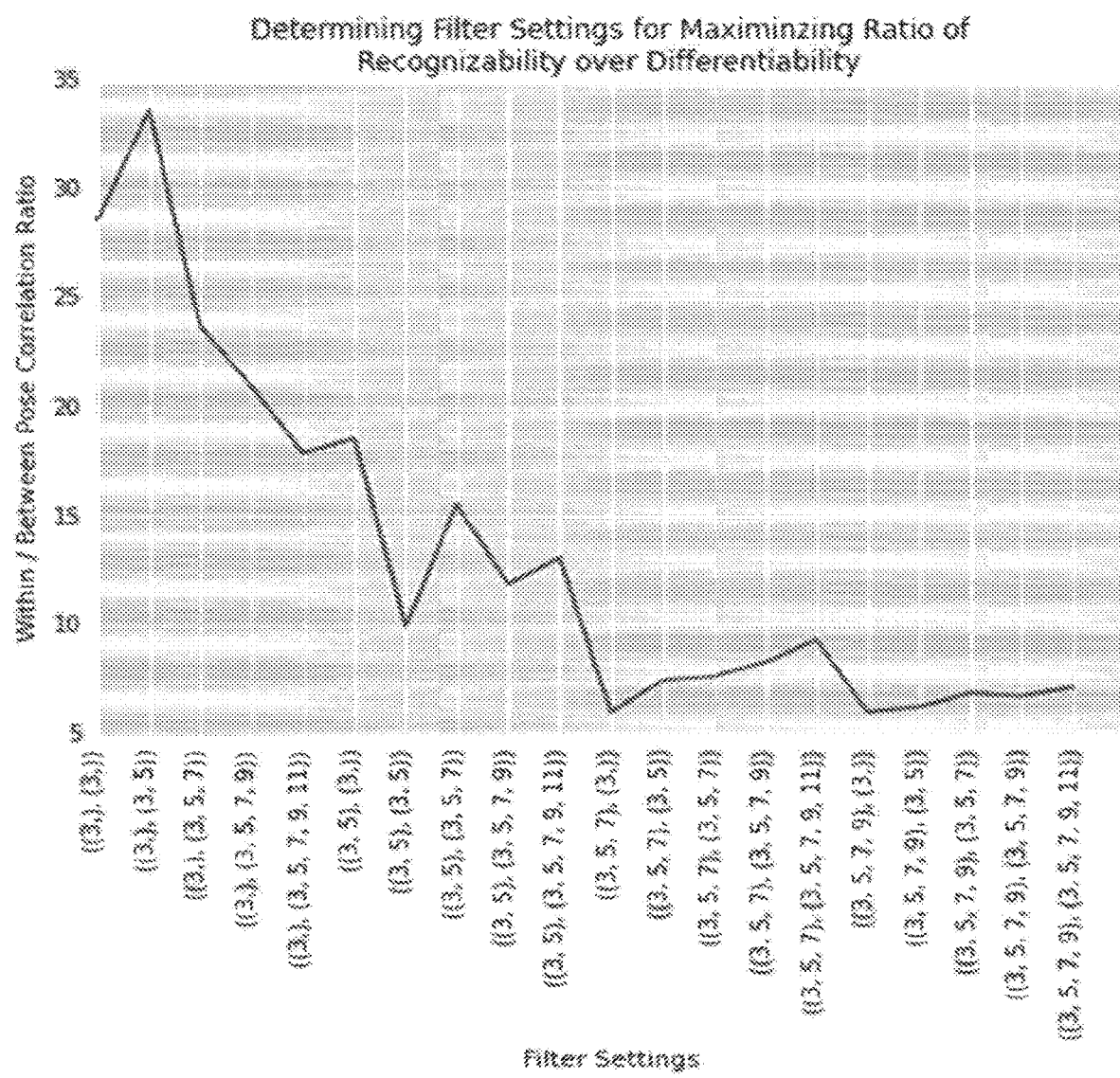
FIG. 21 depicts, in accordance with various embodiments of the present invention, a graph identifying changepoint algorithm parameters. By optimizing against the changepoints ratio (number of changepoints identified in live mice versus dead mice, Y axis), clear optimal values were identified via grid scanning for sigma and H (left two panels).

At the lowest power levels no light-induced changes in behavior were observed, while at the highest power levels the AR-HMM identified two behavioral modules whose expression was reliably induced by the light (FIG. 10A). Neither of these modules were expressed during normal mouse locomotion; inspection revealed them to encode two forms of spinning behavior (differing in their length and the angle of turn), in which the mouse traces out semi-circles or donuts in space (FIG. 10B). The induction of neomorphic behaviors after strong unilateral motor cortex stimulation is not surprising, although it is important to note that the AR-HMM both recognized these behaviors as new and encapsulated them as two unique behavioral modules. However, we noted that approximately 40 percent of the time, the overall pattern of behavior did not return to baseline for several seconds after light offset. This deviation from baseline was not due to continued expression of the modules triggered at light onset; instead, mice often expressed a pausing module (average during-module velocity=$0.8 \pm 7$ mm/sec) at light offset as if "resetting" after a non-volitional movement.

The behavioral changes induced by high intensity optogenetic stimulation were reliable, as on essentially every trial the animal emitted one of the two spinning modules. We then asked whether the sensitivity of the AR-HMM would enable quantitative analysis of more subtle changes in behavior, as occurs in intermediate regimes of motor cortex stimulation that elicit unreliable emission of specific behavioral modules. The inventors therefore titrated the levels of light stimulation down until one of the two neomorphic behavioral modules was no longer detected, and the other was expressed on only 25 percent of trials. Surprisingly, we were then could detect the upregulation of a second set of behavioral modules, each of which was expressed about 25 percent of the time (FIG. 10A). These modules were not neomorphic, but rather were normally expressed during physiological exploration, and encoded a turn and a head-bobbing behavior (data not shown). While each of these individual light-regulated modules was emitted unreliably, taken in aggregate the behavioral changes across all modules suggested that lower-level neural activation reliably influenced behavior, but largely through inducing physiological rather than neomorphic actions (FIG. 10A). Taken together, the detection of both stimulus-locked induction of behavioral modules and the lingering effects of stimulation of module usage demonstrates that neurally-induced changes in behavior can influence the sub-second structure of behavior. Furthermore, the identification of a physiologically-expressed set of light-regulated behavioral modules—whose induction would not have been apparent under strong stimulation conditions—also suggests that the AR-HMM can reveal subtle relationships between neural circuits and the time-series structure of behavior.

Computer & Hardware Implementation of Disclosure

It should initially be understood that the disclosure herein may be implemented with any type of hardware and/or software, and may be a pre-programmed general purpose computing device. For example, the system may be implemented using a server, a personal computer, a portable computer, a thin client, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessary represent specific hardware or software. In this regard, these modules may be hardware and/or software implemented to substantially perform the particular functions discussed. Moreover, the modules may be combined together within the disclosure, or divided into additional modules based on the particular function desired. Thus, the disclosure should not be construed to limit the present invention, but merely be understood to illustrate one example implementation thereof.

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a "data processing apparatus" on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

REFERENCES

1 Fettiplace, R. & Fuchs, P. A. Mechanisms of hair cell tuning. *Annual review of physiology* 61, 809-834, (1999).
2 Fettiplace, R. & Kim, K. X. The Physiology of Mechanoelectrical Transduction Channels in Hearing. *Physiological reviews* 94, 951-986, (2014).
3 Gollisch, T. & Herz, A. M. V. Disentangling Sub-Millisecond Processes within an Auditory Transduction Chain. *PLoS Biology* 3, e8, (2005).
4 Kawasaki, M., Rose, G. & Heiligenberg, W. Temporal hyperacuity in single neurons of electric fish. *Nature* 336, 173-176, (1988).
5 Nemenman, I., Lewen, G. D., Bialek, W. & de Ruyter van Steveninck, R. R. Neural Coding of Natural Stimuli: Information at Sub-Millisecond Resolution. *PLoS computational biology* 4, e1000025, (2008).
6 Peters, A. J., Chen, S. X. & Komiyama, T. Emergence of reproducible spatiotemporal activity during motor learning. *Nature* 510, 263-267, (2014).
7 Ritzau-Jost, A., Delvendahl, I., Rings, A., Byczkowicz, N., Harada, H., Shigemoto, R., Hirrlinger, J., Eilers, J. & Hallermann, S. Ultrafast Action Potentials Mediate Kilohertz Signaling at a Central Synapse. *Neuron* 84, 152-163, (2014).
8 Shenoy, K. V., Sahani, M. & Churchland, M. M. Cortical Control of Arm Movements: A Dynamical Systems Perspective. *Annual review of neuroscience* 36, 337-359, (2013).
9 Bargmann, C. I. Beyond the connectome: How neuromodulators shape neural circuits. *BioEssays* 34, 458-465, (2012).

10 Tinbergen, N. *The study of instinct.* (Clarendon Press, 1951).
11 Garrity, P. A., Goodman, M. B., Samuel, A. D. & Sengupta, P. Running hot and cold: behavioral strategies, neural circuits, and the molecular machinery for thermotaxis in C. elegans and Drosophila. *Genes & Development* 24, 2365-2382, (2010).
12 Stephens, G. J., Johnson-Kerner, B., Bialek, W. & Ryu, W. S. Dimensionality and Dynamics in the Behavior of C. elegans. *PLoS computational biology* 4, e1000028, (2008).
13 Stephens, G. J., Johnson-Kerner, B., Bialek, W. & Ryu, W. S. From Modes to Movement in the Behavior of Caenorhabditis elegans. *PLoS ONE* 5, e13914, (2010).
14 Vogelstein, J. T., Vogelstein, J. T., Park, Y., Park, Y., Ohyama, T., Kerr, R. A., Kerr, R. A., Truman, J. W., Truman, J. W., Priebe, C. E., Priebe, C. E., Zlatic, M. & Zlatic, M. Discovery of brainwide neural-behavioral maps via multiscale unsupervised structure learning. *Science* (New York, NY) 344, 386-392, (2014).
15 Berman, G. J., Choi, D. M., Bialek, W. & Shaevitz, J. W. *Mapping the structure of drosophilid behavior.* (2013).
16 Croll, N. A. Components and patterns in the behaviour of the nematode Caenorhabditis elegans. *Journal of zoology* 176, 159-176, (1975).
17 Pierce-Shimomura, J. T., Morse, T. M. & Lockery, S. R. The fundamental role of pirouettes in Caenorhabditis elegans chemotaxis. *Journal of Neuroscience* 19, 9557-9569, (1999).
18 Gray, J. M., Hill, J. J. & Bargmann, C. I. A circuit for navigation in Caenorhabditis elegans. *Proceedings of the National Academy of Sciences of the United States of America* 102, 3184-3191, (2005).
19 Miller, A. C., Thiele, T. R., Faumont, S., Moravec, M. L. & Lockery, S. R. Step-response analysis of chemotaxis in Caenorhabditis elegans. *Journal of Neuroscience* 25, 3369-3378, (2005).
20 Jhuang, H., Garrote, E., Yu, X., Khilnani, V., Poggio, T., Steele, A. D. & Serre, T. Automated home-cage behavioural phenotyping of mice. *Nature Communications* 1, 68, (2010).
21 Stewart, A., Liang, Y., Kobla, V. & Kalueff, A. V. Towards high-throughput phenotyping of complex patterned behaviors in rodents: Focus on mouse self-grooming and its sequencing. *Behavioural brain . . .*, (2011).
22 Ohayon, S., Avni, O., Taylor, A. L., Perona, P. & Egnor, S. E. R. Automated multi-day tracking of marked mice for the analysis of social behavior. *Journal of neuroscience methods,* 1-25, (2013).
23 de Chaumont, F., Coura, R. D.-S., Serreau, P., Cressant, A., Chabout, J., Granon, S. & Olivo-Marin, J.-C. Computerized video analysis of social interactions in mice. *Nature Methods* 9, 410-417, (2012).
24 Kabra, M., Robie, A. A., Rivera-Alba, M., Branson, S. & Branson, K. JAABA: interactive machine learning for automatic annotation of animal behavior. *Nature Methods* 10, 64-67, (2013).
25 Weissbrod, A., Shapiro, A., Vasserman, G., Edry, L., Dayan, M., Yitzhaky, A., Hertzberg, L., Feinerman, O. & Kimchi, T. Automated long-term tracking and social behavioural phenotyping of animal colonies within a semi-natural environment. *Nature Communications* 4, 2018, (2013).
26 Spink, A. J., Tegelenbosch, R. A., Buma, M. O. & Noldus, L. P. The EthoVision video tracking system—a tool for behavioral phenotyping of transgenic mice. *Physiology & behavior* 73, 731-744, (2001).
27 Tort, A. B. L., Neto, W. P., Amaral, O. B., Kazlauckas, V., Souza, D. O. & Lara, D. R. A simple webcam-based approach for the measurement of rodent locomotion and other behavioural parameters. *Journal of neuroscience methods* 157, 91-97, (2006).
28 Gomez-Marin, A., Partoune, N., Stephens, G. J., Louis, M. & Brembs, B. Automated tracking of animal posture and movement during exploration and sensory orientation behaviors. *PLoS ONE* 7, e41642, (2012).
29 Colgan, P. W. Quantitative ethology. (John Wiley & Sons, 1978).
30 Fox, E. B., Sudderth, E. B., Jordan, M. I. & Willsky, A. S. in *Proc. International Conference on Machine Learning* (2008).
31 Fox, E. B., Sudderth, E. B., Jordan, M. I. & Willsky, A. S. Bayesian Nonparametric Inference of Switching Dynamic Linear Models. *IEEE Transactions on Signal Processing* 59, (2011).
32 Johnson, M. J. & Willsky, A. S. The Hierarchical Dirichlet Process Hidden Semi-Markov Model. *Arxiv* abs/1203.3485, (2012).
33 Teh, Y. W., Jordan, M. I. & Beal, M. J. Hierarchical dirichlet processes. *Journal of the american . . .*, (2006).
34 Geman, S. & Geman, D. Stochastic Relaxation, Gibbs Distributions, and the Bayesian Restoration of Images. *IEEE Trans. Pattern Anal. Mach. Intell.* 6, 721-741, (1984).
35 Wallace, K. J. & Rosen, J. B. Predator odor as an unconditioned fear stimulus in rats: elicitation of freezing by trimethylthiazoline, a component of fox feces. *Behav Neurosci* 114, 912-922, (2000).
36 Fendt, M., Endres, T., Lowry, C. A., Apfelbach, R. & McGregor, I. S. TMT-induced autonomic and behavioral changes and the neural basis of its processing. *Neurosci Biobehav Rev* 29, 1145-1156, (2005).
37 André, E., Conquet, F., Steinmayr, M., Stratton, S. C., Porciatti, V. & Becker-André, M. Disruption of retinoid-related orphan receptor beta changes circadian behavior, causes retinal degeneration and leads to vacillans phenotype in mice. *The EMBO journal* 17, 3867-3877, (1998).
38 Liu, H., Kim, S.-Y., Fu, Y., Wu, X., Ng, L., Swaroop, A. & Forrest, D. An isoform of retinoid-related orphan receptor β directs differentiation of retinal amacrine and horizontal interneurons. *Nature Communications* 4, 1813, (2013).
39 Eppig, J. T., Blake, J. A., Bult, C. J., Kadin, J. A., Richardson, J. E. & Group, M. G. D. The Mouse Genome Database (MGD): facilitating mouse as a model for human biology and disease. *Nucleic Acids Research* 43, D726-736, (2015).
40 Masana, M. I., Sumaya, I. C., Becker-Andre, M. & Dubocovich, M. L. Behavioral characterization and modulation of circadian rhythms by light and melatonin in C3H/HeN mice homozygous for the RORbeta knockout. *American journal of physiology. Regulatory, integrative and comparative physiology* 292, R2357-2367, (2007).
41 Glickfeld, L. L., Andermann, M. L., Bonin, V. & Reid, R. C. Cortico-cortical projections in mouse visual cortex are functionally target specific. *Nature Neuroscience* 16, 219-226, (2013).
42 Mei, Y. & Zhang, F. Molecular tools and approaches for optogenetics. *Biological psychiatry* 71, 1033-1038, (2012).
43 Lashley, K. S. (ed Lloyd A Jeffress) (Psycholinguistics: A book of readings, 1967).

44 Sherrington, C. The Integrative Action of the Nervous System. *The Journal of Nervous and Mental Disease*, (1907).

45 Bizzi, E., Tresch, M. C., Saltiel, P. & d' Avella, A. New perspectives on spinal motor systems. *Nature Reviews Neuroscience* 1, 101-108, (2000).

46 Drai, D., Benjamini, Y. & Golani, I. Statistical discrimination of natural modes of motion in rat exploratory behavior. *Journal of neuroscience methods* 96, 119-131, (2000).

47 Brown, T. G. in *Proceedings of the Royal Society of London Series B* (1911).

48 Crawley, J. N. Behavioral phenotyping of rodents. *Comparative medicine* 53, 140-146, (2003).

49 Anderson, D. J. & Perona, P. Toward a science of computational ethology. *Neuron* 84, 18-31, (2014).

50 Berg, H. C. & Brown, D. A. Chemotaxis in *Escherichia coli* analysed by three-dimensional tracking. *Nature* 239, 500-504, (1972).

51 Berg, H. C. Chemotaxis in bacteria. *Annual review of biophysics and bioengineering* 4, 119-136, (1975).

52 Berg, H. C. Bacterial behaviour. *Nature* 254, 389-392, (1975).

53 Hong, W., Kim, D.-W. & Anderson, D. J. Antagonistic Control of Social versus Repetitive Self-Grooming Behaviors by Separable Amygdala Neuronal Subsets. *Cell* 158, 1348-1361, (2014).

54 Lin, D., Boyle, M. P., Dollar, P., Lee, H., Lein, E. S., Perona, P. & Anderson, D. J. Functional identification of an aggression locus in the mouse hypothalamus. *Nature* 470, 221-226, (2011).

55 Swanson, L. W. Cerebral hemisphere regulation of motivated behavior. *Brain research* 886, 113-164, (2000).

56 Aldridge, J. W. & Berridge, K. C. Coding of serial order by neostriatal neurons: a " natural action" approach to movement sequence. *The Journal of neuroscience: the official journal of the Society for Neuroscience* 18, 2777-2787, (1998).

57 Aldridge, J. W., Berridge, K. C. & Rosen, A. R. Basal ganglia neural mechanisms of natural movement sequences. *Canadian Journal of Physiology and Pharmacology* 82, 732-739, (2004).

58 Jin, X., Tecuapetla, F. & Costa, R. M. Basal ganglia subcircuits distinctively encode the parsing and concatenation of action sequences. *Nature Publishing Group* 17, 423-430, (2014).

59 Tresch, M. C. & Jarc, A. The case for and against muscle synergies. *Current opinion in neurobiology* 19, 601-607, (2009).

60 Flash, T. & Hochner, B. Motor primitives in vertebrates and invertebrates. *Current opinion in neurobiology* 15, 660-666, (2005).

61 Bizzi, E., Cheung, V. C. K., d' Avella, A., Saltiel, P. & Tresch, M. Combining modules for movement. *Brain Research Reviews* 57, 125-133, (2008).

62 Tresch, M. C., Saltiel, P. & Bizzi, E. The construction of movement by the spinal cord. *Nature Neuroscience* 2, 162-167, (1999).

63 Berwick, R. C., Okanoya, K., Beckers, G. J. L. & Bolhuis, J. J. Songs to syntax: the linguistics of birdsong. *Trends in cognitive sciences* 15, 113-121, (2011).

64 Wohlgemuth, M. J., Sober, S. J. & Brainard, M. S. Linked control of syllable sequence and phonology in birdsong. *Journal of Neuroscience* 30, 12936-12949, (2010).

65 Markowitz, J. E., Ivie, E., Kligler, L. & Gardner, T. J. Long-range Order in Canary Song. *PLoS computational biology* 9, e1003052, (2013).

66 Fentress, J. C. & Stilwell, F. P. Letter: Grammar of a movement sequence in inbred mice. *Nature* 244, 52-53, (1973).

SELECTED EMBODIMENTS

Although the above description discloses a number of embodiments of the present invention, other alternative aspects of the invention are disclosed in the following further embodiments.

Embodiment 1. A method for analyzing the motion of a subject to separate it into modules, the method comprising:
processing three dimensional video data frames that represent the motion of the subject using a computational model to partition the frames into at least one set of frames that represent modules and at least one set frames that represent transitions between the modules; and
storing, in a memory, the at least one set of frames that represent modules referenced to a data identifier that represents a type of animal behavior;

Embodiment 2. The method of embodiment 1, said processing comprises a step of isolating the subject from the background in the video data.

Embodiment 3. The method of embodiment 2, said processing further comprises a step of identifying an orientation of a feature of the subject on a set of frames of the video data with respect to a coordinate system common to each frame.

Embodiment 4. The method of embodiment 3, said processing further comprises a step of modifying the orientation of the subject in at least a subset of the set of frames so that the feature is oriented in the same direction with respect to the coordinate system to output a set of aligned frames.

Embodiment 5. The method of embodiment 4, said processing further comprises a step of processing the aligned frames using a principal component analysis (PCA) to output pose dynamics data, wherein the pose dynamics data represents a pose of the subject for each aligned frame through principal component space.

Embodiment 6. The method of embodiment 5, said processing further comprises a step of processing the aligned frames with a computational model to temporally segment the pose dynamics data into separate sets of modules wherein each of the sub-second module in a set of modules exhibits similar pose dynamics.

Embodiment 7. The method of embodiment 6, further comprising a step of displaying a representation of each of the sets of modules that occur with a frequency above a threshold in the three dimensional video data.

Embodiment 8. The method of embodiment 1, wherein the computational model comprises modeling the sub-second modules as a vector autoregressive process representing a stereotyped trajectory through PCA space.

Embodiment 9. The method of embodiment 1, wherein the computational model comprises modeling transition periods between sub-second modules using a Hidden Markov Model.

Embodiment 10. The method of embodiment 1, wherein the three dimensional video data is first processed to output a series of points in a multidimensional vector space, wherein each point represents the three dimensional pose dynamics of the subject.

Embodiment 11. The method of any one of embodiments 1-10, wherein the subject is an animal in an animal study.

Embodiment 12. The method of any one of embodiments 1-10, wherein the subject is a human.

Embodiment 13. A method for analyzing the motion of a subject to separate it into modules, the method comprising:
- pre-processing three dimensional video data that represents the motion of the subject to isolate the subject from the background;
- identifying an orientation of a feature of the subject on a set of frames of the video data with respect to a coordinate system common to each frame;
- modifying the orientation of the subject in at least a subset of the set of frames so that the feature is oriented in the same direction with respect to the coordinate system to output a set of aligned frames;
- processing the aligned frames using a principal component analysis to output pose dynamics data, wherein the pose dynamics data represents a pose of the subject for each aligned frame through principal component space;
- processing the aligned frames to temporally segment the pose dynamics data into separate sets of sub-second modules wherein each of the sub-second module in a set of modules exhibits similar pose dynamics; and
- displaying a representation of each of the sets of modules that occur with a frequency above a threshold in the three dimensional video data.

Embodiment 14. The method of embodiment 13, wherein the processing the aligned frames step is performed using a model free algorithm.

Embodiment 15. The method of embodiment 14, wherein the model free algorithm comprises computing an autocorrelogram.

Embodiment 16. The method of embodiment 13, wherein the processing the aligned frames step is performed using a model based algorithm.

Embodiment 17. The method of embodiment 16, wherein the model based algorithm is an AR-HMM algorithm.

Embodiment 18. The method of any one of embodiments 13-17, wherein the subject is an animal in an animal study.

Embodiment 19. The method of any one of embodiments 13-17, wherein the subject is a human.

Embodiment 20. A method of classifying a test compound, the method comprising:
- identifying a test behavioral representation that includes a set of modules in a test subject after the test compound is administered to the test subject;
- comparing the test behavioral representation to a plurality of reference behavioral representations, wherein each reference behavioral representation represents each class of drugs; and
- determining that the test compound belongs to a class of drugs if the test behavioral representation is identified by a classifier as matching the reference behavioral representation representing said class of drugs.

Embodiment 21. The method of embodiment 20, wherein the test behavioral representation is identified by
- receiving three dimensional video data representing the motion of the test subject;
  - processing the three dimensional data using a computational model to partition the data into at least one set of modules and at least one set of transition periods between the modules; and
  - assigning the at least one set of modules to a category that represents a type of animal behavior.

Embodiment 22. The method of embodiment 21, wherein the computational model comprises modeling the sub-second modules as a vector autoregressive process representing a stereotyped trajectory through principal component analysis (PCA) space.

Embodiment 23. The method of embodiment 21, wherein the computational model comprises modeling the transition periods using a Hidden Markov Model.

Embodiment 24. The method of any one of embodiments 20-23, wherein the three dimensional video data is first processed to output a series of points in a multidimensional vector space, wherein each point represents the 3D pose dynamics of the test subject.

Embodiment 25. The method of any one of embodiments 20-24, wherein the test compound is selected from the group consisting of a small molecule, an antibody or an antigen-binding fragment thereof, a nucleic acid, a polypeptide, a peptide, a peptidomimetic, a polysaccharide, a monosaccharide, a lipid, a glycosaminoglycan, and a combination thereof.

Embodiment 26. The method of any one of embodiments 20-25, wherein the test subject is an animal in an animal study.

Embodiment 27. A method for analyzing the motion of a subject to separate it into modules, the method comprising:
- receiving three dimensional video data representing the motion of the subject before and after administration of an agent to the subject;
- pre-processing the three dimensional video data to isolate the subject from the background;
- identifying an orientation of a feature of the subject on a set of frames of the video data with respect to a coordinate system common to each frame;
- modifying the orientation of the subject in at least a subset of the set of frames so that the feature is oriented in the same direction with respect to the coordinate system to output a set of aligned frames;
- processing the aligned frames using a principal component analysis to output pose dynamics data, wherein the pose dynamics data represents a pose of the subject for each aligned frame through principal component space;
- processing the aligned frames with a computational model to temporally segment the pose dynamics data into separate sets of sub-second modules wherein each of the sub-second module in a set of sub-second modules exhibits similar pose dynamics;
- determining the quantity of modules in each set of sub-second modules before administration of the agent to the subject;
- determining the quantity of modules in each set of sub-second modules after administration of the agent to the subject;
- comparing the quantity of modules in each set of sub-second modules before and after administration of the agent to the subject; and
- outputting an indication of the change in frequency of expression of the quantity of modules in each set of modules before and after administration of the agent to the subject.

Embodiment 28. The method of embodiment 27, wherein each set of sub-second modules is classified into a predetermined behavior module based on comparison to reference data representing behavior modules.

Embodiment 29. The method of embodiment 27 or 28, wherein the change in frequency of expression of the quantity of modules in each set of modules before and after administration of the agent to the subject is compared to the reference data representing a change in frequency of expression of modules after exposure to known categories of agents.

Embodiment 30. The method of embodiment 29, comprising the further step of classifying the agent as one of the plurality of known categories of agents based on the comparison to reference data representing the change in frequency after exposure to known categories of agents.

Embodiment 31. The method of any one of embodiments 27-30, wherein the agent is a pharmaceutically active compound.

Embodiment 32. The method of any one of embodiments 27-30, wherein the agent is visual or auditory stimulus.

Embodiment 33. The method of any one of embodiments 27-30, wherein the agent is an odorant.

Embodiment 34. The method of any one of embodiments 27-33, wherein the subject is an animal in an animal study.

Embodiment 35. The method of any one of embodiments 27-33, wherein the subject is a human.

Embodiment 36. A system for recording motion of a subject with a three dimensional video camera and parsing three dimensional video data output from the three dimensional video camera into sets of frames the represent different behaviors, the system comprising:
  a three dimensional video camera configured to output video data representing the motion of a subject;
    a memory in communication with the three dimensional video camera containing machine readable medium comprising machine executable code having stored thereon;
  a control system comprising one or more processors coupled to the memory, the control system configured to execute the machine executable code to cause the control system to:
  pre-process, using the control system, the video data to isolate the subject from the background;
  identify, using the control system, an orientation of a feature of the subject on a set of frames of the video data with respect to a coordinate system common to each frame;
  modify, using the control system, the orientation of the subject in at least a subset of the set of frames so that the feature is oriented in the same direction with respect to the coordinate system to output a set of aligned frames;
  process, using the control system, the set of aligned frames using a principal component analysis to output pose dynamics data for each frame of the set of aligned frames, wherein the pose dynamics data represents a pose of the subject for each aligned frame through principal component space;
  process, using the control system, the set of aligned frames to temporally segment the set of aligned frames into separate sets of sub-second modules wherein each set of sub-second modules includes only sub-second modules with similar pose dynamics; and
  store, in a database, each frame in the set of aligned frames referenced to its sub-second module.

Embodiment 37. The system of embodiment 36, wherein the control system is further configured to: send, to a display, a representation of a sub-set of the sets of sub-second modules that occur above a threshold in the separate sets of sub-second modules.

Embodiment 38. The system of embodiment 36, wherein the control system receives user input regarding a behavior tag for each of the sub-set of the sets of sub-second modules that occur above a threshold.

CONCLUSION

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

Particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

The invention claimed is:

1. A method for analyzing motion of a subject, the method comprising:
   processing three-dimensional video image data frames representing the motion of the subject using a model-free algorithm to output a first and a second set of modules, wherein each module in the first set of modules exhibits pose dynamics for 200-900 milliseconds, and each module in the second set of modules exhibits pose dynamics for 200-900 milliseconds; and
   identifying repeated modules of the subject's behavior using a template matching procedure for matching motifs of the subject's motion.

2. The method of claim 1, wherein each module in the first set of modules and the second set of modules exhibits pose dynamics satisfying a predetermined similarity threshold.

3. The method of claim 2, wherein the processing further comprises isolating the subject from a background in each frame of the three-dimensional video image data.

4. The method of claim 3, wherein the processing further comprises identifying an orientation of a feature of the subject on a set of frames of the three-dimensional video image data with respect to a coordinate system common to each frame.

5. The method of claim 4, wherein the processing further comprises modifying the orientation of the subject in at least a subset of the set of frames so that the feature is oriented in a same direction with respect to the coordinate system to output a set of aligned frames.

6. The method of claim 5, wherein the processing further comprises reducing dimensionality of the three-dimensional video image data frames using a principal component analysis (PCA) to output pose dynamics data representing a pose of the subject through principal component space.

7. The method of claim 5, wherein the processing further comprises reducing dimensionality of the three-dimensional video image data frames using a random projections technique.

8. The method of claim 1, wherein the processing further comprises identifying a time period of a behavior module of the subject by computing an auto-correlogram to evaluate timescale over which the subject's behavior is self-repeating.

9. The method of claim 1, wherein the processing further comprises performing a power-spectral density (PSD) analysis on the subject's behavioral data to further analyze its time domain structure.

10. The method of claim 1, wherein the processing further comprises automatically locating changepoints for transition periods between modules using a filtered derivative algorithm.

11. A non-transitory computer-readable medium storing processor-executable instructions that, when executed by at least one processor, cause the at least one processor to perform a method for analyzing motion of a subject, the method comprising:
    processing three-dimensional video image data frames representing the motion of the subject using a model-free algorithm to output a first and a second set of modules, wherein each module in the first set of modules exhibits pose dynamics for 200-900 milliseconds, and each module in the second set of modules exhibits pose dynamics for 200-900 milliseconds; and
    identifying repeated modules of the subject's behavior using a template matching procedure for matching motifs of the subject's motion.

12. A system for recording motion of a subject and parsing recorded image data into sets of frames that represent different behaviors of the subject, the system comprising:
    a three-dimensional video camera configured to output video image data representing the motion of the subject;
    a memory in communication with the three-dimensional video camera and having a non-transitory machine-readable storage medium with a machine-executable instruction set stored thereon; and
    a control system comprising one or more processors coupled to the memory, the one or more processors configured to execute the machine-executable instruction set to cause the control system to:
        process frames obtained using the video image data, the frames representing the motion of the subject, using a model-free algorithm to output a first and a second set of modules, wherein each module in the first set of modules exhibits pose dynamics for 200-900 milliseconds, and each module in the second set of modules exhibits pose dynamics for 200-900 milliseconds; and
        identify repeated modules of the subject's behavior using a template matching procedure for matching motifs of the subject's motion.

13. The system of claim 12, wherein the control system is further configured to:
    pre-process the video image data to isolate the subject from a background of the video image data; and
    identify an orientation of a feature of the subject on a set of frames of the video image data with respect to a coordinate system common to each frame.

14. The system of claim 13, wherein the control system is further configured to modify the orientation of the feature of the subject in at least a subset of the set of frames so that the feature is oriented in a same direction with respect to the coordinate system to output a set of aligned frames.

15. The system of claim 14, wherein the control system is further configured to:

process the set of aligned frames using a principal component analysis to output pose dynamics data for each frame of the set of aligned frames, wherein the pose dynamics data represents a pose of the subject for each aligned frame through principal component space; and process, using the control system, the set of aligned frames to temporally segment the pose dynamics data into a plurality of sets of modules, wherein each module within a set of modules exhibits similar pose dynamics satisfying a predetermined similarity threshold and comprises 200-900 milliseconds.

16. The system of claim 15, wherein the control system is further configured to store, in a database, each frame in the set of aligned frames referenced to its module.

17. The system of claim 12, wherein the control system is further configured to send, to a display, a representation of a sub-set of the first and second sets of modules that occur above a predetermined similarity threshold.

18. The system of claim 12, wherein the control system is further configured to automatically apply a behavior tag to video image data outputted from the three-dimensional video camera representing motion of a second subject.

19. The system of claim 12, wherein the video image data represents motion of the subject before and after administration of an agent to the subject, and wherein the control system is further configured to:
    determine a quantity of modules in the first and second sets of modules before administration of the agent to the subject;
    determine a quantity of modules in the first and second sets of modules after administration of the agent to the subject; and
    output an indication of a change in frequency of expression of the quantity of modules in each of the first and second sets of modules before and after administration of the agent to the subject.

20. The system of claim 19, wherein the agent is (i) a pharmaceutically-active compound, (ii) a visual stimulus, (iii) an auditory stimulus, or (iv) an odorant.

* * * * *